(12) United States Patent
Greenfield et al.

(10) Patent No.: US 10,301,603 B2
(45) Date of Patent: *May 28, 2019

(54) CAR ENZYMES AND IMPROVED PRODUCTION OF FATTY ALCOHOLS

(71) Applicant: Reg Life Sciences, LLC, Ames, IA (US)

(72) Inventors: Derek L. Greenfield, South San Francisco, CA (US); Elizabeth J. Clarke, South San Francisco, CA (US); Eli S. Groban, South San Francisco, CA (US); Vikranth Arlagadda, South San Francisco, CA (US); Sungwon Lee, South San Francisco, CA (US); Xuezhi Li, South San Francisco, CA (US); Zhihao Hu, South San Francisco, CA (US); Baolong Zhu, South San Francisco, CA (US)

(73) Assignee: Reg Life Sciences, LLC, Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/695,205

(22) Filed: Sep. 5, 2017

(65) Prior Publication Data

US 2018/0135028 A1    May 17, 2018

Related U.S. Application Data

(63) Continuation of application No. 15/154,636, filed on May 13, 2016, now Pat. No. 9,758,769, which is a continuation of application No. 14/390,350, filed as application No. PCT/US2013/035040 on Apr. 2, 2013, now Pat. No. 9,340,801.

(60) Provisional application No. 61/619,309, filed on Apr. 2, 2012.

(51) Int. Cl.
*C12N 9/06* (2006.01)
*C12N 9/02* (2006.01)
*C12P 7/04* (2006.01)
*C12P 7/64* (2006.01)

(52) U.S. Cl.
CPC ............ *C12N 9/0008* (2013.01); *C12P 7/04* (2013.01); *C12Y 102/99006* (2013.01); *C12P 7/6409* (2013.01); *Y02P 20/52* (2015.11)

(58) Field of Classification Search
CPC .. C12N 9/0008; C12P 7/04; C12Y 102/99006
USPC ................... 435/191, 252.3, 320.1
See application file for complete search history.

(56) References Cited

U.S. PATENT DOCUMENTS

| | | |
|---|---|---|
| 5,000,000 A | 3/1991 | Ingram et al. |
| 5,028,539 A | 7/1991 | Ingram et al. |
| 5,424,202 A | 6/1995 | Ingram et al. |
| 5,482,846 A | 1/1996 | Ingram et al. |
| 5,602,030 A | 2/1997 | Ingrahm et al. |
| 5,939,250 A | 8/1999 | Short |
| 5,965,408 A | 10/1999 | Short |
| 7,169,588 B2 | 1/2007 | Burch et al. |
| 8,097,439 B2 * | 1/2012 | Alibhai ............... C12N 9/0006 435/147 |
| 9,340,801 B2 * | 5/2016 | Greenfield .......... C12N 9/0008 |
| 9,758,769 B2 * | 9/2017 | Greenfield .......... C12N 9/0008 |
| 2004/0180400 A1 | 9/2004 | Rosazza et al. |
| 2009/0140696 A1 | 6/2009 | Okuto |
| 2010/0105963 A1 | 4/2010 | Hu |
| 2010/0298612 A1 | 11/2010 | Behrouzian et al. |
| 2011/0250663 A1 | 10/2011 | Schirmer et al. |
| 2012/0329119 A1 | 12/2012 | Burgard et al. |

FOREIGN PATENT DOCUMENTS

| | | |
|---|---|---|
| DE | 10 2004 052 115 | 4/2006 |
| WO | WO-2007/136762 A2 | 11/2007 |
| WO | WO-2008/147781 | 12/2008 |
| WO | WO-2009/085278 | 7/2009 |
| WO | WO-2010/062480 A1 | 6/2010 |
| WO | WO-2010/127318 | 11/2010 |
| WO | WO-2010/135624 | 11/2010 |
| WO | WO-2011/047101 | 4/2011 |
| WO | WO-2012/135789 | 10/2012 |
| WO | WO-2012/154329 | 11/2012 |

OTHER PUBLICATIONS

Notification of Reasons for Refusal issued on Korean Application 10-2017-7026945, dated Apr. 24, 2018.
Examiner's Report issued on Malaysian application PI 2014002838, dated Mar. 30, 2018.
Akhtar et al., "Carboxylic acid reductase is a versatile enzyme for the conversion of fatty acids into fuels and chemical commodities," Proceedings of the National Academy of Sciences, vol. 110, No. 1, Jan. 2, 2013, pp. 87-92.
Altschul et al. "Protein Database Searches Using Compositionally Adjusted Substitution Matrices," (2005) FEBS J. 272(20):5101-5109.
Amann et al., "Tightly regulated tac promoter vectors useful for the expression of unfused and fused proteins in *Escherichia coli*," Gene, 69: 301-315 (1988).
Arkin et al. (1992) Proc. Natl. Acad. Sci. U.S.A. 89:7811-7815.
Arkin et al., "An algorithm for protein engineering: Simulations of recursive ensemble mutagenesis," Proc. Natl. Acad. Sci. U.S.A., vol. 89, pp. 7811-7815 (1992).
Baldari et al. "A novel leader peptide which allows efficient secretion of a fragment of human interluken 1beta in *Saccharomyces serevisiae*," (1987) EMBO J. 6:229-234.
Bowie et al. "Deciphering the Message in Protein Sequences: Tolerance to Amino Acid Substitutions," (1990) Science, 247:1306-1310.

(Continued)

*Primary Examiner* — Tekchand Saidha
(74) *Attorney, Agent, or Firm* — Foley & Lardner LLP

(57) ABSTRACT

The disclosure relates to variant carboxylic acid reductase (CAR) enzymes for the improved production of fatty alcohols in recombinant host cells.

20 Claims, 13 Drawing Sheets

Specification includes a Sequence Listing.

(56) References Cited

OTHER PUBLICATIONS

Caldwell et al., "Randomization of Genes by PCR Mutagenesis," PCR Methods Applic. 2: 28-33 (1992).
Caviglia et al., "Rat Long Chain Acyl-CoA Synthetase 5, but Not 1, 2, 3, or 4, Complements *Escherichia coli* fadD," J. Biol. Chem. 279(12): 11163-11169 (2004).
Communication issued on European Patent Application 13766728.3, dated Oct. 1, 2015.
Communication on European patent Application 09803969.6, dated Sep. 24, 2015.
Cronan. "A family of arabinose-inducible *Escherichia coli* expression vectors having pBR322 copy control." (2006) Plasmid, 55)2: 152-157.
Datsenko et al., "One-step Inactivation of Chromosomal Genes in *Escherichia coli* K-12 using PCR Products," Proc. Natl. Acad. Sci. U.S.A., 97(12): 6640-6645 (2000).
Examination Report issued on Australian Application 2013243602, dated Aug. 13, 2016.
Extended Search Report issued on European Application 16198810.0, dated Jan. 30, 2017.
First Substantive official Action issued on Colombian Application 14-240.039, dated Sep. 27, 2016, English translation only.
Grosjean et al., "Preferential codon usage in prokaryotic genes: the optimal codon-anticodon interaction energy and the selective codon usage in efficiently expressed genes," Gene 18:199-209 (1982).
He et al., "Nocardia sp. Carboxylic Acid Reductase: Cloning, Expresssion and Characterization of a New Aldehyde Oxidoreductase Family," Appl. Environ. Microbiol., 70(3): 874-1881 (2004).
International Search Report on PCT/US2013/035040, dated Jan. 22, 2014.
Kalscheuer et al., "Microdiesel: *Escherichia coli* engineered for fuel production," Microbiology, vol. 152, Jan. 1, 2006, pp. 2529-2536.
Kurjan et al., Struture of a Yeast Pheromone Gene (MFx): A Putative x-Factor precursor Contains Four Tandem Copies of Mature x-Factor, Cell, vol. 30, pp. 933-943 (1982).
Leung et al. "A Journal of Methods in Cell and Molecular Biology," Technique 1:(1): 11-15 (1989).
Lo et al., "Substrate Specificities of *Excherichia coli* Thioesterase I/Protease I/Lysophospholipase L1 are Governed by Its Switch Loop Movement," Biochemistry 2005, 44, pp. 1971-1979.
Lucklow et al. "High Level Expression of Nonfused Foreign Genes with Autographa californica Nuclear Polyhedrosis Virus Expression Vectors," (1989) Virology 170, pp. 31-39.
McKenzie et al., "Fast, easy and efficient: site-specific insertion of transgenes into Enterobacterial chromosomes using Tn7 without need for selection of the insertion event," BMC Microbiology 6: 39 (2006), 7 pages.
Needleman et al., "A General Method Applicable to the Search for Similarities in the Amino Acid Sequence of Two Proteins," J. Mol. Biol. 48:444-453 (1970).
Non-Final Office Action issued on U.S. Appl. 15/154,636, dated Jan. 23, 2017.
Notice of Reasons for Rejection issued on Japanese application 2015-504688, dated Feb. 13, 2017.
Notification of Reasons for Refusal issued on Korean Application 10-2014-703074, dated Oct. 24, 2016, English translation only.
Office Action issued on Chinese Application 201380026546.8, dated Mar. 1, 2017.
Office Action issued on Chinese Application 201380026546.8, dated Nov. 10, 2016, English Translation only.
Palmeros et al., "A family of removable cassets designed to obtain antiobiotic-resistance-free genomic modifications of *Escherichia coli* and other bacteria," Gene, vol. 247, pp. 255-264, 2000.
Reidhaar-Olson et al., "Combinatorial Cassette Mutagenesis as a Probe of the Informational Content of Protein Sequences," Science 241: 53-57 (1988).
Schultz et al., "Expression and secretion in yeast of a 400-kDa envelope glycoprotein derived from Epstein-Barr virus," Gene 54: 113-123 (1987).
Smith et al. "Production of Human Beta Interferon in Insect Cells Infected with a Vaculovirus Expression Vector," (1983) Mol. Cell. Biol. 3:2156-2165.
Smith et al., "Production of Human Beta Interferon in Insect Cells Infected with a Vaculovirus Expression Vector," Mol. Cell Biol. 3(12): 2156-2165 (1983).
Smith et al., "Single-step purification of polypeptides expressed in *Escherichia coli* as fusions with glutathione S-transferase," Gene 67: 31-40 (1988).
Stemmer "DNA shuffling by random fragmentation and reassembly: In vitro recombination for molecular evolution," (1994) Proc. Natl. Acad. Sci. U.S.A. 91:10747-10751.
Stemmer, "DNA shuffling by random fragmentation and reassembly: In vitro recombination for molecular evolution," Proc. Natl. Acad. Sci. USA. 91: 10747-10751 (1994).
Studier et al., Gene Expression Technology: Methods in Enzymology 185, Academic Press, San Diego, CA, pp. 60-89 (1990).
Yang Fan et al., "Genome dynamics and diversity of Shigella species, the etiologic agents of bacillary dysentery," Nucleic Acids Research, Oxford University Press, Jan. 1, 2005, vol. 33, No. 19, pp. 6445-6458.

* cited by examiner

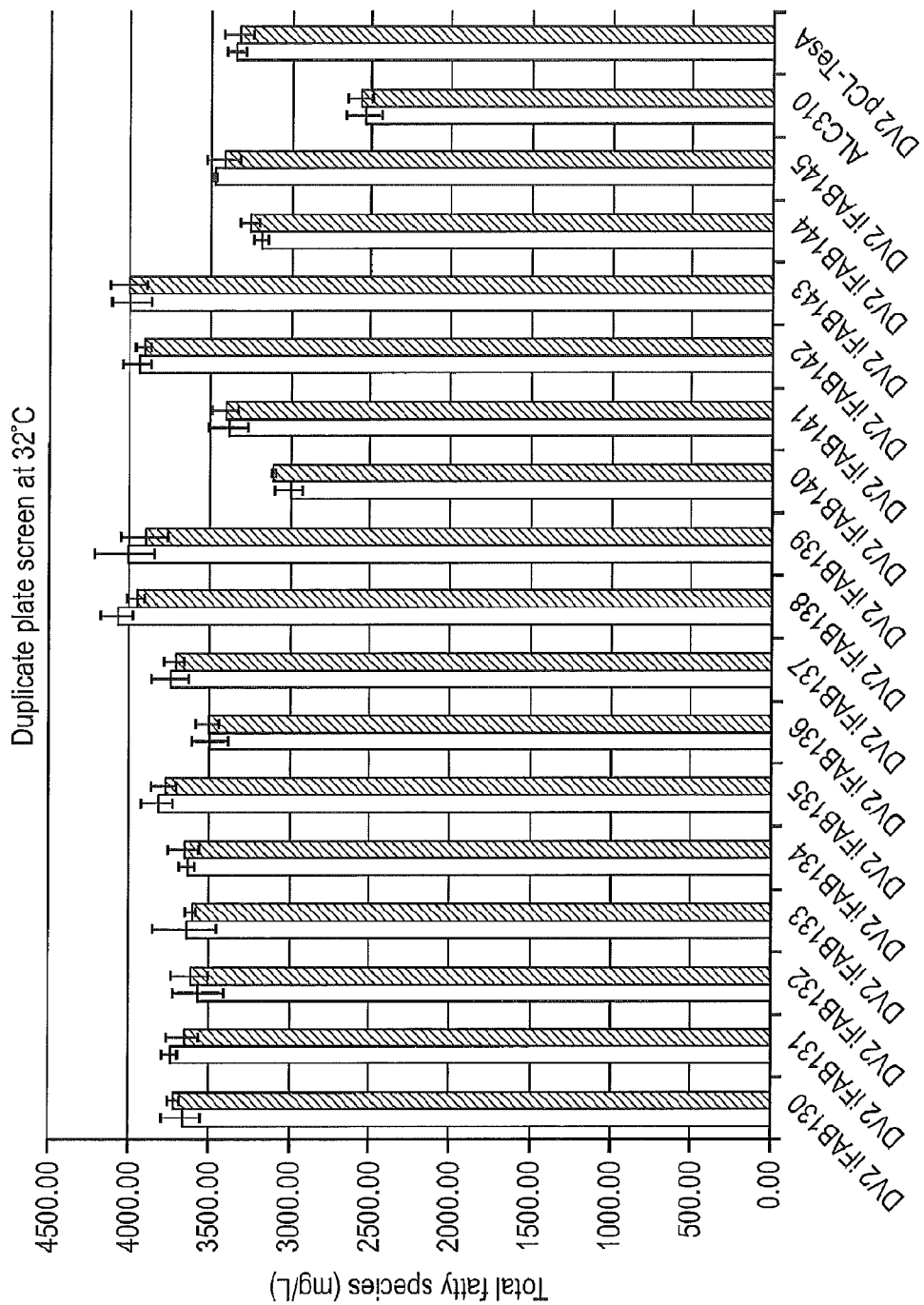

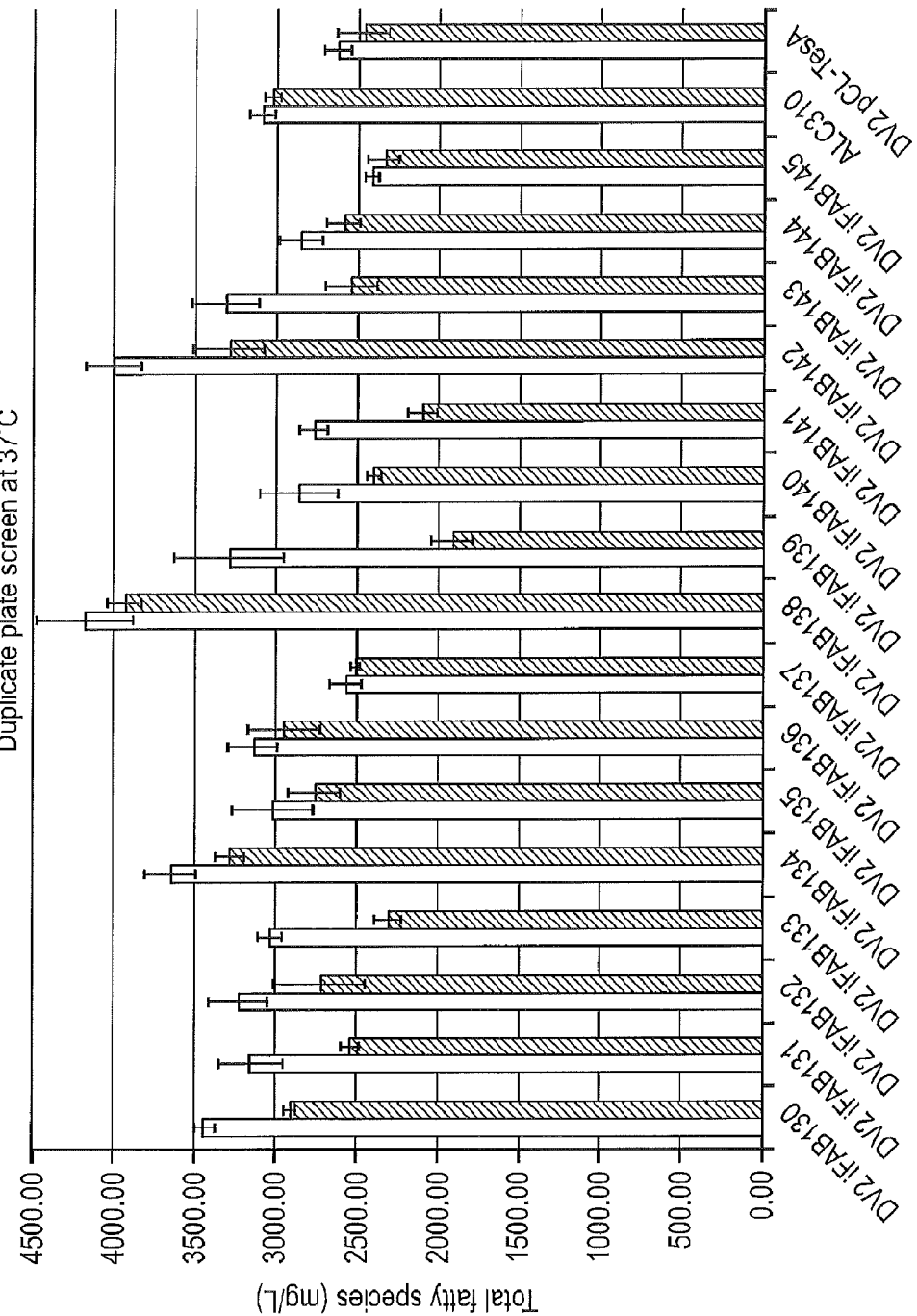

SEQUENCE LISTING

<160> NUMBER OF SEQ ID NOS: 56

<210> SEQ ID NO 1
<211> LENGTH: 1232
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
ttgtccatct ttatataatt tgggggtagg gtgttcttta tgtaaaaaaa acgttttagg      60
atgcatatgg cggccgcata acttcgtata gcatacatta tacgaagtta tctagagttg    120
catgcctgca ggtccgctta ttatcactta ttcaggcgta gcaaccaggc gtttaagggc    180
accaataact gccttaaaaa aattacgccc cgccctgcca ctcatcgcag tactgttgta    240
attcattaag cattctgccg acatggaagc catcacaaac ggcatgatga acctgaatcg    300
ccagcggcat cagcaccttg tcgccttgcg tataatattt gcccatggtg aaaacggggg    360
cgaagaagtt gtccatattg gccacgttta aatcaaaact ggtgaaactc acccagggat    420
tggctgagac gaaaaacata ttctcaataa accctttagg aaataggcc aggttttcac     480 cgtaacacgc cacatcttgc gaatatatgt gtagaaactg ccggaaatcg tcgtggtatt    540
cactccagag cgatgaaaac gtttcagttt gctcatggaa aacgtgtaa caagggtgaa     600 cactatccca tcaccagc tcaccgtctt tcattgccat acggaattcc ggatgagcat      660
tcatcaggcg ggcaagaatg tgaataaagg ccggataaaa cttgtgctta tttttcttta    720
cggtctttaa aaaggccgta atatccagct gaacggtctg gttataggta cattgagcaa    780
ctgactgaaa tgcctcaaaa tgttctttac gatgccattg ggatatatca cggtggtat     840 atccagtgat tttttttctcc attttagctt ccttagctcc tgaaaatctc gataactcaa    900
aaaatacgcc cggtagtgat cttatttcat tatggtgaaa gttggaacct cttacgtgcc    960
gatcaacgtc tcattttcgc caaaagttgg cccagggctt cccggtatca acagggacac   1020
caggatttat ttattctgcg aagtgatctt ccgtcacagg tatttattcg actctagata   1080
acttcgtata gcatacatta tacgaagtta tggatccagc ttatcgatac cgtcaaacaa   1140
atcataaaaa atttatttgc tttcaggaaa atttttctgt ataatagatt caattgcgat   1200
gacgacgaac acgcacctgc aggaggagac ca                                  1232

<210> SEQ ID NO 2
<211> LENGTH: 232
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
ttgtccatct ttatataatt tgggggtagg gtgttcttta tgtaaaaaaa acgttttagg      60
atgcatatgg cggccgcata acttcgtata gcatacatta tacgaagtta tggatccagc    120
ttatcgatac cgtcaaacaa atcataaaaa atttatttgc tttcaggaaa atttttctgt    180
ataatagatt caattgcgat gacgacgaac acgcacctgc aggaggagac ca             232

<210> SEQ ID NO 3
<211> LENGTH: 340

<212> TYPE: PRT
<213> ORGANISM: Acinetobacter sp.

<400> SEQUENCE: 3

Met Ser Asn His Gln Ile Arg Ala Tyr Ala Ala Met Gln Ala Gly Glu
1               5                   10                  15

Gln Val Val Pro Tyr Gln Phe Asp Ala Gly Glu Leu Lys Ala His Gln
            20                  25                  30

Val Glu Val Lys Val Glu Tyr Cys Gly Leu Cys His Ser Asp Leu Ser
        35                  40                  45

Val Ile Asn Asn Glu Trp Gln Ser Ser Val Tyr Pro Ala Val Ala Gly
50                  55                  60

His Glu Ile Ile Gly Thr Ile Ile Ala Leu Gly Ser Glu Ala Lys Gly
65                  70                  75                  80

Leu Lys Leu Gly Gln Arg Val Gly Ile Gly Trp Thr Ala Glu Thr Cys
                85                  90                  95

Gln Ala Cys Asp Pro Cys Ile Gly Gly Asn Gln Val Leu Cys Thr Gly
            100                 105                 110

Glu Lys Lys Ala Thr Ile Ile Gly His Ala Gly Gly Phe Ala Asp Lys
        115                 120                 125

Val Arg Ala Gly Trp Gln Trp Val Ile Pro Leu Pro Asp Asp Leu Asp
130                 135                 140

Pro Glu Ser Ala Gly Pro Leu Leu Cys Gly Gly Ile Thr Val Leu Asp
145                 150                 155                 160

Pro Leu Leu Lys His Lys Ile Gln Ala Thr His His Val Gly Val Ile
                165                 170                 175

Gly Ile Gly Gly Leu Gly His Ile Ala Ile Lys Leu Leu Lys Ala Trp
            180                 185                 190

Gly Cys Glu Ile Thr Ala Phe Ser Ser Asn Pro Asp Lys Thr Glu Glu
        195                 200                 205

Leu Lys Ala Asn Gly Ala Asp Gln Val Val Asn Ser Arg Asp Ala Gln
210                 215                 220

Ala Ile Lys Gly Thr Arg Trp Lys Leu Ile Ile Leu Ser Thr Ala Asn
225                 230                 235                 240

Gly Thr Leu Asn Val Lys Ala Tyr Leu Asn Thr Leu Ala Pro Lys Gly
                245                 250                 255

Ser Leu His Phe Leu Gly Val Thr Leu Glu Pro Ile Pro Val Ser Val
            260                 265                 270

Gly Ala Ile Met Gly Gly Ala Lys Ser Val Thr Ser Ser Pro Thr Gly
        275                 280                 285

Ser Pro Leu Ala Leu Arg Gln Leu Leu Gln Phe Ala Ala Arg Lys Asn
290                 295                 300

Ile Ala Pro Gln Val Glu Leu Phe Pro Met Ser Gln Leu Asn Glu Ala
305                 310                 315                 320

Ile Glu Arg Leu His Ser Gly Gln Ala Arg Tyr Arg Ile Val Leu Lys
                325                 330                 335

Ala Asp Phe Asp
            340

<210> SEQ ID NO 4
<211> LENGTH: 314
<212> TYPE: PRT
<213> ORGANISM: Acinetobacter sp.

<400> SEQUENCE: 4

```
Met Ala Thr Thr Asn Val Ile His Ala Tyr Ala Ala Met Gln Ala Gly
1               5                   10                  15

Glu Ala Leu Val Pro Tyr Ser Phe Asp Ala Gly Glu Leu Gln Pro His
            20                  25                  30

Gln Val Glu Val Lys Val Glu Tyr Cys Gly Leu Cys His Ser Asp Val
        35                  40                  45

Ser Val Leu Asn Asn Glu Trp His Ser Ser Val Tyr Pro Val Val Ala
50                  55                  60

Gly His Glu Val Ile Gly Thr Ile Thr Gln Leu Gly Ser Glu Ala Lys
65                  70                  75                  80

Gly Leu Lys Ile Gly Gln Arg Val Gly Ile Gly Trp Thr Ala Glu Ser
                85                  90                  95

Cys Gln Ala Cys Asp Gln Cys Ile Ser Gly Gln Gln Val Leu Cys Thr
            100                 105                 110

Gly Glu Asn Thr Ala Thr Ile Ile Gly His Ala Gly Gly Phe Ala Asp
        115                 120                 125

Lys Val Arg Ala Gly Trp Gln Trp Val Ile Pro Leu Pro Asp Glu Leu
    130                 135                 140

Asp Pro Thr Ser Ala Gly Pro Leu Leu Cys Gly Gly Ile Thr Val Phe
145                 150                 155                 160

Asp Pro Ile Leu Lys His Gln Ile Gln Ala Ile His His Val Ala Val
                165                 170                 175

Ile Gly Ile Gly Gly Leu Gly His Met Ala Ile Lys Leu Leu Lys Ala
            180                 185                 190

Trp Gly Cys Glu Ile Thr Ala Phe Ser Ser Asn Pro Asn Lys Thr Asp
        195                 200                 205

Glu Leu Lys Ala Met Gly Ala Asp His Val Val Asn Ser Arg Asp Asp
    210                 215                 220

Ala Glu Ile Lys Ser Gln Gln Gly Lys Phe Asp Leu Leu Leu Ser Thr
225                 230                 235                 240

Val Asn Val Pro Leu Asn Trp Asn Ala Tyr Leu Asn Thr Leu Ala Pro
                245                 250                 255

Asn Gly Thr Phe His Phe Leu Gly Val Val Met Glu Pro Ile Pro Val
            260                 265                 270

Pro Val Gly Ala Leu Leu Gly Gly Ala Lys Ser Leu Thr Ala Ser Pro
        275                 280                 285

Thr Gly Ser Pro Ala Ala Leu Arg Lys Leu Leu Glu Phe Ala Ala Arg
    290                 295                 300

Lys Asn Ile Ala Pro Gln Ile Glu Met Tyr
305                 310

<210> SEQ ID NO 5
<211> LENGTH: 1020
<212> TYPE: DNA
<213> ORGANISM: Escherichia coli

<400> SEQUENCE: 5
atgtcgatga taaaaagcta tgccgcaaaa gaagcgggcg gcgaactgga agtttatgag      60
tacgatcccg gtgagctgag gccacaagat gttgaagtgc aggtggatta ctgcgggatc     120
tgccattccg atctgtcgat gatcgataac gaatggggat tttcacaata tccgctggtt     180
gccgggcatg aggtgattgg gcgcgtggtg cactcgggga cgccgcgca ggataaaggt      240 ttgcaggtcg gtcagcgtgt cgggattggc tggacggcgc gtagctgtgg tcactgcgac     300
gcctgtatta gcggtaatca gatcaactgc gagcaaggtg cggtgccgac gattatgaat     360
```

```
cgcggtggct tgccgagaa gttgcgtgcg gactggcaat gggtgattcc actgccagaa    420
aatattgata tcgagtccgc cgggccgctg ttgtgcggcg gtatcacggt ctttaaacca    480
ctgttgatgc accatatcac tgctaccagc cgcgttgggg taattggtat tggcgggctg    540
gggcatatcg ctataaaact tctgcacgca atgggatgcg aggtgacagc ctttagttct    600
aatccggcga agagcagga agtgctggcg atgggtgccg ataaagtggt gaatagccgc    660
gatccgcagg cactgaaagc actggcgggg cagtttgatc tcattatcaa caccgtcaac    720
gtcagcctcg actggcagcc ctattttgag gcgctgacct atggcggtaa tttccatacg    780
gtcggtgcgt tctcacgcc gctgtctgtt ccggccttta cgttaattgc gggcgatcgc    840
agcgtctctg ttctgctac cggcacgcct tatgagctgc gtaagctgat gcgttttgcc    900
gcccgcagca aggttgcgcc gaccaccgaa ctgttcccga tgtcgaaaat taacgacgcc    960
atccagcatg tgcgcgacgg taaggcgcgt taccgcgtgg tgttgaaagc cgattttga   1020
```

<210> SEQ ID NO 6
<211> LENGTH: 1174
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Leu Val Ile Val Glu Thr Leu
    210                 215                 220

Asp Ala Val Arg Ala Arg Gly Arg Asp Leu Pro Ala Ala Pro Leu Phe
225                 230                 235                 240
```

```
Val Pro Asp Thr Asp Asp Pro Leu Ala Leu Leu Ile Tyr Thr Ser
            245                 250                 255

Gly Ser Thr Gly Thr Pro Lys Gly Ala Met Tyr Thr Asn Arg Leu Ala
                260                 265                 270

Ala Thr Met Trp Gln Gly Asn Ser Met Leu Gln Gly Asn Ser Gln Arg
            275                 280                 285

Val Gly Ile Asn Leu Asn Tyr Met Pro Met Ser His Ile Ala Gly Arg
        290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
                340                 345                 350

Arg Tyr Gln Ser Glu Leu Asp Arg Arg Ser Val Ala Gly Ala Asp Leu
            355                 360                 365

Asp Thr Leu Asp Arg Glu Val Lys Ala Asp Leu Arg Gln Asn Tyr Leu
        370                 375                 380

Gly Gly Arg Phe Leu Val Ala Val Val Gly Ser Ala Pro Leu Ala Ala
385                 390                 395                 400

Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
                420                 425                 430

Ile Gln Arg Pro Pro Val Leu Asp Tyr Lys Leu Val Asp Val Pro Glu
            435                 440                 445

Leu Gly Tyr Phe Arg Thr Asp Arg Pro His Pro Arg Gly Glu Leu Leu
        450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
                500                 505                 510

Asn Val Leu Lys Leu Ser Gln Gly Glu Phe Val Thr Val Ala His Leu
            515                 520                 525

Glu Ala Val Phe Ala Ser Ser Pro Leu Ile Arg Gln Ile Phe Ile Tyr
        530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
                580                 585                 590

Ile Pro Arg Asp Phe Leu Ile Glu Thr Glu Pro Phe Thr Ile Ala Asn
            595                 600                 605

Gly Leu Leu Ser Gly Ile Ala Lys Leu Leu Arg Pro Asn Leu Lys Glu
        610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655
```

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
        675                 680                 685

Ser Leu Ser Ala Leu Ser Phe Ser Asn Leu Leu His Glu Ile Phe Gly
    690                 695                 700

Val Glu Val Pro Val Gly Val Val Ser Pro Ala Asn Glu Leu Arg
705             710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
            740                 745                 750

Asp Leu Thr Leu Asp Lys Phe Ile Asp Ala Arg Thr Leu Ala Ala Ala
            755                 760                 765

Asp Ser Ile Pro His Ala Pro Val Pro Ala Gln Thr Val Leu Leu Thr
        770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Arg Lys Arg Leu Asp Ser Ala Phe Asp Ser Gly
            820                 825                 830

Asp Pro Gly Leu Leu Glu His Tyr Gln Gln Leu Ala Ala Arg Thr Leu
        835                 840                 845

Glu Val Leu Ala Gly Asp Ile Gly Asp Pro Asn Leu Gly Leu Asp Asp
850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
            900                 905                 910

Arg Lys Pro Val Thr Tyr Leu Ser Thr Val Gly Val Ala Asp Gln Val
        915                 920                 925

Asp Pro Ala Glu Tyr Gln Glu Asp Ser Asp Val Arg Glu Met Ser Ala
930                 935                 940

Val Arg Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Ser Asp Met Ile Leu Ala His Ser Arg Tyr
            980                 985                 990

Ala Gly Gln Leu Asn Val Gln Asp  Val Phe Thr Arg Leu  Ile Leu Ser
        995                 1000                1005

Leu Val  Ala Thr Gly Ile Ala  Pro Tyr Ser Phe Tyr  Arg Thr Asp
    1010                1015                1020

Ala Asp  Gly Asn Arg Gln Arg  Ala His Tyr Asp Gly  Leu Pro Ala
    1025                1030                1035

Asp Phe  Thr Ala Ala Ala Ile  Thr Ala Leu Gly Ile  Gln Ala Thr
    1040                1045                1050

Glu Gly  Phe Arg Thr Tyr Asp  Val Leu Asn Pro Tyr  Asp Asp Gly
    1055                1060                1065

Ile Ser  Leu Asp Glu Phe Val  Asp Trp Leu Val Glu  Ser Gly His

```
                1070                1075                1080
Pro Ile Gln Arg Ile Thr Asp Tyr Ser Asp Trp Phe His Arg Phe
            1085                1090                1095
Glu Thr Ala Ile Arg Ala Leu Pro Glu Lys Gln Arg Gln Ala Ser
    1100                1105                1110
Val Leu Pro Leu Leu Asp Ala Tyr Arg Asn Pro Cys Pro Ala Val
        1115                1120                1125
Arg Gly Ala Ile Leu Pro Ala Lys Glu Phe Gln Ala Ala Val Gln
    1130                1135                1140
Thr Ala Lys Ile Gly Pro Glu Gln Asp Ile Pro His Leu Ser Ala
        1145                1150                1155
Pro Leu Ile Asp Lys Tyr Val Ser Asp Leu Glu Leu Leu Gln Leu
        1160                1165                1170
Leu
```

<210> SEQ ID NO 7
<211> LENGTH: 1173
<212> TYPE: PRT
<213> ORGANISM: Mycobacterium smegmatis

<400> SEQUENCE: 7

```
Met Thr Ser Asp Val His Asp Ala Thr Asp Gly Val Thr Glu Thr Ala
1               5                   10                  15
Leu Asp Asp Glu Gln Ser Thr Arg Arg Ile Ala Glu Leu Tyr Ala Thr
                20                  25                  30
Asp Pro Glu Phe Ala Ala Ala Pro Leu Pro Ala Val Val Asp Ala
            35                  40                  45
Ala His Lys Pro Gly Leu Arg Leu Ala Glu Ile Leu Gln Thr Leu Phe
    50                  55                  60
Thr Gly Tyr Gly Asp Arg Pro Ala Leu Gly Tyr Arg Ala Arg Glu Leu
65                  70                  75                  80
Ala Thr Asp Glu Gly Gly Arg Thr Val Thr Arg Leu Leu Pro Arg Phe
                85                  90                  95
Asp Thr Leu Thr Tyr Ala Gln Val Trp Ser Arg Val Gln Ala Val Ala
            100                 105                 110
Ala Ala Leu Arg His Asn Phe Ala Gln Pro Ile Tyr Pro Gly Asp Ala
        115                 120                 125
Val Ala Thr Ile Gly Phe Ala Ser Pro Asp Tyr Leu Thr Leu Asp Leu
    130                 135                 140
Val Cys Ala Tyr Leu Gly Leu Val Ser Val Pro Leu Gln His Asn Ala
145                 150                 155                 160
Pro Val Ser Arg Leu Ala Pro Ile Leu Ala Glu Val Glu Pro Arg Ile
                165                 170                 175
Leu Thr Val Ser Ala Glu Tyr Leu Asp Leu Ala Val Glu Ser Val Arg
            180                 185                 190
Asp Val Asn Ser Val Ser Gln Leu Val Val Phe Asp His His Pro Glu
        195                 200                 205
Val Asp Asp His Arg Asp Ala Leu Ala Arg Ala Arg Glu Gln Leu Ala
    210                 215                 220
Gly Lys Gly Ile Ala Val Thr Thr Leu Asp Ala Ile Ala Asp Glu Gly
225                 230                 235                 240
Ala Gly Leu Pro Ala Glu Pro Ile Tyr Thr Ala Asp His Asp Gln Arg
                245                 250                 255
Leu Ala Met Ile Leu Tyr Thr Ser Gly Ser Thr Gly Ala Pro Lys Gly
```

```
              260                 265                 270
Ala Met Tyr Thr Glu Ala Met Val Ala Arg Leu Trp Thr Met Ser Phe
            275                 280                 285
Ile Thr Gly Asp Pro Thr Pro Val Ile Asn Val Asn Phe Met Pro Leu
            290                 295                 300
Asn His Leu Gly Gly Arg Ile Pro Ile Ser Thr Ala Val Gln Asn Gly
305                 310                 315                 320
Gly Thr Ser Tyr Phe Val Pro Glu Ser Asp Met Ser Thr Leu Phe Glu
                325                 330                 335
Asp Leu Ala Leu Val Arg Pro Thr Glu Leu Gly Leu Val Pro Arg Val
                340                 345                 350
Ala Asp Met Leu Tyr Gln His His Leu Ala Thr Val Asp Arg Leu Val
            355                 360                 365
Thr Gln Gly Ala Asp Glu Leu Thr Ala Glu Lys Gln Ala Gly Ala Glu
        370                 375                 380
Leu Arg Glu Gln Val Leu Gly Gly Arg Val Ile Thr Gly Phe Val Ser
385                 390                 395                 400
Thr Ala Pro Leu Ala Ala Glu Met Arg Ala Phe Leu Asp Ile Thr Leu
                405                 410                 415
Gly Ala His Ile Val Asp Gly Tyr Gly Leu Thr Glu Thr Gly Ala Val
                420                 425                 430
Thr Arg Asp Gly Val Ile Val Arg Pro Pro Val Ile Asp Tyr Lys Leu
        435                 440                 445
Ile Asp Val Pro Glu Leu Gly Tyr Phe Ser Thr Asp Lys Pro Tyr Pro
        450                 455                 460
Arg Gly Glu Leu Leu Val Arg Ser Gln Thr Leu Thr Pro Gly Tyr Tyr
465                 470                 475                 480
Lys Arg Pro Glu Val Thr Ala Ser Val Phe Asp Arg Asp Gly Tyr Tyr
                485                 490                 495
His Thr Gly Asp Val Met Ala Glu Thr Ala Pro Asp His Leu Val Tyr
                500                 505                 510
Val Asp Arg Arg Asn Asn Val Leu Lys Leu Ala Gln Gly Glu Phe Val
                515                 520                 525
Ala Val Ala Asn Leu Glu Ala Val Phe Ser Gly Ala Ala Leu Val Arg
            530                 535                 540
Gln Ile Phe Val Tyr Gly Asn Ser Glu Arg Ser Phe Leu Leu Ala Val
545                 550                 555                 560
Val Val Pro Thr Pro Glu Ala Leu Glu Gln Tyr Asp Pro Ala Ala Leu
                565                 570                 575
Lys Ala Ala Leu Ala Asp Ser Leu Gln Arg Thr Ala Arg Asp Ala Glu
                580                 585                 590
Leu Gln Ser Tyr Glu Val Pro Ala Asp Phe Ile Val Glu Thr Glu Pro
            595                 600                 605
Phe Ser Ala Ala Asn Gly Leu Leu Ser Gly Val Gly Lys Leu Leu Arg
            610                 615                 620
Pro Asn Leu Lys Asp Arg Tyr Gly Gln Arg Leu Glu Gln Met Tyr Ala
625                 630                 635                 640
Asp Ile Ala Ala Thr Gln Ala Asn Gln Leu Arg Glu Leu Arg Arg Ala
                645                 650                 655
Ala Ala Thr Gln Pro Val Ile Asp Thr Leu Thr Gln Ala Ala Ala Thr
            660                 665                 670
Ile Leu Gly Thr Gly Ser Glu Val Ala Ser Asp Ala His Phe Thr Asp
            675                 680                 685
```

Leu Gly Gly Asp Ser Leu Ser Ala Leu Thr Leu Ser Asn Leu Leu Ser
690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
        725                 730                 735

Gly Asp Arg Arg Pro Ser Phe Thr Thr Val His Gly Ala Asp Ala Thr
        740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
            805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
        835                 840                 845

Asp Arg His Leu Arg Val Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
        915                 920                 925

Ala Met Gly Ile Pro Asp Phe Glu Glu Asp Gly Asp Ile Arg Thr Val
    930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
            965                 970                 975

Gly Leu Pro Val Ala Thr Phe Arg Ser Asp Met Ile Leu Ala His Pro
        980                 985                 990

Arg Tyr Arg Gly Gln Val Asn Val Pro Asp Met Phe Thr Arg Leu Leu
        995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
    1070                1075                1080

Pro Ile Asp Arg Val Asp Asp Tyr Asp Asp Trp Val Arg Arg Phe
    1085                1090                1095

Glu Thr Ala Leu Thr Ala Leu Pro Glu Lys Arg Arg Ala Gln Thr
    1100            1105                1110

Val Leu Pro Leu Leu His Ala Phe Arg Ala Pro Gln Ala Pro Leu
    1115            1120                1125

Arg Gly Ala Pro Glu Pro Thr Glu Val Phe His Ala Ala Val Arg
    1130            1135                1140

Thr Ala Lys Val Gly Pro Gly Asp Ile Pro His Leu Asp Glu Ala
    1145            1150                1155

Leu Ile Asp Lys Tyr Ile Arg Asp Leu Arg Glu Phe Gly Leu Ile
    1160            1165                1170

<210> SEQ ID NO 8
<211> LENGTH: 209
<212> TYPE: PRT
<213> ORGANISM: Escherichia coli

<400> SEQUENCE: 8

Met Val Asp Met Lys Thr Thr His Thr Ser Leu Pro Phe Ala Gly His
1               5                   10                  15

Thr Leu His Phe Val Glu Phe Asp Pro Ala Asn Phe Cys Glu Gln Asp
            20                  25                  30

Leu Leu Trp Leu Pro His Tyr Ala Gln Leu Gln His Ala Gly Arg Lys
        35                  40                  45

Arg Lys Thr Glu His Leu Ala Gly Arg Ile Ala Ala Val Tyr Ala Leu
    50                  55                  60

Arg Glu Tyr Gly Tyr Lys Cys Val Pro Ala Ile Gly Glu Leu Arg Gln
65                  70                  75                  80

Pro Val Trp Pro Ala Glu Val Tyr Gly Ser Ile Ser His Cys Gly Thr
                85                  90                  95

Thr Ala Leu Ala Val Val Ser Arg Gln Pro Ile Gly Ile Asp Ile Glu
            100                 105                 110

Glu Ile Phe Ser Val Gln Thr Ala Arg Glu Leu Thr Asp Asn Ile Ile
        115                 120                 125

Thr Pro Ala Glu His Glu Arg Leu Ala Asp Cys Gly Leu Ala Phe Ser
    130                 135                 140

Leu Ala Leu Thr Leu Ala Phe Ser Ala Lys Glu Ser Ala Phe Lys Ala
145                 150                 155                 160

Ser Glu Ile Gln Thr Asp Ala Gly Phe Leu Asp Tyr Gln Ile Ile Ser
                165                 170                 175

Trp Asn Lys Gln Gln Val Ile Ile His Arg Glu Asn Glu Met Phe Ala
            180                 185                 190

Val His Trp Gln Ile Lys Glu Lys Ile Val Ile Thr Leu Cys Gln His
        195                 200                 205

Asp

<210> SEQ ID NO 9
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 9
aaaaacagca acaatgtgag ctttgttgta attatattgt aaacatattg attccgggga    60
tccgtcgacc                                                          70

```
<210> SEQ ID NO 10
<211> LENGTH: 68
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
aaacggagcc tttcggctcc gttattcatt tacgcggctt caactttcct gtaggctgga    60
gctgcttc                                                              68

<210> SEQ ID NO 11
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
cgggcaggtg ctatgaccag gac                                             23

<210> SEQ ID NO 12
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
cgcggcgttg accggcagcc tgg                                             23

<210> SEQ ID NO 13
<211> LENGTH: 5659
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
atgatcatca aacctaaaat tcgtggattt atctgtacaa caacgcaccc agtgggttgt    60
gaagcgaacg taaaagaaca aattgcctac acaaaagcac aaggtccgat caaaaacgca   120
cctaagcgcg tgttggttgt cggatcgtct agcggctatg gtctgtcatc acgcatcgct   180
gcggcgtttg gcggtggtgc ggcgacgatc ggcgtatttt tcgaaaagcc gggcactgac   240
aaaaaaccag gtactgcggg tttctacaat gcagcagcgt ttgacaagct agcgcatgaa   300
gcgggcttgt acgcaaaaag cctgaacggc gatgcgttct cgaacgaagc gaagcaaaaa   360
gcgattgagc tgattaagca agacctcggc cagattgatt ggtggttta ctcgttggct   420 tctccagtgc gtaagatgcc agacacgggt gagctagtgc gctctgcact aaaaccgatc   480
ggcgaaacgt acacctctac cgcggtagat accaataaag atgtgatcat tgaagccagt   540
gttgaacctg cgaccgagca agaaatcgct gacactgtca ccgtgatggg cggtcaagat   600
tgggaactgt ggatccaagc actggaagag gcgggtgttc ttgctgaagg ttgcaaaacc   660
```

```
gtggcgtaca gctacatcgg tactgaattg acttggccaa tttactggga tggcgcttta    720
ggccgtgcca agatggacct agatcgcgca gcgacagcgc tgaacgaaaa gctggcagcg    780
aaaggtggta ccgcgaacgt tgcagttttg aaatcagtgg tgactcaagc aagctctgcg    840
attcctgtga tgccgctcta catcgcaatg gtgttcaaga agatgcgtga acagggcgtg    900
catgaaggct gtatggagca gatctaccgc atgttcagtc aacgtctgta caaagaagat    960
ggttcagcgc cggaagtgga tgatcacaat cgtctgcgtt tggatgactg ggaactgcgt   1020
gatgacattc agcagcactg ccgtgatctg tggccacaaa tcaccacaga gaacctgcgt   1080
gagctgaccg attacgacat gtacaaagaa gagttcatca agctgtttgg ctttggcatt   1140
gaaggcattg attacgatgc tgacgtcaat ccagaagtcg aatttgatgt gattgatatc   1200
gagtaattta gtgactgagc gtacatgtat acgaagatta ttggtactgg cagctatctg   1260
cccgaacaag tgcggactaa cgccgatctg gaaaaaatgg ttgagacctc tgacgagtgg   1320
attgtcactc gtacaggtat tcgtaaacgc catatcgccg cgccgaatga aactgtcgcg   1380
acgatgggct ttaccgctgc gaatcgcgcg attgagatgc ggggatcga taaagaccaa   1440
attggcttga ttgtggtggc taccacatca gcaacgcatg catttccaag cgcggcatgt   1500
cagattcaaa gtatgctcgg tattaaaggt tgcccggcgt ttgatgtcgc ggcagcgtgc   1560
gcaggtttca cctacgcgtt aagcatcgcc gaccagtacg ttaaatccgg cgcggttaaa   1620
cacgcgctgg tggtcggttc cgatgtatta gcccgcactt gcgatcctgg cgatcgcggt   1680
acgatcatta ttttcggcga tggcgcaggc gcggccgtac tgagcgcttc tgaagaaccg   1740
ggtattatct ccactcatct tcatgccgat ggccgttacg tgaattact gaccctgccg   1800
aatgccgatc gcgtaaatcc ggataacccg atttacctga caatggcggg caatgaagtc   1860
tttaaagtgg cggtcactga actggcgcat attgtcgatg agacgctggc ggctaataac   1920
ctggatcgct cagaactcga ttggctggtg ccgcatcagg ctaacctgcg tatcattagc   1980
gcgacagcga aaaactcgg catgtcgatg gacaatgtcg tcgtcacgct ggacaggcac   2040
ggcaatacct ccgcggcttc tgtgccgtgc gcgctggatg aagccgtgcg tgacgggcga   2100
attaaagccg gtcagctggt attgcttgaa gccttcgggg gtggattcac ctggggctcc   2160
gcgctgattc gtttctagta taaggattta acatgacgc aatttgcatt tgtgttcccc   2220
ggtcagggtt ctcagagcgt tgggatgttg gccgagatgg cggcaaatta ccctatcgta   2280
gaagaaacgt ttgctgaagc ttctgcggct ctgggatatg atctgtgggc gctcacccag   2340
caaggtccag cggaagaact gaataaaacc tggcagacgc agccggcgtt attaaccgct   2400
tccgtcgcgc tttggcgcgt ttggcagcag cagggcggta aaatgcctgc gttaatggca   2460
ggtcacagcc tggcgaata ttccgcgctg gtttgcgctg gcgtcatcaa ctttgctgat   2520
gccgttcgtc tggtggaaat gcgcgtaaa ttcatgcagg aagcggttcc ggaaggcact   2580
ggcggcatgt ctgcgatcat cgggctggat gatgcctcta ttgctaaagc ctgtgaagaa   2640
tctgccgaag gcaggttgt ttcgccggtt aactttaact cgccgggaca ggtggttatc   2700
gccgggcata agaggcggt agaacgtgcg ggcgcagcct gtaaagccgc tggcgcgaaa   2760
cgcgcgctgc cgctgccggt gagcgtaccg tcgcactgcg cgctgatgaa ccagcggca   2820
gataagctgg cggttgaatt agccaaaatt acctttagcg cgccaacggt gccggtagtg   2880
aacaacgttg acgtgaaatg tgaaccgat gccgccgcta ccgcgatgc gctggttcgc   2940
cagttgtaca atccggtaca gtggacgaag agcgtggaat ttatcgcggc gcagggcgtt   3000
gaacatcttt atgaagtggg tccaggtaaa gtcctcactg gtctgacgaa acgtattgtc   3060
```

-continued

```
gacaccctga cagcgtcggc gctgaacgag ccggcggcgc tgtctgcggc acttacgcaa    3120
taaaagagga aaaccatgag ctttgaagga aagattgcgc tggtgactgg tgcaagccgt    3180
ggcataggcc gcgcaattgc agagactctc gttgcccgcg gcgcgaaagt tatcgggact    3240
gcgaccagtg aaaatggtgc gaagaacatt agcgactatt taggtgctaa cgggaaaggt    3300
ttgatgttga atgtgaccga tcctgcatct attgaatctg ttctggaaaa tattcgcgca    3360
gaatttggtg aagtggatat cctggttaat aatgccggta tcactcgtga taatctgttg    3420
atgcgaatga aagatgatga gtggaacgat attatcgaaa ccaacttatc atccgttttc    3480
cgcctgtcaa aagcggtaat gcgcgctatg atgaaaaagc gttgtggtcg cattatcact    3540
attggttctg tggttggtac catgggaaat gcaggtcagg caaactacgc tgcggcgaaa    3600
gcgggcctga tcggtttcag taaatcactg gcgcgtgaag ttgcgtcccg tggtattact    3660
gtcaatgttg tggctccggg ttttattgaa acggacatga cgcgtgcgct gtctgacgat    3720
cagcgtgcgg gtatcctggc gcaggtgcct gcgggtcgcc tcggcggcgc tcaggaaatc    3780
gccagtgcgg ttgcattttt agcctctgac gaagcgagtt acatcactgg tgagactctg    3840
cacgtcaacg gcggaatgta catggtttaa ttttaaggtt tacataaaac atggtagata    3900
aacgcgaatc ctatacaaaa gaagaccttc ttgcctctgg tcgtggtgaa ctgtttggcg    3960
ctaaagggcc gcaactccct gcaccgaaca tgctgatgat ggaccgcgtc gttaagatga    4020
ccgaaacggg cggcaatttc gacaaaggct atgtcgaagc cgagctggat atcaatccgg    4080
atctatggtt cttcggatgc cactttatcg gcgatccggt gatgcccggt tgtctgggtc    4140
tggatgctat gtggcaattg gtgggattct acctgggctg gttgggcggc gaaggcaaag    4200
gccgcgctct gggcgtgggc gaagtgaaat ttaccggcca ggttctgccg acagccagga    4260
aagtcaccta tcgtattcat ttcaaacgta tcgtaaaccg tcgcctgatc atgggcctgg    4320
cggacggtga ggttctggtg gatggtcgcc tgatctatac cgcacacgat ttgaaagtcg    4380
gtttgttcca ggatacttcc gcgttctaaa aggaggcaac aaaatgaatc gccgcgttgt    4440
cattacgggt attggtgcag tgacgccggt gggtaacaac gctgatagct tctggtgcag    4500
catcaaagag ggtaaatgtg gcattgacaa gatcaaagcg tttgacgcaa ccgatttcaa    4560
agttaagctg gctgccgaag tgaaggactt caccccggag gactttatcg acaagcgtga    4620
ggcgaaccgt atggaccgtt ttagccagtt tgcgatcgtt gcggcggatg aggcaatcaa    4680
ggacagcaaa ctggacctgg agtcgattga taagaatcgt ttcggcgtca ttgttggtag    4740
cggcattggc ggcatcggca ccattgagaa gcaggatgaa aagctgatta ccaaaggtcc    4800
gggtcgtgtg agccctatga ctattccgat gatcattgcg aatatggcaa gcggtaatct    4860
ggcgattcgt tatggcgcta aaggtatttg cacgaccatt gtcaccgcat gtgcgagcgc    4920
gaacaacagc attggtgagt ccttccgtaa cattaagttt ggttatagcg acgttatgat    4980
ctctggtggt agcgaagcag gtatcacccc gttgagcctg gcgggttttg cctcgatgaa    5040
ggccgtgacc aaatctgagg acccgaagcg cgccagcatc ccgttcgata aggatcgcag    5100
cggttttgtg atgggcgagg gcagcggtat cgttatcttg aaagagttgg agcacgcgct    5160
gaagcgtggt gccaaaatct atgccgagat cgttggctat ggtgcgacct gcgacgcata    5220
tcatatcacg agcccagcgc cgaatggtga aggtggtgca cgtgcaatga aactggcaat    5280
ggaagaagat aatgtccgcc cagaggacat ttcctatatc aacgcgcacg gtacgagcac    5340
ggcgtacaat gacagcttcg aaacccaagc gatcaagacg gtcctgggtg aatacgccta    5400
```

```
caaagtgccg gtgtctagca ccaagagcat gaccggccac ctgctgggcg ctggcggtgc    5460
agtcgaagcg attatctgtg ccaaagctat tgaagagggt ttcattccgc cgaccatcgg    5520
ctacaaagag gcggatccgg aatgcgacct ggattacgtt cctaacgagg gccgtaatgc    5580
agaagtcaac tacgttctgt ccaacagcct gggcttcggt ggccataatg cgactctgct    5640
gttcaaaaag tacaaatga                                                 5659
```

<210> SEQ ID NO 14
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14

```
gcagttattg gtgcccttaa acgcctggtt gctacgcctg                            40
```

<210> SEQ ID NO 15
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15

```
gagccaatat gcgagaacac ccgagaa                                         27
```

<210> SEQ ID NO 16
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16

```
cgctgaacgt attgcaggcc gagttgctgc accgctcccg ccaggcag                  48
```

<210> SEQ ID NO 17
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17

```
ggaattgcca cggtgcggca ggctccatac gcgaggccag gttatccaac g              51
```

<210> SEQ ID NO 18
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18

```
aatcaccagc actaaagtgc gcggttcgtt acccg                                35
```

<210> SEQ ID NO 19
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
atctgccgtg gattgcagag tctattcagc tacg                          34

<210> SEQ ID NO 20
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
gcaattccat atgacgagcg atgttcacga                               30

<210> SEQ ID NO 21
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ccgctcgagt aaatcagacc gaactcgcg                                29

<210> SEQ ID NO 22
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
atgggcagca gccatcatca tcatcatcac agcagcggcc tggtgccgcg cggcagccat    60

<210> SEQ ID NO 23
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
acggatcccc ggaatgcgca acgcaattaa tgtaagttag cgc                43

<210> SEQ ID NO 24
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 24
tgcgtcatcg ccattgaatt cctaaatcag accgaactcg cgcagg            46

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
attccgggga tccgtcgacc                                         20

<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
aatggcgatg acgcatcctc acg                                     23

<210> SEQ ID NO 27
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
acggaaagga gctagcacat gggcagcagc catcatcat                    39

<210> SEQ ID NO 28
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
gtaaaggatg gacggcggtc acccgcc                                 27

<210> SEQ ID NO 29
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
cacggcgggt gaccgccgtc catcc                                   25

<210> SEQ ID NO 30
<211> LENGTH: 43

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
ttaattccgg ggatccctaa atcagaccga actcgcgcag gtc                    43

<210> SEQ ID NO 31
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
cagccgttta ttgccgactg gatg                                        24

<210> SEQ ID NO 32
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
ctgttttatc agaccgcttc tgcgttc                                     27

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
gcactcgacc ggaattatcg                                             20

<210> SEQ ID NO 34
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
gcactacgcg tactgtgagc cagag                                       25

<210> SEQ ID NO 35
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
```
gaggaataaa ccatgacgag cgatgttcac gacgcgaccg acggc                    45

<210> SEQ ID NO 36
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
ctaaatcaga ccgaactcgc gcagg                                          25

<210> SEQ ID NO 37
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
catggtttat tcctccttat ttaatcgata c                                   31

<210> SEQ ID NO 38
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
tgacctgcgc gagttcggtc tgatttag                                       28

<210> SEQ ID NO 39
<211> LENGTH: 1168
<212> TYPE: PRT
<213> ORGANISM: Mycobacterium smegmatis

<400> SEQUENCE: 39

Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala
                20                  25                  30

Ile Ser Ala Ala Ala Ala Asp Pro Glu Leu Arg Leu Pro Ala Ala Val
            35                  40                  45

Lys Gln Ile Leu Ala Gly Tyr Ala Asp Arg Pro Ala Leu Gly Lys Arg
        50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
        115                 120                 125

Ile Ala Leu Leu Glu Leu Gly Ala Val Ser Val Pro Leu Gln Thr Ser
    130                 135                 140

```
Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
            165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
            195                 200                 205

Ala Gly Thr Gly Val Val Glu Thr Ile Thr Asp Ala Leu Asp Arg
    210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
            245                 250                 255

Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
            275                 280                 285

Leu Asn Phe Met Pro Met Ser His Val Met Gly Arg Gly Ile Leu Cys
    290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
            325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
            355                 360                 365

Ala Val Leu Glu Glu Val Arg Thr Gln Leu Leu Gly Gly Arg Phe Val
    370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
            405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
            435                 440                 445

Asp Arg Pro Tyr Pro Arg Gly Glu Leu Leu Val Lys Ser Glu Gln Met
450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
            485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
            515                 520                 525

Ser Pro Leu Val Arg Gln Ile Tyr Val Tyr Gly Asn Ser Ala Arg Ser
            530                 535                 540

Tyr Leu Leu Ala Val Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
```

-continued

```
                565                 570                 575
Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
            595                 600                 605

Arg Lys Leu Ala Arg Pro Lys Leu Lys Ala His Tyr Gly Glu Arg Leu
610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
            645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
            675                 680                 685

Phe Ser Asn Leu Leu His Glu Ile Phe Asp Val Asp Val Pro Val Gly
            690                 695                 700

Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
            725                 730                 735

Gly Arg Asp Ala Thr Glu Val Arg Ala Arg Asp Leu Ala Leu Gly Lys
            740                 745                 750

Phe Ile Asp Ala Lys Thr Leu Ser Ala Pro Gly Leu Pro Arg Ser
            755                 760                 765

Gly Thr Glu Ile Arg Thr Val Leu Leu Thr Gly Ala Thr Gly Phe Leu
770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
            805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
            835                 840                 845

Lys Gly Glu Ala Asp Leu Gly Leu Asp His Asp Thr Trp Gln Arg Leu
850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
            885                 890                 895

Glu Leu Ile Arg Ile Ala Leu Thr Thr Ile Lys Pro Tyr Val Tyr
            900                 905                 910

Val Ser Thr Ile Gly Val Gly Gln Ile Ser Pro Glu Ala Phe Val
            915                 920                 925

Glu Asp Ala Asp Ile Arg Glu Ile Ser Ala Thr Arg Arg Val Asp Asp
            930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
            965                 970                 975

Cys Asp Met Ile Leu Ala Asp Thr Thr Tyr Ser Gly Gln Leu Asn Leu
            980                 985                 990
```

```
Pro Asp Met Phe Thr Arg Leu Met  Leu Ser Leu Val Ala  Thr Gly Ile
       995                 1000                1005

Ala Pro Gly Ser Phe Tyr Glu  Leu Asp Ala Asp Gly  Asn Arg Gln
  1010                1015                 1020

Arg Ala His Tyr Asp Gly Leu  Pro Val Glu Phe Ile  Ala Glu Ala
  1025                1030                 1035

Ile Ser Thr Ile Gly Ser Gln  Val Thr Asp Gly Phe  Glu Thr Phe
  1040                1045                 1050

His Val Met Asn Pro Tyr Asp  Asp Gly Ile Gly Leu  Asp Glu Tyr
  1055                1060                 1065

Val Asp Trp Leu Ile Glu Ala  Gly Tyr Pro Val His  Arg Val Asp
  1070                1075                 1080

Asp Tyr Ala Thr Trp Leu Ser  Arg Phe Glu Thr Ala  Leu Arg Ala
  1085                1090                 1095

Leu Pro Glu Arg Gln Arg Gln  Ala Ser Leu Leu Pro  Leu Leu His
  1100                1105                 1110

Asn Tyr Gln Gln Pro Ser Pro  Pro Val Cys Gly Ala  Met Ala Pro
  1115                1120                 1125

Thr Asp Arg Phe Arg Ala Ala  Val Gln Asp Ala Lys  Ile Gly Pro
  1130                1135                 1140

Asp Lys Asp Ile Pro His Val  Thr Ala Asp Val Ile  Val Lys Tyr
  1145                1150                 1155

Ile Ser Asn Leu Gln Met Leu  Gly Leu Leu
  1160                1165

<210> SEQ ID NO 40
<211> LENGTH: 1168
<212> TYPE: PRT
<213> ORGANISM: Mycobacterium tuberculosis

<400> SEQUENCE: 40

Met Ser Ile Asn Asp Gln Arg Leu Thr Arg Arg Val Glu Asp Leu Tyr
 1               5                  10                  15

Ala Ser Asp Ala Gln Phe Ala Ala Ala Ser Pro Asn Glu Ala Ile Thr
            20                  25                  30

Gln Ala Ile Asp Gln Pro Gly Val Ala Leu Pro Gln Leu Ile Arg Met
         35                  40                  45

Val Met Glu Gly Tyr Ala Asp Arg Pro Ala Leu Gly Gln Arg Ala Leu
    50                  55                  60

Arg Phe Val Thr Asp Pro Asp Ser Gly Arg Thr Met Val Glu Leu Leu
65                  70                  75                  80

Pro Arg Phe Glu Thr Ile Thr Tyr Arg Glu Leu Trp Ala Arg Ala Gly
                85                  90                  95

Thr Leu Ala Thr Ala Leu Ser Ala Glu Pro Ala Ile Arg Pro Gly Asp
            100                 105                 110

Arg Val Cys Val Leu Gly Phe Asn Ser Val Asp Tyr Thr Thr Ile Asp
         115                 120                 125

Ile Ala Leu Ile Arg Leu Gly Ala Val Ser Val Pro Leu Gln Thr Ser
     130                 135                 140

Ala Pro Val Thr Gly Leu Arg Pro Ile Val Thr Glu Thr Glu Pro Thr
145                 150                 155                 160

Met Ile Ala Thr Ser Ile Asp Asn Leu Gly Asp Ala Val Glu Val Leu
                165                 170                 175

Ala Gly His Ala Pro Ala Arg Leu Val Val Phe Asp Tyr His Gly Lys
```

```
                180             185             190
Val Asp Thr His Arg Glu Ala Val Glu Ala Arg Ala Arg Leu Ala
            195             200             205
Gly Ser Val Thr Ile Asp Thr Leu Ala Glu Leu Ile Glu Arg Gly Arg
        210             215             220
Ala Leu Pro Ala Thr Pro Ile Ala Asp Ser Ala Asp Ala Leu Ala
225             230             235             240
Leu Leu Ile Tyr Thr Ser Gly Ser Thr Gly Ala Pro Lys Gly Ala Met
            245             250             255
Tyr Arg Glu Ser Gln Val Met Ser Phe Trp Arg Lys Ser Ser Gly Trp
        260             265             270
Phe Glu Pro Ser Gly Tyr Pro Ser Ile Thr Leu Asn Phe Met Pro Met
        275             280             285
Ser His Val Gly Gly Arg Gln Val Leu Tyr Gly Thr Leu Ser Asn Gly
        290             295             300
Gly Thr Ala Tyr Phe Val Ala Lys Ser Asp Leu Ser Thr Leu Phe Glu
305             310             315             320
Asp Leu Ala Leu Val Arg Pro Thr Glu Leu Cys Phe Val Pro Arg Ile
            325             330             335
Trp Asp Met Val Phe Ala Glu Phe His Ser Glu Val Asp Arg Arg Leu
        340             345             350
Val Asp Gly Ala Asp Arg Ala Ala Leu Glu Ala Gln Val Lys Ala Glu
        355             360             365
Leu Arg Glu Asn Val Leu Gly Gly Arg Phe Val Met Ala Leu Thr Gly
        370             375             380
Ser Ala Pro Ile Ser Ala Glu Met Thr Ala Trp Val Glu Ser Leu Leu
385             390             395             400
Ala Asp Val His Leu Val Glu Gly Tyr Gly Ser Thr Glu Ala Gly Met
            405             410             415
Val Leu Asn Asp Gly Met Val Arg Arg Pro Ala Val Ile Asp Tyr Lys
            420             425             430
Leu Val Asp Val Pro Glu Leu Gly Tyr Phe Gly Thr Asp Gln Pro Tyr
        435             440             445
Pro Arg Gly Glu Leu Leu Val Lys Thr Gln Thr Met Phe Pro Gly Tyr
        450             455             460
Tyr Gln Arg Pro Asp Val Thr Ala Glu Val Phe Asp Pro Asp Gly Phe
465             470             475             480
Tyr Arg Thr Gly Asp Ile Met Ala Lys Val Gly Pro Asp Gln Phe Val
            485             490             495
Tyr Leu Asp Arg Arg Asn Asn Val Leu Lys Leu Ser Gln Gly Glu Phe
        500             505             510
Ile Ala Val Ser Lys Leu Glu Ala Val Phe Gly Asp Ser Pro Leu Val
        515             520             525
Arg Gln Ile Phe Ile Tyr Gly Asn Ser Ala Arg Ala Tyr Pro Leu Ala
        530             535             540
Val Val Val Pro Ser Gly Asp Ala Leu Ser Arg His Gly Ile Glu Asn
545             550             555             560
Leu Lys Pro Val Ile Ser Glu Ser Leu Gln Glu Val Ala Arg Ala Ala
            565             570             575
Gly Leu Gln Ser Tyr Glu Ile Pro Arg Asp Phe Ile Ile Glu Thr Thr
        580             585             590
Pro Phe Thr Leu Glu Asn Gly Leu Leu Thr Gly Ile Arg Lys Leu Ala
        595             600             605
```

-continued

```
Arg Pro Gln Leu Lys Lys Phe Tyr Gly Glu Arg Leu Glu Arg Leu Tyr
    610             615                 620

Thr Glu Leu Ala Asp Ser Gln Ser Asn Glu Leu Arg Glu Leu Arg Gln
625             630                 635                 640

Ser Gly Pro Asp Ala Pro Val Leu Pro Thr Leu Cys Arg Ala Ala Ala
                645                 650                 655

Ala Leu Leu Gly Ser Thr Ala Ala Asp Val Arg Pro Asp Ala His Phe
                660                 665                 670

Ala Asp Leu Gly Gly Asp Ser Leu Ser Ala Leu Ser Leu Ala Asn Leu
            675                 680                 685

Leu His Glu Ile Phe Gly Val Asp Val Pro Val Gly Val Ile Val Ser
    690                 695                 700

Pro Ala Ser Asp Leu Arg Ala Leu Ala Asp His Ile Glu Ala Ala Arg
705             710                 715                 720

Thr Gly Val Arg Arg Pro Ser Phe Ala Ser Ile His Gly Arg Ser Ala
                725                 730                 735

Thr Glu Val His Ala Ser Asp Leu Thr Leu Asp Lys Phe Ile Asp Ala
                740                 745                 750

Ala Thr Leu Ala Ala Ala Pro Asn Leu Pro Ala Pro Ser Ala Gln Val
    755                 760                 765

Arg Thr Val Leu Leu Thr Gly Ala Thr Gly Phe Leu Gly Arg Tyr Leu
    770                 775                 780

Ala Leu Glu Trp Leu Asp Arg Met Asp Leu Val Asn Gly Lys Leu Ile
785             790                 795                 800

Cys Leu Val Arg Ala Arg Ser Asp Glu Glu Ala Gln Ala Arg Leu Asp
                805                 810                 815

Ala Thr Phe Asp Ser Gly Asp Pro Tyr Leu Val Arg His Tyr Arg Glu
                820                 825                 830

Leu Gly Ala Gly Arg Leu Glu Val Leu Ala Gly Asp Lys Gly Glu Ala
            835                 840                 845

Asp Leu Gly Leu Asp Arg Val Thr Trp Gln Arg Leu Ala Asp Thr Val
    850                 855                 860

Asp Leu Ile Val Asp Pro Ala Ala Leu Val Asn His Val Leu Pro Tyr
865             870                 875                 880

Ser Gln Leu Phe Gly Pro Asn Ala Ala Gly Thr Ala Glu Leu Leu Arg
                885                 890                 895

Leu Ala Leu Thr Gly Lys Arg Lys Pro Tyr Ile Tyr Thr Ser Thr Ile
            900                 905                 910

Ala Val Gly Glu Gln Ile Pro Pro Glu Ala Phe Thr Glu Asp Ala Asp
    915                 920                 925

Ile Arg Ala Ile Ser Pro Thr Arg Arg Ile Asp Asp Ser Tyr Ala Asn
    930                 935                 940

Gly Tyr Ala Asn Ser Lys Trp Ala Gly Glu Val Leu Leu Arg Glu Ala
945             950                 955                 960

His Glu Gln Cys Gly Leu Pro Val Thr Val Phe Arg Cys Asp Met Ile
                965                 970                 975

Leu Ala Asp Thr Ser Tyr Thr Gly Gln Leu Asn Leu Pro Asp Met Phe
                980                 985                 990

Thr Arg Leu Met Leu Ser Leu Ala Ala Thr Gly Ile Ala Pro Gly Ser
            995                 1000                1005

Phe Tyr Glu Leu Asp Ala His Gly Asn Arg Gln Arg Ala His Tyr
    1010                1015                1020
```

```
Asp Gly Leu Pro Val Glu Phe Val Ala Glu Ala Ile Cys Thr Leu
    1025            1030            1035

Gly Thr His Ser Pro Asp Arg Phe Val Thr Tyr His Val Met Asn
    1040            1045            1050

Pro Tyr Asp Asp Gly Ile Gly Leu Asp Glu Phe Val Asp Trp Leu
    1055            1060            1065

Asn Ser Pro Thr Ser Gly Ser Gly Cys Thr Ile Gln Arg Ile Ala
    1070            1075            1080

Asp Tyr Gly Glu Trp Leu Gln Arg Phe Glu Thr Ser Leu Arg Ala
    1085            1090            1095

Leu Pro Asp Arg Gln Arg His Ala Ser Leu Leu Pro Leu Leu His
    1100            1105            1110

Asn Tyr Arg Glu Pro Ala Lys Pro Ile Cys Gly Ser Ile Ala Pro
    1115            1120            1125

Thr Asp Gln Phe Arg Ala Ala Val Gln Glu Ala Lys Ile Gly Pro
    1130            1135            1140

Asp Lys Asp Ile Pro His Leu Thr Ala Ala Ile Ile Ala Lys Tyr
    1145            1150            1155

Ile Ser Asn Leu Arg Leu Leu Gly Leu Leu
    1160            1165
```

<210> SEQ ID NO 41
<211> LENGTH: 3507
<212> TYPE: DNA
<213> ORGANISM: Mycobacterium smegmatis

<400> SEQUENCE: 41

```
atgacgatcg aaacgcgcga agaccgcttc aaccggcgca ttgaccactt gttcgaaacc      60
gacccgcagt cgccgccgc ccgtcccgac gaggcgatca gcgcggctgc cgccgatccg     120
gagttgcgcc ttcctgccgc ggtcaaacag attctggccg gctatgcgga ccgccctgcg     180
ctgggcaagc gcgccgtcga gttcgtcacc gacgaagaag ccgcaccac cgcgaagctc     240
ctgccccgct tcgacaccat cacctaccgt cagctcgcag gccggatcca ggccgtgacc     300
aatgcctggc acaaccatcc ggtgaatgcc ggtgaccgcg tggccatcct gggtttcacc     360
agtgtcgact acacgacgat cgacatcgcc ctgctcgaac tcggcgccgt gtccgtaccg     420
ctgcagacca gtgcgccggt ggcccaactg cagccgatcg tcgccgagac cgagcccaag     480
gtgatcgcgt cgagcgtcga cttcctcgcc gacgcagtcg ctctcgtcga gtccgggccc     540
gcgccgtcgc gactggtggt gttcgactac agccacgagg tcgacgatca gcgtgaggcg     600
ttcgaggcgg ccaagggcaa gctcgcaggc accggcgtcg tcgtcgagac gatcaccgac     660
gcactggacc gcgggcggtc actcgccgac gcaccgctct acgtgcccga cgaggccgac     720
ccgctgaccc ttctcatcta cacctccggc agcaccggca ctcccaaggg cgcgatgtac     780
cccgagtcca agaccgccac gatgtggcag gccgggtcca aggcccggtg ggacgagacc     840
ctcggcgtga tgccgtcgat cacctgaac ttcatgccca tgagtcacgt catggggcgc     900
ggcatcctgt gcagcacact cgccagcggc ggaaccgcgt acttcgccgc acgcagcgac     960
ctgtccacct tcctggagga cctcgcctc gtgcggccca cgcagctcaa cttcgttcct    1020
cgcatctggg acatgctgtt ccaggagtac cagagccgcc tcgacaaccg ccgcgccgag    1080
ggatccgagg accgagccga agccgcagtc ctcgaagagg tccgcacccca actgctcggc    1140
gggcgattcg tttcggccct gaccggatcg gctcccatct cggcggagat gaagagctgg    1200
gtcgaggacc tgctcgacat gcatctgctg gagggctacg gctccaccga ggccggcgcg    1260
```

```
gtgttcatcg acgggcagat ccagcgcccg ccggtcatcg actacaagct ggtcgacgtg   1320
cccgatctcg gctacttcgc cacgaccgg ccctacccgc gcggcgaact tctggtcaag    1380
tccgagcaga tgttccccgg ctactacaag cgtccggaga tcaccgccga gatgttcgac   1440
gaggacgggt actaccgcac cggcgacatc gtcgccgagc tcgggcccga ccatctcgaa   1500
tacctcgacc gccgcaacaa cgtgctgaaa ctgtcgcagg gcgaattcgt cacggtctcc   1560
aagctggagg cggtgttcgg cgacagcccc ctggtacgcc agatctacgt ctacggcaac   1620
agcgcgcggt cctatctgct ggcggtcgtg gtcccgaccg aagaggcact gtcacgttgg   1680
gacggtgacg aactcaagtc gcgcatcagc gactcactgc aggacgcggc acgagccgcc   1740
ggattgcagt cgtatgagat cccgcgtgac ttcctcgtcg acaacacc tttcacgctg    1800 gagaacggcc tgctgaccgg tatccgcaag ctggcccggc cgaaactgaa ggcgcactac   1860
ggcgaacgcc tcgaacagct ctacaccgac ctggccgagg gcaggccaa cgagttgcgc    1920 gagttgcgcc gcaacggagc cgaccggccc gtgtcgaga ccgtcagccg cgccgcggtc    1980
gcactgctcg gtgcctccgt cacggatctg cggtccgatg cgcacttcac cgatctgggt   2040
ggagattcgt tgtcggcctt gagcttctcg aacctgttgc acgagatctt cgatgtcgac   2100
gtgccggtcg gcgtcatcgt cagcccggcc accgacctgg caggcgtcgc ggcctacatc   2160
gagggcgaac tgcgcggctc caagcgcccc acatacgcgt cggtgcacgg gcgcgacgcc   2220
accgaggtgc gcgcgcgtga tctcgccctg gcaagttca tcgacgccaa gaccctgtcc    2280
gccgcgccgg gtctgccgcg ttcgggcacc gagatccgca ccgtgctgct gaccggcgcc   2340
accgggttcc tgggccgcta tctggcgctg gaatggctgg agcgcatgga cctggtggac   2400
ggcaaggtga tctgcctggt gcgcgcccgc agcgacgacg aggcccgggc gcgtctggac   2460
gccacgttcg acaccgggga cgcgacactg ctcgagcact accgcgcgct ggcagccgat   2520
cacctcgagg tgatcgccgg tgacaagggc gaggccgatc tgggtctcga ccacgacacg   2580
tggcagcgac tggccgacac cgtcgatctg atcgtcgatc cggccgccct ggtcaatcac   2640
gtcctgccgt acagccagat gttcggaccc aatgcgctcg gcaccgccga actcatccgg   2700
atcgcgctga ccaccacgat caagccgtac gtgtacgtct cgacgatcgg tgtgggacag   2760
ggcatctccc ccgaggcgtt cgtcgaggac gccgacatcc gcgagatcag cgcgacgcgc   2820
cgggtcgacg actcgtacgc caacggctac ggcaacagca gtgggccgg cgaggtcctg    2880 ctgcgggagg cgcacgactg gtgtggtctg ccggtctcgg tgttccgctg cgacatgatc   2940
ctggccgaca cgacctactc gggtcagctg aacctgccgg acatgttcac ccgcctgatg   3000
ctgagcctcg tggcgaccgg catcgcgccc ggttcgttct acgaactcga tgcggacggc   3060
aaccggcagc gcgcccacta cgacgggctg cccgtggagt tcatcgccga ggcgatctcc   3120
accatcggct cgcaggtcac cgacggattc gagacgttcc acgtgatgaa cccgtacgac   3180
gacggcatcg gcctcgacga gtacgtggac tggctgatcg aggccggcta ccccgtgcac   3240
cgcgtcgacg actacgccac ctggctgagc cggttcgaaa ccgcactgcg ggccctgccg   3300
gaacggcaac gtcaggcctc gctgctgccg ctgctgcaca actatcagca gccctcaccg   3360
cccgtgtgcg gtgccatggc acccaccgac cggttccgtg ccgcggtgca ggacgcgaag   3420
atcggccccg acaaggacat tccgcacgtc acggccgacg tgatcgtcaa gtacatcagc   3480
aacctgcaga tgctcggatt gctgtaa                                       3507
```

<210> SEQ ID NO 42

<211> LENGTH: 3507
<212> TYPE: DNA
<213> ORGANISM: Mycobacterium tuberculosis

<400> SEQUENCE: 42

```
atgtcgatca acgatcagcg actgacacgc cgcgtcgagg acctatacgc cagcgacgcc     60
cagttcgccg ccgccagtcc caacgaggcg atcacccagg cgatcgacca gcccggggtc    120
gcgcttccac agctcatccg tatggtcatg gagggctacg ccgatcggcc ggcactcggc    180
cagcgtgcgc tccgcttcgt caccgacccc gacagcggcc gcaccatggt cgagctactg    240
ccgcggttcg agaccatcac ctaccgcgaa ctgtgggccc gcgccggcac attggccacc    300
gcgttgagcg ctgagcccgc gatccggccg ggcgaccggg tttgcgtgct gggcttcaac    360
agcgtcgact acacaaccat cgacatcgcg ctgatccggt tgggcgccgt gtcggttcca    420
ctgcagacca gtgcgccggt caccgggttg cgcccgatcg tcaccgagac cgagccgacg    480
atgatcgcca ccagcatcga caatcttggc gacgccgtcg aagtgctggc cggtcacgcc    540
ccggcccggc tggtcgtatt cgattaccac ggcaaggttg acacccaccg cgaggccgtc    600
gaagccgccc gagctcggtt ggccggctcg gtgaccatcg acacacttgc cgaactgatc    660
gaacgcggca gggcgctgcc ggccacaccc attgccgaca gcgccgacga cgcgctggcg    720
ctgctgattt acacctcggg tagtaccggc gcacccaaag gcgccatgta tcgcgagagc    780
caggtgatga gcttctggcg caagtcgagt ggctggttcg agccgagcgg ttacccctcg    840
atcacgctga acttcatgcc gatgagccac gtcgggggcc gtcaggtgct ctacgggacg    900
ctttccaacg gcggtaccgc ctacttcgtc gccaagagcg acctgtcgac gctgttcgag    960
gacctcgccc tggtgcggcc cacagaattg tgcttcgtgc cgcgcatctg ggacatggtg   1020
ttcgcagagt tccacagcga ggtcgaccgc cgcttggtgg acggcgccga tcgagcggcg   1080
ctggaagcgc aggtgaaggc cgagctgcgg gagaacgtgc tcggcggacg gtttgtcatg   1140
gcgctgaccg gttccgcgcc gatctccgct gagatgacgg cgtgggtcga gtccctgctg   1200
gccgacgtgc atttggtgga gggttacggc tccaccgagg ccgggatggt cctgaacgac   1260
ggcatggtgc ggcgccccgc ggtgatcgac tacaagctgg tcgacgtgcc cgagctgggc   1320
tacttcggca ccgatcagcc ctacccccgg ggcgagctgc tggtcaagac gcaaaccatg   1380
ttccccggct actaccagcg cccggatgtc accgccgagg tgttcgaccc cgacggcttc   1440
taccggaccg gggacatcat ggccaaagta ggccccgacc agttcgtcta cctcgaccgc   1500
cgcaacaacg tgctaaagct ctcccagggc gagttcatcg ccgtgtcgaa gctcgaggcg   1560
gtgttcggcg acagcccgct ggtccgacag atcttcatct acggcaacag tgcccgggcc   1620
tacccgctgg cggtggttgt cccgtccggg gacgcgcttt ctcgccatgg catcgagaat   1680
ctcaagcccg tgatcagcga gtccctgcag gaggtagcga gggcggccgg cctgcaatcc   1740
tacgagattc cacgcgactt catcatcgaa accacgccgt tcaccctgga gaacggcctg   1800
ctcaccggca tccgcaagct ggcacgcccg cagttgaaga agttctatgg cgaacgtctc   1860
gagcggctct ataccgagct ggccgatagc caatccaacg agctgcgcga gctgcggcaa   1920
agcggtcccg atgcgccggt gcttccgacg ctgtgccgtg ccgcggctgc gttgctgggc   1980
tctaccgctg cggatgtgcg gccggacgcg cacttcgccg acctgggtgg tgactcgctc   2040
tcggcgctgt cgttggccaa cctgctgcac gagatcttcg gcgtcgacgt gccggtgggt   2100
gtcattgtca gcccggcaag cgacctgcgg gccctggccg accacatcga agcagcgcgc   2160
accggcgtca ggcgacccag cttcgcctcg atacacggtc gctccgcgac ggaagtgcac   2220
```

```
gccagcgacc tcacgctgga caagttcatc gacgctgcca ccctggccgc agccccgaac    2280
ctgccggcac cgagcgccca agtgcgcacc gtactgctga ccggcgccac cggcttttg     2340 ggtcgctacc tggcgctgga atggctcgac cgcatggacc tggtcaacgg caagctgatc    2400
tgcctggtcc gcgccagatc cgacgaggaa gcacaagccc ggctggacgc gacgttcgat    2460
agcggcgacc cgtatttggt gcggcactac cgcgaattgg gcgccggccg cctcgaggtg    2520
ctcgccggcg acaagggcga ggccgacctg ggcctggacc gggtcacctg gcagcggcta    2580
gccgacacgg tggacctgat cgtggacccc gcggccctgg tcaaccacgt gctgccgtat    2640
agccagctgt tcggcccaaa cgcggcgggc accgccgagt tgcttcggct ggcgctgacc    2700
ggcaagcgca agccatacat ctacacctcg acgatcgccg tgggcgagca gatcccgccg    2760
gaggcgttca ccgaggacgc cgacatccgg gccatcagcc cgaccgcag gatcgacgac    2820 agctacgcca acggctacgc gaacagcaag tgggccggcg aggtgctgct gcgcgaagct    2880
cacgagcagt gcggcctgcc ggtgacggtc ttccgctgcg acatgatcct ggccgacacc    2940
agctataccg gtcagctcaa cctgccggac atgttcaccc ggctgatgct gagcctggcc    3000
gctaccggca tcgcacccgg ttcgttctat gagctggatg cgcacggcaa tcggcaacgc    3060
gcccactatg acggcttgcc ggtcgaattc gtcgcagaag ccatttgcac ccttgggaca    3120
catagcccgg accgttttgt cacctaccac gtgatgaacc cctacgacga cggcatcggg    3180
ctggacgagt tcgtcgactg gctcaactcc ccaactagcg ggtccggttg cacgatccag    3240
cggatcgccg actacggcga gtggctgcag cggttcgaga cttcgctgcg tgccttgccg    3300
gatcgccagc gccacgcctc gctgctgccc ttgctgcaca actaccgaga gcctgcaaag    3360
ccgatatgcg ggtcaatcgc gcccaccgac cagttccgcg ctgccgtcca agaagcgaaa    3420
atcggtccgg acaaagacat tccgcacctc acggcggcga tcatcgcgaa gtacatcagc    3480
aacctgcgac tgctcgggct gctgtga                                       3507
```

<210> SEQ ID NO 43
<211> LENGTH: 3522
<212> TYPE: DNA
<213> ORGANISM: Mycobacterium smegmatis

<400> SEQUENCE: 43

```
atgaccagcg atgttcacga cgccacagac ggcgtcaccg aaaccgcact cgacgacgag     60
cagtcgaccc gccgcatcgc cgagctgtac gccaccgatc ccgagttcgc cgccgccgca    120
ccgttgcccg ccgtggtcga cgcggcgcac aaacccgggc tgcggctggc agagatcctg    180
cagaccctgt tcaccggcta cggtgaccgc ccggcgctgg ataccgcgc ccgtgaactg     240 gccaccgacg agggcgggcg caccgtgacg cgtctgctgc gcggttcga cacccctcacc    300 tacgcccagg tgtggtcgcg cgtgcaagcg gtcgccgcgg ccctgcgcca caacttcgcg    360
cagccgatct accccggcga cgccgtcgcg acgatcggtt tcgcgagtcc cgattacctg    420
acgctggatc tcgtatgcgc ctacctgggc ctcgtgagtg ttccgctgca gcacaacgca    480
ccggtcagcc ggctcgcccc gatcctggcc gaggtcgaac cgcggatcct caccgtgagc    540
gccgaatacc tcgacctcgc agtcgaatcc gtgcgggacg tcaactcggt gtcgcagctc    600
gtggtgttcg accatcaccc cgaggtcgac gaccaccgcg acgcactggc ccgcgcgcgt    660
gaacaactcg ccggcaaggg catcgccgtc accaccctgg acgcgatcgc cgacgagggc    720
gccgggctgc cggccgaacc gatctacacc gccgaccatg atcagcgcct cgcgatgatc    780
```

```
ctgtacacct cgggttccac cggcgcaccc aagggtgcga tgtacaccga ggcgatggtg    840
gcgcggctgt ggaccatgtc gttcatcacg ggtgacccca cgccggtcat caacgtcaac    900
ttcatgccgc tcaaccacct gggcgggcgc atccccattt ccaccgccgt gcagaacggt    960
ggaaccagtt acttcgtacc ggaatccgac atgtccacgc tgttcgagga tctcgcgctg   1020
gtgcgcccga ccgaactcgg cctggttccg cgcgtcgccg acatgctcta ccagcaccac   1080
ctcgccaccg tcgaccgcct ggtcacgcag ggcgccgacg aactgaccgc cgagaagcag   1140
gccggtgccg aactgcgtga gcaggtgctc ggcggacgcg tgatcaccgg attcgtcagc   1200
accgcaccgc tggccgcgga gatgagggcg ttcctcgaca tcaccctggg cgcacacatc   1260
gtcgacggct acgggctcac cgagaccggc gccgtgacac gcgacggtgt gatcgtgcgg   1320
ccaccggtga tcgactacaa gctgatcgac gttcccgaac tcggctactt cagcaccgac   1380
aagccctacc gcgtggcga actgctggtc aggtcgcaaa cgctgactcc cgggtactac   1440 aagcccccg aggtcaccgc gagcgtcttc gaccgggacg gctactacca caccggcgac   1500
gtcatggccg agaccgcacc cgaccacctg gtgtacgtgg accgtcgcaa caacgtcctc   1560
aaactcgcgc agggcgagtt cgtggcggtc gccaacctgg aggcggtgtt ctccggcgcg   1620
gcgctggtgc gccagatctt cgtgtacggc aacagcgagc gcagtttcct tctggccgtg   1680
gtggtcccga cgccggaggc gctcgagcag tacgatccgg ccgcgctcaa ggccgcgctg   1740
gccgactcgc tgcagcgcac cgcacgcgac gccgaactgc aatcctacga ggtgccggcc   1800
gatttcatcg tcgagaccga ccgttcagc gccgccaacg ggctgctgtc gggtgtcgga   1860
aaactgctgc ggcccaacct caaagaccgc tacgggcagc gcctggagca gatgtacgcc   1920
gatatcgcgg ccacgcaggc caaccagttg cgcgaactgc ggcgcgcggc cgccacacaa   1980
ccggtgatcg acaccctcac ccaggccgct gccacgatcc tcggcaccgg gagcgaggtg   2040
gcatccgacg cccacttcac cgacctgggc ggggattccc tgtcggcgct gacactttcg   2100
aacctgctga gcgatttctt cggttttcgaa gttcccgtcg gcaccatcgt gaacccggcc   2160
accaacctcg cccaactcgc ccagcacatc gaggcgcagc gcaccgcggg tgaccgcagg   2220
ccgagtttca ccaccgtgca cggcgcggac gccaccgaga tccgggcgag tgagctgacc   2280
ctggacaagt tcatcgacgc cgaaacgctc cgggccgcac cgggtctgcc caaggtcacc   2340
accgagccac ggacggtgtt gctctcgggc gccaacggct ggctgggccg gttcctcacg   2400
ttgcagtggc tggaacgcct ggcacctgtc ggcggcaccc tcatcacgat cgtgcggggc   2460
cgcgacgacg ccgcggcccg cgcacggctg acccaggcct acgacaccga tcccgagttg   2520
tcccgccgct tcgccgagct ggccgaccgc cacctgcggg tggtcgccgg tgacatcggc   2580
gacccgaatc tgggcctcac acccgagatc tggcaccggc tcgccgccga ggtcgacctg   2640
gtggtgcatc cggcagcgct ggtcaaccac gtgctcccct accggcagct gttcggcccc   2700
aacgtcgtgg gcacggccga ggtgatcaag ctggccctca ccgaacggat caagcccgtc   2760
acgtacctgt ccaccgtgtc ggtggccatg gggatccccg acttcgagga ggacggcgac   2820
atccggaccg tgagcccggt gcgcccgctc gacggcggat acgccaacgg ctacggcaac   2880
agcaagtggg ccgcgaggt gctgctgcgg gaggcccacg atctgtgcgg gctgcccgtg   2940
gcgacgttcc gctcggacat gatcctggcg catccgcgct accgcggtca ggtcaacgtg   3000
ccagacatgt tcacgcgact cctgttgagc ctcttgatca ccggcgtcgc gccgcggtcg   3060
ttctacatcg gagacggtga gcgcccgcgg gcgcactacc ccggcctgac ggtcgatttc   3120
gtggccgagg cggtcacgac gctcggcgcg cagcagcgcg agggatacgt gtcctacgac   3180
```

```
gtgatgaacc cgcacgacga cgggatctcc ctggatgtgt tcgtggactg gctgatccgg    3240
gcgggccatc cgatcgaccg ggtcgacgac tacgacgact gggtgcgtcg gttcgagacc    3300
gcgttgaccg cgcttcccga gaagcgccgc gcacagaccg tactgccgct gctgcacgcg    3360
ttccgcgctc cgcaggcacc gttgcgcggc gcacccgaac ccacggaggt gttccacgcc    3420
gcggtgcgca ccgcgaaggt gggcccggga gacatcccgc acctcgacga ggcgctgatc    3480
gacaagtaca tacgcgatct gcgtgagttc ggtctgatct ga                      3522

<210> SEQ ID NO 44
<211> LENGTH: 3582
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44
atgggcagca gccatcatca tcatcatcac agcagcggcc tggtgccgcg cggcagccat      60
atgacgagcg atgttcacga cgcgaccgac ggcgttaccg agactgcact ggatgatgag     120
cagagcactc gtcgtattgc agaactgtac gcaacggacc cagagttcgc agcagcagct     180
cctctgccgg ccgttgtcga tgcggcgcac aaaccgggcc tgcgtctggc ggaaatcctg     240
cagaccctgt tcaccggcta cggcgatcgt ccggcgctgg gctatcgtgc acgtgagctg     300
gcgacggacg aaggcggtcg tacggtcacg cgtctgctgc cgcgcttcga taccctgacc     360
tatgcacagg tgtggagccg tgttcaagca gtggctgcag cgttgcgtca caatttcgca     420
caaccgattt acccgggcga cgcggtcgcg actatcggct ttgcgagccc ggactatttg     480
acgctggatc tggtgtgcgc gtatctgggc ctggtcagcg ttccttttgca gcataacgct     540 ccggtgtctc gcctggcccc gattctggcc gaggtgaaac cgcgtattct gacggtgagc     600
gcagaatacc tggacctggc ggttgaatcc gtccgtgatg tgaactccgt cagccagctg     660
gttgttttcg accatcatcc ggaagtggac gatcaccgtg acgcactggc tcgcgcacgc     720
gagcagctgg ccggcaaagg tatcgcagtt acgaccctgg atgcgatcgc agacgaaggc     780
gcaggtttgc cggctgagcc gatttacacg gcggatcacg atcagcgtct ggccatgatt     840
ctgtatacca gcggctctac gggtgctccg aaaggcgcga tgtacaccga agcgatggtg     900
gctcgcctgt ggactatgag ctttatcacg ggcgacccga ccccggttat caacgtgaac     960
ttcatgccgc tgaaccatct gggcggtcgt atcccgatta gcaccgccgt gcagaatggc    1020
ggtaccagct acttcgttcc ggaaagcgac atgagcacgc tgtttgagga tctggccctg    1080
gtccgcccta ccgaactggg tctggtgccg cgtgttgcgg acatgctgta ccagcatcat    1140
ctggcgaccg tggatcgcct ggtgacccag ggcgcggacg aactgactgc ggaaaagcag    1200
gccggtgcgg aactgcgtga acaggtcttg gcggtcgtg ttatcaccgg ttttgtttcc    1260
accgcgccgt tggcggcaga gatgcgtgct tttctggata tcaccttggg tgcacacatc    1320
gttgacggtt acggtctgac cgaaaccggt gcggtcaccc gtgatggtgt gattgttcgt    1380
cctccggtca ttgattacaa gctgatcgat gtgccggagc tgggttactt ctccaccgac    1440
aaaccgtacc cgcgtggcga gctgctggtt cgtagccaaa cgttgactcc gggttactac    1500
aagcgcccag aagtcaccgc gtccgttttc gatcgcgacg gctattacca caccggcgac    1560
gtgatggcag aaaccgcgcc agaccacctg gtgtatgtgg accgccgcaa caatgttctg    1620
```

```
aagctggcgc aaggtgaatt tgtcgccgtg gctaacctgg aggccgtttt cagcggcgct      1680
gctctggtcc gccagatttt cgtgtatggt aacagcgagc gcagctttct gttggctgtt      1740
gttgtcccta ccccggaggc gctggagcaa tacgaccctg ccgcattgaa agcagccctg      1800
gcggattcgc tgcagcgtac ggcgcgtgat gccgagctgc agagctatga agtgccggcg      1860
gacttcattg ttgagactga gccttttagc gctgcgaacg gtctgctgag cggtgttggc      1920
aagttgctgc gtccgaattt gaaggatcgc tacggtcagc gtttggagca gatgtacgcg      1980
gacatcgcgg ctacgcaggc gaaccaattg cgtgaactgc gccgtgctgc ggctactcaa      2040
ccggtgatcg acacgctgac gcaagctgcg gcgaccatcc tgggtaccgg cagcgaggtt      2100
gcaagcgacg cacactttac tgatttgggc ggtgattctc tgagcgcgct gacgttgagc      2160
aacttgctgt ctgacttctt tggctttgaa gtcccggttg gcacgattgt taacccagcg      2220
actaatctgg cacagctggc gcaacatatc gaggcgcagc gcacggcggg tgaccgccgt      2280
ccatccttta cgacggtcca cggtgcggat gctacggaaa tccgtgcaag cgaactgact      2340
ctggacaaat tcatcgacgc tgagactctg cgcgcagcac ctggtttgcc gaaggttacg      2400
actgagccgc gtacggtcct gttgagcggt gccaatggtt ggttgggccg cttcctgacc      2460
ctgcagtggc tggaacgttt ggcaccggtt ggcggtaccc tgatcaccat tgtgcgcggt      2520
cgtgacgatg cagcggcacg tgcacgtttg actcaggctt acgatacgga cccagagctg      2580
tcccgccgct tcgctgagtt ggcggatcgc cacttgcgtg tggtggcagg tgatatcggc      2640
gatccgaatc tgggcctgac cccggagatt tggcaccgtc tggcagcaga ggtcgatctg      2700
gtcgttcatc cagcggccct ggtcaaccac gtcctgccgt accgccagct gtttggtccg      2760
aatgttgttg gcaccgccga agttatcaag ttggctctga ccgagcgcat caagcctgtt      2820
acctacctgt ccacggttag cgtcgcgatg gtattcctg attttgagga ggacggtgac      2880
attcgtaccg tcagcccggt tcgtccgctg gatggtggct atgcaaatgg ctatggcaac      2940
agcaagtggg ctggcgaggt gctgctgcgc gaggcacatg acctgtgtgg cctgccggtt      3000
gcgacgtttc gtagcgacat gattctggcc caccgcgct accgtggcca agtgaatgtg      3060
ccggacatgt tcacccgtct gctgctgtcc ctgctgatca cgggtgtggc accgcgttcc      3120
ttctacattg gtgatggcga gcgtccgcgt gcacactacc cgggcctgac cgtcgatttt      3180
gttgcggaag cggttactac cctgggtgct cagcaacgtg agggtatgt ctcgtatgac      3240 gttatgaatc cgcacgatga cggtattagc ttggatgtct ttgtggactg gctgattcgt      3300
gcgggccacc caattgaccg tgttgacgac tatgatgact gggtgcgtcg ttttgaaacc      3360
gcgttgaccg ccttgccgga gaaacgtcgt gcgcagaccg ttctgccgct gctgcatgcc      3420
tttcgcgcgc cacaggcgcc gttgcgtggc gcccctgaac cgaccgaagt gtttcatgca      3480
gcggtgcgta ccgctaaagt cggtccgggt gatattccgc acctggatga agccctgatc      3540
gacaagtaca tccgtgacct gcgcgagttc ggtctgattt ag                        3582
```

<210> SEQ ID NO 45
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 45

```
cggttctggc aaatattctg aaatgagctg ttgacaatta atcaaatccg gctcgtataa      60
``` tgtgtg                                                         66

<210> SEQ ID NO 46
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
ggtttattcc tccttattta atcgatacat                               30

<210> SEQ ID NO 47
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
atgtatcgat taaataagga ggaataaacc atgggcacga gcgatgttca cgacgcgac     59

<210> SEQ ID NO 48
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
atgtatcgat taaataagga ggaataaacc gtgggcacga gcgatgttca cgacgcgac     59

<210> SEQ ID NO 49
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
atgtatcgat taaataagga ggaataaacc ttgggcacga gcgatgttca cgacgcgac     59

<210> SEQ ID NO 50
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
ttctaaatca gaccgaactc gcgcag                                   26

<210> SEQ ID NO 51
<211> LENGTH: 48
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 51
ctgcgcgagt tcggtctgat ttagaattcc tcgaggatgg tagtgtgg                    48

<210> SEQ ID NO 52
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
cagtcgacat acgaaacggg aatgcgg                                           27

<210> SEQ ID NO 53
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
ccgcattccc gtttcgtatg tcgactgaaa cctcaggcat tgagaagcac acgtc            56

<210> SEQ ID NO 54
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
ctcatttcag aatatttgcc agaaccgtta atttcctaat gcaggagtcg cataag           56

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
ggatctcgac gctctccctt                                                   20

<210> SEQ ID NO 56
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
tcaaaaacgc cattaacctg atgttctg                                          28
```

CAR ENZYMES AND IMPROVED PRODUCTION OF FATTY ALCOHOLS

CROSS-REFERENCE TO RELATED APPLICATIONS

This application claims the benefit of U.S. Provisional Application No. 61/619,309 filed Apr. 2, 2012, hereby incorporated by reference.

SEQUENCE LISTING

The instant application contains a Sequence Listing, which has been submitted in ASCII format via EFS-Web and is hereby incorporated by reference in its entirety. The ASCII copy, created on Apr. 2, 2013, is named LS00039PCT_SL.txt and is 89,038 bytes in size.

FIELD OF THE DISCLOSURE

The disclosure relates to variant carboxylic acid reductase (CAR) enzymes for the improved production of fatty alcohols in recombinant host cells. The disclosure further relates to variant CAR nucleic acids and polypeptides as well as recombinant host cells and cell cultures. Further encompassed are methods of making fatty alcohol compositions.

BACKGROUND OF THE DISCLOSURE

Fatty alcohols make up an important category of industrial biochemicals. These molecules and their derivatives have numerous uses, including as surfactants, lubricants, plasticizers, solvents, emulsifiers, emollients, thickeners, flavors, fragrances, and fuels. In industry, fatty alcohols are produced via catalytic hydrogenation of fatty acids produced from natural sources, such as coconut oil, palm oil, palm kernel oil, tallow and lard, or by chemical hydration of alpha-olefins produced from petrochemical feedstock. Fatty alcohols derived from natural sources have varying chain lengths. The chain length of fatty alcohols is important with respect to particular applications. In nature, fatty alcohols are also made by enzymes that are able to reduce acyl-ACP or acyl-CoA molecules to the corresponding primary alcohols (see, for example, U.S. Patent Publication Nos. 20100105955, 20100105963, and 20110250663, which are incorporated by reference herein).

Current technologies for producing fatty alcohols involve inorganic catalyst-mediated reduction of fatty acids to the corresponding primary alcohols, which is costly, time consuming and cumbersome. The fatty acids used in this process are derived from natural sources (e.g., plant and animal oils and fats, supra). Dehydration of fatty alcohols to alpha-olefins can also be accomplished by chemical catalysis. However, this technique is nonrenewable and associated with high operating cost and environmentally hazardous chemical wastes. Thus, there is a need for improved methods for fatty alcohol production and the instant disclosure addresses this need.

SUMMARY

One aspect of the disclosure provides a variant carboxylic acid reductase (CAR) polypeptide comprising an amino acid sequence having at least about 90% sequence identity to SEQ ID NO: 7, wherein the variant CAR polypeptide is genetically engineered to have at least one mutation at an amino acid position selected from the group of amino acid positions 3, 18, 20, 22, 80, 87, 191, 288, 473, 535, 750, 827, 870, 873, 926, 927, 930, and 1128. Herein, the expression of the variant CAR polypeptide in a recombinant host cell results in a higher titer of fatty alcohol compositions compared to a recombinant host cell expressing a corresponding wild type polypeptide. In a related aspect, the CAR polypeptide is a CarB polypeptide. In another related aspect, the variant CAR polypeptide comprises a mutation at positions S3R, D18R, D18L, D18T, D18P, E20V, E20S, E20R, S22R, S22N, S22G, L80R, R87G, R87E, V191S, F288R, F288S, F288G, Q473L, Q473W, Q473Y, Q473I, Q473H, A535S, D750A, R827C, R827A, I870L, R873S, V926A, V926E, S927K, S927G, M930K, M930R and/or L1128W. In a related aspect, the CAR polypeptide includes mutation A535S; or mutations E20R, F288G, Q473I and A535S; or mutations E20R, F288G, Q473H, A535S, R827A and S927G; or mutations E20R, S22R, F288G, Q473H, A535S, R827A and S927G; or mutations S3R, E20R, S22R, F288G, Q473H, A535S, R873S, S927G, M930R and L1128W; or E20R, S22R, F288G, Q473H, A535S, R873S, S927G, M930R and L1128W; or mutations D18R, E20R, S22R, F288G, Q473I, A535S, S927G, M930K and L1128W; or mutations E20R, S22R, F288G, Q473I, A535S, R827C, V926E, S927K and M930R; or mutations D18R, E20R, 288G, Q473I, A535S, R827C, V926E, M930K and L1128W; or mutations E20R, S22R, F288G, Q473H, A535S, R827C, V926A, S927K and M930R; or mutations E20R, S22R, F288G, Q473H, A535S and R827C; or mutations E20R, S22R, F288G, Q473I, A535S, R827C and M930R; or mutations E20R, S22R, F288G, Q473I, A535S, I870L, S927G and M930R; or mutations E20R, S22R, F288G, Q473I, A535S, I870L and S927G; or mutations D18R, E20R, S22R, F288G, Q473I, A535S, R827C, I870L, V926A and S927G; or mutations E20R, S22R, F288G, Q473H, A535S, R827C, I870L and L1128W; or mutations D18R, E20R, S22R, F288G, Q473H, A535S, R827C, I870L, S927G and L1128W; or mutations E20R, S22R, F288G, Q473I, A535S, R827C, I870L, S927G and L1128W; or mutations E20R, S22R, F288G, Q473I, A535S, R827C, I870L, S927G, M930K and L1128W; or mutations E20R, S22R, F288G, Q473H, A535S, I870L, S927G and M930K; or mutations E20R, F288G, Q473I, A535S, I870L, M930K; or mutations E20R, S22R, F288G, Q473H, A535S, S927G, M930K and L1128W; or mutations D18R, E20R, S22R, F288G, Q473I, A535S, S927G and L1128W; or mutations E20R, S22R, F288G, Q473I, A535S, R827C, I870L and S927G; or mutations D18R, E20R, S22R, F288G, Q473I, A535S, R827C, I870L, S927G and L1128W; or mutations D18R, E20R, S22R, F288G, Q473I, A535S, S927G, M930R and L1128W; or mutations E20R, S22R, F288G, Q473H, A535S, V926E, S927G and M930R; or mutations E20R, S22R, F288G, Q473H, A535S, R827C, I870L, V926A and L1128W; or combinations thereof.

Another aspect of the disclosure provides a host cell including a polynucleotide sequence encoding a variant carboxylic acid reductase (CAR) polypeptide having at least 90% sequence identity to SEQ ID NO: 7 and having at least one mutation at an amino acid position including amino acid positions 3, 18, 20, 22, 80, 87, 191, 288, 473, 535, 750, 827, 870, 873, 926, 927, 930, and 1128, wherein the genetically engineered host cell produces a fatty alcohol composition at a higher titer or yield than a host cell expressing a corresponding wild type CAR polypeptide when cultured in a medium containing a carbon source under conditions effective to express the variant CAR polypeptide, and wherein the SEQ ID NO: 7 is the corresponding wild type CAR polypeptide. In a related aspect, the recombinant host cell further includes a polynucleotide encoding a thioesterase polypeptide. In another related aspect, the recombinant host cell further includes a polynucleotide encoding a FabB polypeptide and a FadR polypeptide. In another related aspect, the disclosure provides a recombinant host cell that includes a polynucleotide encoding a fatty aldehyde reductase (AlrA) and a cell culture containing it.

Another aspect of the disclosure provides a recombinant host cell, wherein the genetically engineered host cell has a titer that is at least 3 times greater than the titer of a host cell expressing the corresponding wild type CAR polypeptide when cultured under the same conditions as the genetically engineered host cell. In one related aspect, the genetically engineered host cell has a titer of from about 30 g/L to about 250 g/L. In another related aspect, the genetically engineered host cell has a titer of from about 90 g/L to about 120 g/L.

Another aspect of the disclosure provides a recombinant host cell, wherein the genetically engineered host cell has a yield that is at least 3 times greater than the yield of a host cell expressing the corresponding wild type CAR polypeptide when cultured under the same conditions as the genetically engineered host cell. In one related aspect, the genetically engineered host cell has a yield from about 10% to about 40%.

The disclosure further encompasses a cell culture including the recombinant host cell as described herein. In a related aspect, the cell culture has a productivity that is at least about 3 times greater than the productivity of a cell culture that expresses the corresponding wild type CAR polypeptide. In another related aspect, the productivity ranges from about 0.7 mg/L/hr to about 3 g/L/hr. In another related aspect, the culture medium comprises a fatty alcohol composition. The fatty alcohol composition is produced extracellularly. The fatty alcohol composition may include one or more of a C6, C8, C10, C12, C13, C14, C15, C16, C17, or C18 fatty alcohol; or a C10:1, C12:1, C14:1, C16:1, or a C18:1 unsaturated fatty alcohol. In another related aspect, the fatty alcohol composition comprises C12 and C14 fatty alcohols. In yet, another related aspect, the fatty alcohol composition comprises C12 and C14 fatty alcohols at a ratio of about 3:1. In still another related aspect, the fatty alcohol composition encompasses unsaturated fatty alcohols. In addition, the fatty alcohol composition may include a fatty alcohol having a double bond at position 7 in the carbon chain between C7 and C8 from the reduced end of the fatty alcohol. In another aspect, the fatty alcohol composition includes saturated fatty alcohols. In another aspect, the fatty alcohol composition includes branched chain fatty alcohols.

The disclosure further contemplates a method of making a fatty alcohol composition at a high titer, yield or productivity, including the steps of engineering a recombinant host cell; culturing the recombinant host cell in a medium including a carbon source; and optionally isolating the fatty alcohol composition from the medium

BRIEF DESCRIPTION OF THE DRAWINGS

The present disclosure is best understood when read in conjunction with the accompanying figures, which serve to illustrate the preferred embodiments. It is understood, however, that the disclosure is not limited to the specific embodiments disclosed in the figures.

FIGS. 6A and 6B show data for production of "Total Fatty Species" from duplicate plate screens when plasmid pCL-WT TRC WT TesA was transformed into each of the strains shown in the figures and a fermentation was run in FA2 media with 20 hours from induction to harvest at both 32° C. (FIG. 6A) and 37° C. (FIG. 6B).

DETAILED DESCRIPTION

General Overview

Figure 1:
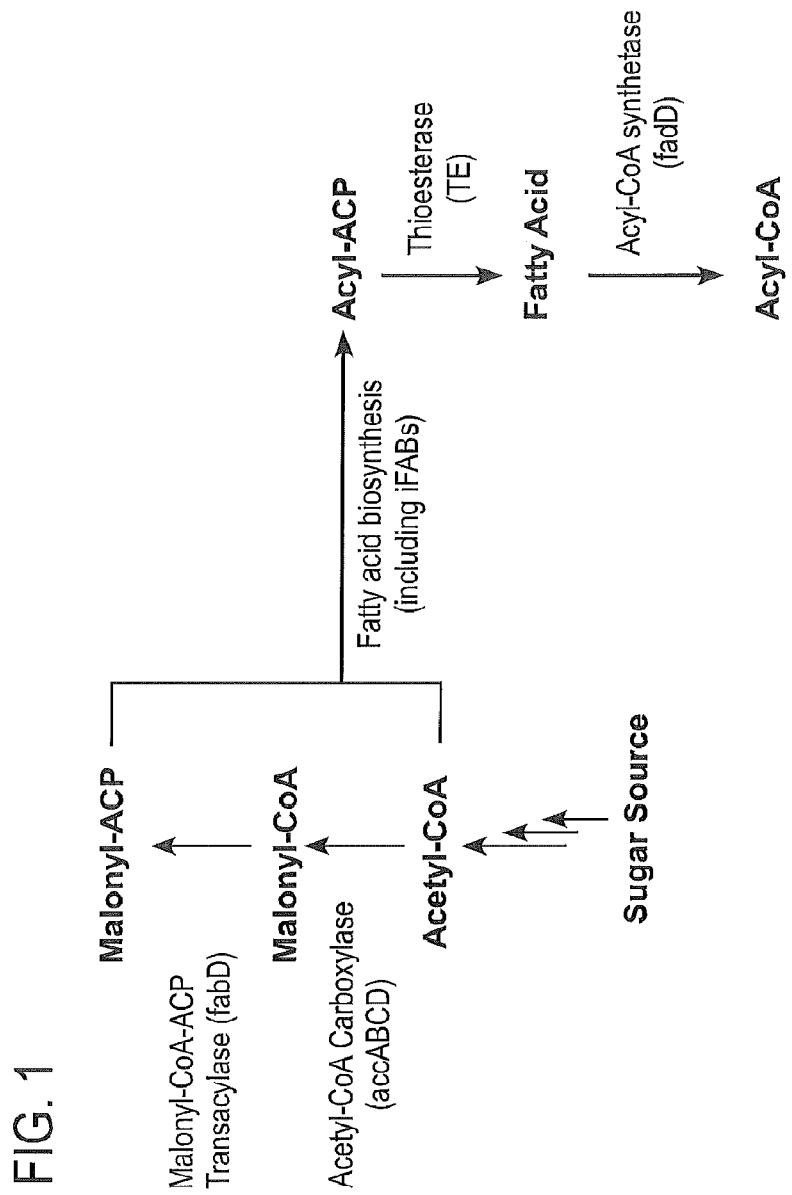
FIG. 1 is a schematic overview of an exemplary biosynthetic pathway for use in production of acyl CoA as a precursor to fatty acid derivatives in a recombinant host cell. The cycle is initiated by condensation of malonyl-ACP and acetyl-CoA.

The present disclosure provides novel variant carboxylic acid reductase (CAR) enzymes as well as their nucleic acid and protein sequences. Further encompassed by the disclosure are recombinant host cells and cell cultures that include the variant CAR enzymes for the production of fatty alcohols. In order for the production of fatty alcohols from fermentable sugars or biomass to be commercially viable, the process must be optimized for efficient conversion and recovery of product. The present disclosure addresses this need by providing compositions and methods for improved production of fatty alcohols using engineered variant enzymes and engineered recombinant host cells. The host cells serve as biocatalysts resulting in high-titer production of fatty alcohols using fermentation processes. As such, the disclosure further provides methods to create photosynthetic and heterotrophic host cells that produce fatty alcohols and alpha-olefins of specific chain lengths directly such that catalytic conversion of purified fatty acids is not necessary. This new method provides product quality and cost advantages.

More specifically, the production of a desired fatty alcohol composition may be enhanced by modifying the expression of one or more genes involved in a biosynthetic pathway for fatty alcohol production, degradation and/or secretion. The disclosure provides recombinant host cells, which have been engineered to provide enhanced fatty alcohol biosynthesis relative to non-engineered or native host cells (e.g., strain improvements). The disclosure also provides polynucleotides useful in the recombinant host cells, methods, and compositions of the disclosure. However it will be recognized that absolute sequence identity to such polynucleotides is not necessary. For example, changes in a particular polynucleotide sequence can be made and the encoded polypeptide evaluated for activity. Such changes typically comprise conservative mutations and silent mutations (e.g., codon optimization). Modified or mutated polynucleotides (i.e., mutants) and encoded variant polypeptides can be screened for a desired function, such as, an improved function compared to the parent polypeptide, including but not limited to increased catalytic activity, increased stability, or decreased inhibition (e.g., decreased feedback inhibition), using methods known in the art.

The disclosure identifies enzymatic activities involved in various steps (i.e., reactions) of the fatty acid biosynthetic pathways described herein according to Enzyme Classification (EC) number, and provides exemplary polypeptides (i.e., enzymes) categorized by such EC numbers, and exemplary polynucleotides encoding such polypeptides. Such exemplary polypeptides and polynucleotides, which are identified herein by Accession Numbers and/or Sequence Identifier Numbers (SEQ ID NOs), are useful for engineering fatty acid pathways in parental host cells to obtain the recombinant host cells described herein. It is to be understood, however, that polypeptides and polynucleotides described herein are exemplary and non-limiting. The sequences of homologues of exemplary polypeptides described herein are available to those of skill in the art using databases (e.g., the Entrez databases provided by the National Center for Biotechnology Information (NCBI), the ExPasy databases provided by the Swiss Institute of Bioinformatics, the BRENDA database provided by the Technical University of Braunschweig, and the KEGG database provided by the Bioinformatics Center of Kyoto University and University of Tokyo, all which are available on the World Wide Web).

A variety of host cells can be modified to contain a fatty alcohol biosynthetic enzymes such as those described herein, resulting in recombinant host cells suitable for the production of fatty alcohol compositions. It is understood that a variety of cells can provide sources of genetic material, including polynucleotide sequences that encode polypeptides suitable for use in a recombinant host cell provided herein.

Definitions

Unless defined otherwise, all technical and scientific terms used herein have the same meaning as commonly understood by one of ordinary skill in the art to which the disclosure pertains. Although other methods and materials similar, or equivalent, to those described herein can be used in the practice of the present disclosure, the preferred materials and methods are described herein. In describing and claiming the present disclosure, the following terminology will be used in accordance with the definitions set out below.

Accession Numbers: Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) Numbers: EC numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction catalyzed.

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

As used herein, the term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms "polypeptide" and "protein" are used interchangeably to refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide.

As used herein, the terms "homolog," and "homologous" refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and sequence "identity" are used interchangeably.

One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a first sequence that is aligned for comparison purposes is at least about 30%, preferably at least about 40%, more preferably at least about 50%, even more preferably at least about 60%, and even more preferably at least about 70%, at least about 80%, at least about 90%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences.

The comparison of sequences and determination of percent homology between two sequences can be accomplished using a mathematical algorithm, such as BLAST (Altschul et al., J. Mol. Biol., 215(3): 403-410 (1990)). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, J. Mol. Biol., 48: 444-453 (1970)). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg, BMC Bioinformatics, 6: 278 (2005); Altschul, et al., FEBS J., 272(20): 5101-5109 (2005)).

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and non-aqueous methods are described in that reference and either method can be used. Specific hybridization conditions referred to herein are as follows: 1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions—6×SSC at about 45° C., followed by one or more washes in 0.2×SSC, 0.1% SDS at 60° C.; 3) high stringency hybridization conditions—6×SSC at about 45° C., followed by one or more washes in 0.2.×SSC, 0.1% SDS at 65° C.; and 4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

An "endogenous" polypeptide refers to a polypeptide encoded by the genome of the parental microbial cell (also termed "host cell") from which the recombinant cell is engineered (or "derived").

An "exogenous" polypeptide refers to a polypeptide, which is not encoded by the genome of the parental microbial cell. A variant (i.e., mutant) polypeptide is an example of an exogenous polypeptide.

The term "heterologous" generally means derived from a different species or derived from a different organism. As used herein it refers to a nucleotide sequence or a polypeptide sequence that is not naturally present in a particular organism. Heterologous expression means that a protein or polypeptide is experimentally added to a cell that does not normally express that protein. As such, heterologous refers to the fact that a transferred protein was initially derived from a different cell type or a different species then the recipient. For example, a polynucleotide sequence endogenous to a plant cell can be introduced into a bacterial host cell by recombinant methods, and the plant polynucleotide is then a heterologous polynucleotide in a recombinant bacterial host cell.

As used herein, the term "fragment" of a polypeptide refers to a shorter portion of a full-length polypeptide or protein ranging in size from four amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

As used herein, the term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science,* 236: 1237-1245 (1987)). Exemplary expression control sequences are described in, for example, Goeddel, *Gene Expression Technology: Methods in Enzymology*, Vol. 185, Academic Press, San Diego, Calif. (1990).

In the methods of the disclosure, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, inasmuch as a plasmid is the most commonly used form of vector. However, also included are such other forms of expression vectors that serve equivalent functions and that become known in the art subsequently hereto. In some embodiments, the recombinant vector comprises at least one sequence including (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. In certain embodiments, a polynucleotide sequence of the disclosure is operably linked to a promoter derived from bacteriophage T5. In certain embodiments, the host cell is a yeast cell, and the expression vector is a yeast expression vector. Examples of vectors for expression in yeast *S. cerevisiae* include pYepSec1 (Baldari et al., *EMBO J.,* 6: 229-234 (1987)), pMFa (Kurjan et al., *Cell,* 30: 933-943 (1982)), pJRY88 (Schultz et al., *Gene,* 54: 113-123 (1987)), pYES2 (Invitrogen Corp., San Diego, Calif.), and picZ (Invitrogen Corp., San Diego, Calif.). In other embodiments, the host cell is an insect cell, and the expression vector is a baculovirus expression vector. Baculovirus vectors available for expression of proteins in cultured insect cells (e.g., 519 cells) include, for example, the pAc series (Smith et al., *Mol. Cell Biol.,* 3: 2156-2165 (1983)) and the pVL series (Lucklow et al., *Virology,* 170: 31-39 (1989)). In yet another embodiment, the polynucleotide sequences described herein can be expressed in mammalian cells using a mammalian expression vector. Other suitable expression systems for both prokaryotic and eukaryotic cells are well known in the art; see, e.g., Sambrook et al., "Molecular Cloning: A Laboratory Manual," second edition, Cold Spring Harbor Laboratory, (1989).

As used herein "Acyl-CoA" refers to an acyl thioester formed between the carbonyl carbon of alkyl chain and the sulfhydryl group of the 4'-phosphopantethionyl moiety of coenzyme A (CoA), which has the formula R—C(O)S-CoA, where R is any alkyl group having at least 4 carbon atoms.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

As used herein, the term "fatty acid or derivative thereof" means a "fatty acid" or a "fatty acid derivative." The term "fatty acid" means a carboxylic acid having the formula RCOOH. R represents an aliphatic group, preferably an alkyl group. R can comprise between about 4 and about 22 carbon atoms. Fatty acids can be saturated, monounsaturated, or polyunsaturated. In a preferred embodiment, the fatty acid is made from a fatty acid biosynthetic pathway. The term "fatty acid derivative" means products made in part from the fatty acid biosynthetic pathway of the production host organism. "Fatty acid derivative" also includes products made in part from acyl-ACP or acyl-ACP derivatives. Exemplary fatty acid derivatives include, for example, acyl-CoA, fatty aldehydes, short and long chain alcohols, hydrocarbons, and esters (e.g., waxes, fatty acid esters, or fatty esters).

As used herein, the term "fatty acid biosynthetic pathway" means a biosynthetic pathway that produces fatty acid derivatives, for example, fatty alcohols. The fatty acid biosynthetic pathway includes fatty acid synthases that can be engineered to produce fatty acids, and in some embodiments can be expressed with additional enzymes to produce fatty acid derivatives, such as fatty alcohols having desired characteristics.

As used herein, "fatty aldehyde" means an aldehyde having the formula RCHO characterized by a carbonyl group (C=O). In some embodiments, the fatty aldehyde is any aldehyde made from a fatty alcohol. In certain embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty aldehyde is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty aldehyde. In certain embodiments, the fatty aldehyde is a $C_6$, $C_8$, $C_{10}$, $C_{12}$, $C_{13}$, $C_{14}$, $C_{15}$, $C_{16}$, $C_{17}$, or $C_{18}$ fatty aldehyde.

As used herein, "fatty alcohol" means an alcohol having the formula ROH. In some embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty alcohol is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty alcohol. In certain embodiments, the fatty alcohol is a $C_6$, $C_8$, $C_{10}$, $C_{12}$, $C_{13}$, $C_{14}$, $C_{15}$, $C_{16}$, $C_{17}$, or $C_{18}$ fatty alcohol.

A "fatty alcohol composition" as referred to herein is produced by a recombinant host cell and typically comprises a mixture of fatty alcohols. In some cases, the mixture includes more than one type of product (e.g., fatty alcohols and fatty acids). In other cases, the fatty acid derivative compositions may comprise, for example, a mixture of fatty alcohols with various chain lengths and saturation or branching characteristics. In still other cases, the fatty alcohol composition comprises a mixture of both more than one type of product and products with various chain lengths and saturation or branching characteristics.

A host cell engineered to produce a fatty aldehyde will typically convert some of the fatty aldehyde to a fatty alcohol. When a host cell, which produces fatty alcohols is engineered to express a polynucleotide encoding an ester synthase, wax esters are produced. In one embodiment, fatty alcohols are made from a fatty acid biosynthetic pathway. As an example, Acyl-ACP can be converted to fatty acids via the action of a thioesterase (e.g., *E. coli* TesA), which are converted to fatty aldehydes and fatty alcohols via the action of a carboxylic acid reductase (e.g., *E. coli* CarB). Conversion of fatty aldehydes to fatty alcohols can be further facilitated, for example, via the action of a fatty alcohol biosynthetic polypeptide. In some embodiments, a gene encoding a fatty alcohol biosynthetic polypeptide is expressed or overexpressed in the host cell. In certain embodiments, the fatty alcohol biosynthetic polypeptide has aldehyde reductase or alcohol dehydrogenase activity. Examples of alcohol dehydrogenase polypeptides useful in accordance with the disclosure include, but are not limited to AlrA of *Acinetobacter* sp. M-1 (SEQ ID NO: 3) or AlrA homologs, such as AlrAadp1 (SEQ ID NO:4) and endogenous *E. coli* alcohol dehydrogenases such as YjgB, (AAC77226) (SEQ ID NO: 5), DkgA (NP_417485), DkgB (NP_414743), YdjL (AAC74846), YdjJ (NP_416288), AdhP (NP_415995), YhdH (NP_417719), YahK (NP_414859), YphC (AAC75598), YqhD (446856) and YbbO [AAC73595.1]. Additional examples are described in International Patent Application Publication Nos. WO2007/136762, WO2008/119082 and WO2010/062480, each of which is expressly incorporated by reference herein. In certain embodiments, the fatty alcohol biosynthetic polypeptide has aldehyde reductase or alcohol dehydrogenase activity (EC 1.1.1.1).

As used herein, the term "alcohol dehydrogenase" refers to a polypeptide capable of catalyzing the conversion of a fatty aldehyde to an alcohol (e.g., fatty alcohol). One of ordinary skill in the art will appreciate that certain alcohol dehydrogenases are capable of catalyzing other reactions as well, and these non-specific alcohol dehydrogenases also are encompassed by the term "alcohol dehydrogenase." The R group of a fatty acid, fatty aldehyde, or fatty alcohol can be a straight chain or a branched chain. Branched chains may have more than one point of branching and may include cyclic branches. In some embodiments, the branched fatty acid, branched fatty aldehyde, or branched fatty alcohol is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ branched fatty acid, branched fatty aldehyde, or branched fatty alcohol. In particular embodiments, the branched fatty acid, branched fatty aldehyde, or branched fatty alcohol is a $C_6$, $C_8$, $C_{10}$, $C_{12}$, $C_{13}$, $C_{14}$, $C_{15}$, $C_{16}$, $C_{17}$, or $C_{18}$ branched fatty acid, branched fatty aldehyde, or branched fatty alcohol. In certain embodiments, the hydroxyl group of the branched fatty acid, branched fatty aldehyde, or branched fatty alcohol is in the primary ($C_1$) position. In certain embodiments, the branched fatty acid, branched fatty aldehyde, or branched fatty alcohol is an iso-fatty acid, iso-fatty aldehyde, or iso-fatty alcohol, or an antesio-fatty acid, an anteiso-fatty aldehyde, or anteiso-fatty alcohol. In exemplary embodiments, the branched fatty acid, branched fatty aldehyde, or branched fatty alcohol is selected from iso-$C_{7:0}$, iso-$C_{8:0}$, iso-$C_{9:0}$, iso-$C_{10:0}$, iso-$C_{11:0}$, iso-$C_{12:0}$, iso-$C_{13:0}$, iso-$C_{14:0}$, iso-$C_{15:0}$, iso-$C_{16:0}$, iso-$C_{17:0}$, iso-$C_{18:0}$, iso-$C_{19:0}$, anteiso-$C_{7:0}$, anteiso-$C_{8:0}$, anteiso-$C_{9:0}$, anteiso-$C_{10:0}$, anteiso-$C_{11:0}$, anteiso-$C_{12:0}$, anteiso-$C_{13:0}$, anteiso-$C_{14:0}$, anteiso-$C_{15:0}$, anteiso-$C_{16:0}$, anteiso-$C_{17:0}$, anteiso-$C_{18:0}$, and anteiso-$C_{19:0}$ branched fatty acid, branched fatty aldehyde or branched fatty alcohol. The R group of a branched or unbranched fatty acid, branched or unbranched fatty aldehyde, or branched or unbranched fatty alcohol can be saturated or unsaturated. If unsaturated, the R group can have one or more than one point of unsaturation. In some embodiments, the unsaturated fatty acid, unsaturated fatty aldehyde, or unsaturated fatty alcohol is a monounsaturated fatty acid, monounsaturated fatty aldehyde, or monounsaturated fatty alcohol. In certain embodiments, the unsaturated fatty acid, unsaturated fatty aldehyde, or unsaturated fatty alcohol is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or a C26:1 unsaturated fatty acid, unsaturated fatty aldehyde, or unsaturated fatty alcohol. In certain preferred embodiments, the unsaturated fatty acid, unsaturated fatty aldehyde, or unsaturated fatty alcohol is C10:1, C12:1, C14:1, C16:1, or C18:1. In yet other embodiments, the unsaturated fatty acid, unsaturated fatty aldehyde, or unsaturated fatty alcohol is unsaturated at the omega-7 position. In certain embodiments, the unsaturated fatty acid, unsaturated fatty aldehyde, or unsaturated fatty alcohol comprises a cis double bond.

As used herein, a recombinant or engineered "host cell" is a host cell, e.g., a microorganism that has been modified such that it produces fatty alcohols. In some embodiments, the recombinant host cell comprises one or more polynucleotides, each polynucleotide encoding a polypeptide having fatty aldehyde and/or fatty alcohol biosynthetic enzyme activity, wherein the recombinant host cell produces a fatty alcohol composition when cultured in the presence of a carbon source under conditions effective to express the polynucleotides.

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen. "Culturing" or "cultivation" refers to growing a population of microbial cells under suitable conditions in a liquid or solid medium. In particular embodiments, culturing refers to the fermentative bioconversion of a substrate to an end-product. Culturing media are well known and individual components of such culture media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium. The host cell can be additionally engineered to assimilate carbon efficiently and use cellulosic materials as carbon sources according to methods described for example in U.S. Pat. Nos. 5,000,000; 5,028,539; 5,424,202; 5,482,846; 5,602,030 and WO2010127318, each of which is expressly incorporated by reference herein. In addition, the host cell can be engineered to express an invertase so that sucrose can be used as a carbon source.

As used herein, the term "under conditions effective to express said heterologous nucleotide sequences" means any conditions that allow a host cell to produce a desired fatty aldehyde or fatty alcohol. Suitable conditions include, for example, fermentation conditions.

As used herein, "modified" or an "altered level of" activity of a protein, for example an enzyme, in a recombinant host cell refers to a difference in one or more characteristics in the activity determined relative to the parent or native host cell. Typically differences in activity are determined between a recombinant host cell, having modified activity, and the corresponding wild-type host cell (e.g., comparison of a culture of a recombinant host cell relative to wild-type host cell). Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein. In certain instances, the coding sequences for the polypeptides described herein are codon optimized for expression in a particular host cell. For example, for expression in E. coli, one or more codons can be optimized as described in, e.g., Grosjean et al., Gene 18:199-209 (1982).

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons).

As used herein, the phrase "the expression of said nucleotide sequence is modified relative to the wild type nucleotide sequence," means an increase or decrease in the level of expression and/or activity of an endogenous nucleotide sequence or the expression and/or activity of a heterologous or non-native polypeptide-encoding nucleotide sequence. As used herein, the term "overexpress" means to express or cause to be expressed a polynucleotide or polypeptide in a cell at a greater concentration than is normally expressed in a corresponding wild-type cell under the same conditions.

The terms "altered level of expression" and "modified level of expression" are used interchangeably and mean that a polynucleotide, polypeptide, or hydrocarbon is present in a different concentration in an engineered host cell as compared to its concentration in a corresponding wild-type cell under the same conditions.

As used herein, the term "titer" refers to the quantity of fatty aldehyde or fatty alcohol produced per unit volume of host cell culture. In any aspect of the compositions and methods described herein, a fatty alcohol is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty aldehyde or fatty alcohol is produced at a titer of more than 100 g/L, more than 200 g/L, more than 300 g/L, or higher, such as 500 g/L, 700 g/L, 1000 g/L, 1200 g/L, 1500 g/L, or 2000 g/L. The preferred titer of fatty aldehyde or fatty alcohol produced by a recombinant host cell according to the methods of the disclosure is from 5 g/L to 200 g/L, 10 g/L to 150 g/L, 20 g/L to 120 g/L and 30 g/L to 100 g/L.

As used herein, the term "yield of the fatty aldehyde or fatty alcohol produced by a host cell" refers to the efficiency by which an input carbon source is converted to product (i.e., fatty alcohol or fatty aldehyde) in a host cell. Host cells engineered to produce fatty alcohols and/or fatty aldehydes according to the methods of the disclosure have a yield of at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% or a range bounded by any two of the foregoing values. In other embodiments, a fatty aldehyde or fatty alcohol is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of the fatty alcohol or fatty aldehyde produced by the recombinant host cell according to the methods of the disclosure can be 5% to 15%, 10% to 25%, 10% to 22%, 15% to 27%, 18% to 22%, 20% to 28%, or 20% to 30%. The preferred yield of fatty alcohol produced by the recombinant host cell according to the methods of the disclosure is from 10% to 30%.

As used herein, the term "productivity" refers to the quantity of fatty aldehyde or fatty alcohol produced per unit volume of host cell culture per unit time. In any aspect of the compositions and methods described herein, the productivity of fatty aldehyde or fatty alcohol produced by a recombinant host cell is at least 100 mg/L/hour, at least 200 mg/L/hour$_0$, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, or at least 2500 mg/L/hour. Alternatively, or in addition, the productivity is 2500 mg/L/hour or less, 2000 mg/L/OD$_{600}$ or less, 1500 mg/L/OD$_{600}$ or less, 120 mg/L/hour, or less, 1000 mg/L/hour or less, 800 mg/L/hour, or less, or 600 mg/L/hour or less. Thus, the productivity can be bounded by any two of the above endpoints. For example, the productivity can be 3 to 30 mg/L/hour$_0$, 6 to 20 mg/L/hour, or 15 to 30 mg/L/hour. The preferred productivity of a fatty aldehyde or fatty alcohol produced by a recombinant host cell according to the methods of the disclosure is selected from 500 mg/L/hour to 2500 mg/L/hour, or from 700 mg/L/hour to 2000 mg/L/hour.

The terms "total fatty species" and "total fatty acid product" may be used interchangeably herein with reference to the total amount of fatty alcohols, fatty aldehydes, free fatty acids, and fatty esters present in a sample as evaluated by GC-FID as described in International Patent Application Publication WO 2008/119082. Samples may contain one, two, three, or four of these compounds depending on the context.

As used herein, the term "glucose utilization rate" means the amount of glucose used by the culture per unit time, reported as grams/liter/hour (g/L/hr).

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain preferred embodiments, the carbon source is biomass. In other preferred embodiments, the carbon source is glucose. In other preferred embodiments the carbon source is sucrose.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a biofuel. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, and food leftovers. The term "biomass" also can refer to sources of carbon, such as carbohydrates (e.g., monosaccharides, disaccharides, or polysaccharides).

As used herein, the term "isolated," with respect to products (such as fatty acids and derivatives thereof) refers to products that are separated from cellular components, cell culture media, or chemical or synthetic precursors. The fatty acids and derivatives thereof produced by the methods described herein can be relatively immiscible in the fermentation broth, as well as in the cytoplasm. Therefore, the fatty acids and derivatives thereof can collect in an organic phase either intracellularly or extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of a fatty aldehyde or a fatty alcohol in a sample. For example, when a fatty aldehyde or a fatty alcohol is produced in a recombinant host cell, the fatty aldehyde or fatty alcohol can be purified by the removal of recombinant host cell proteins. After purification, the percentage of a fatty aldehyde or a fatty alcohol in the sample is increased. The terms "purify," "purified," and "purification" are relative terms which do not require absolute purity. Thus, for example, when a fatty aldehyde or a fatty alcohol is produced in recombinant host cells, a purified fatty aldehyde or a purified fatty alcohol is a fatty aldehyde or a fatty alcohol that is substantially separated from other cellular components (e.g., nucleic acids, polypeptides, lipids, carbohydrates, or other hydrocarbons).

Strain Improvements

In order to meet very high targets for titer, yield, and/or productivity of fatty alcohols, a number of modifications were made to the production host cells. FadR is a key regulatory factor involved in fatty acid degradation and fatty acid biosynthesis pathways (Cronan et al., *Mol. Microbiol.*, 29(4): 937-943 (1998)). The *E. coli* ACS enzyme FadD and the fatty acid transport protein FadL are essential components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which can bind to the transcription factor FadR and derepress the expression of the fad genes that encode proteins responsible for fatty acid transport (FadL), activation (FadD), and β-oxidation (FadA, FadB, FadE, and FadH). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that can result in different end-products (Caviglia et al., *J. Biol. Chem.*, 279 (12): 1163-1169 (2004)). U.S. Provisional Application No. 61/470,989 describes improved methods of producing fatty acid derivatives in a host cell which is genetically engineered to have an altered level of expression of a FadR polypeptide as compared to the level of expression of the FadR polypeptide in a corresponding wild-type host cell.

Figure 2:
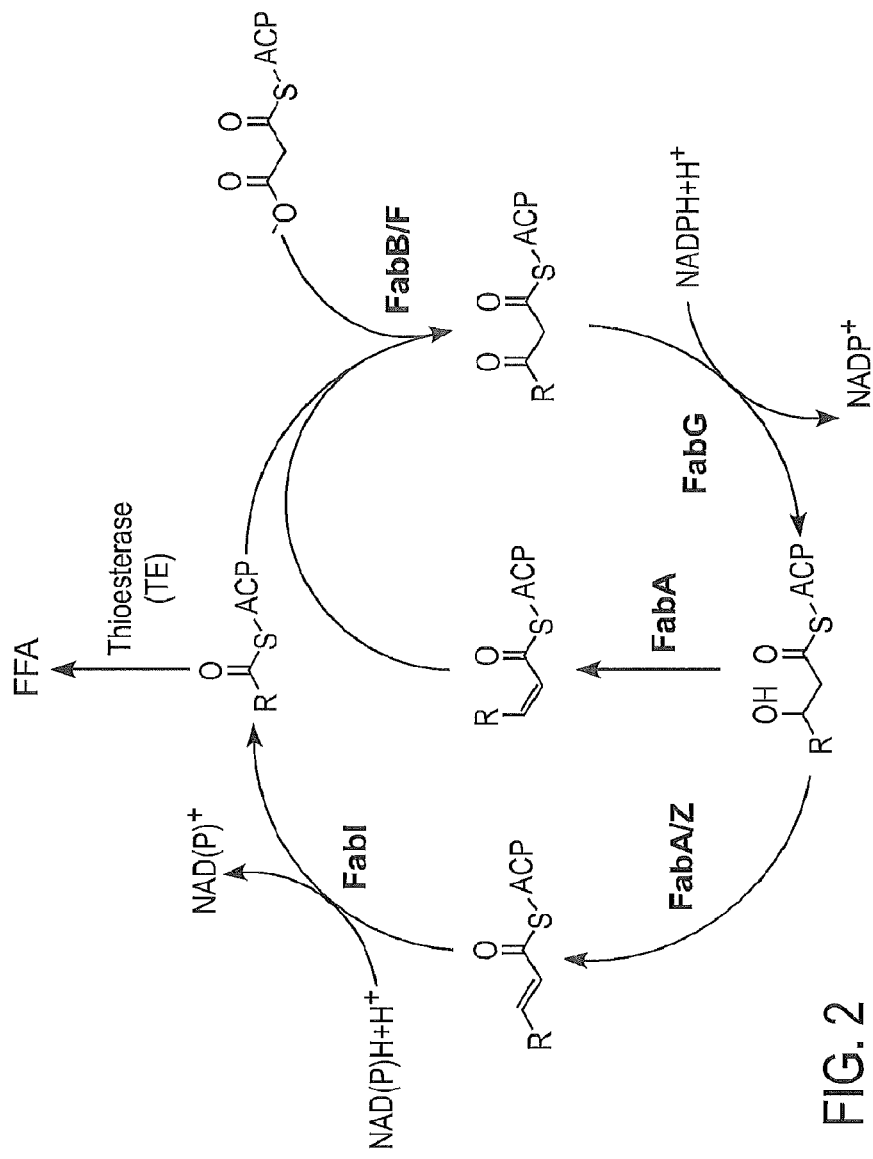
FIG. 2 is a schematic overview of an exemplary fatty acid biosynthetic cycle, where malonyl-ACP is produced by the transacylation of malonyl-CoA to malonyl-ACP (catalyzed by malonyl-CoA:ACP transacylase; fabD), then β-ketoacyl-ACP synthase III (fabH) initiates condensation of malonyl-ACP with acetyl-CoA. Elongation cycles begin with the condensation of malonyl-ACP and an acyl-ACP catalyzed by β-ketoacyl-ACP synthase I (fabB) and β-ketoacyl-ACP synthase II (fabF) to produce a β-keto-acyl-ACP, then the β-keto-acyl-ACP is reduced by a NADPH-dependent β-ketoacyl-ACP reductase (fabG) to produce a β-hydroxy-acyl-ACP, which is dehydrated to a trans-2-enoyl-acyl-ACP by β-hydroxyacyl-ACP dehydratase (fabA or fabZ). FabA can also isomerize trans-2-enoyl-acyl-ACP to cis-3-enoyl-acyl-ACP, which can bypass fabI and can used by fabB (typically for up to an aliphatic chain length of C16) to produce β-keto-acyl-ACP. The final step in each cycle is catalyzed by a NADH or NADHPH-dependent enoyl-ACP reductase (fabI) that converts trans-2-enoyl-acyl-ACP to acyl-ACP. In the methods described herein, termination of fatty acid synthesis occurs by thioesterase removal of the acyl group from acyl-ACP to release free fatty acids (FFA). Thioesterases (e.g., tesA) hydrolyze thioester bonds, which occur between acyl chains and ACP through sulfhydryl bonds.

There are conflicting speculations in the art as to the limiting factors of fatty acid biosynthesis in host cells, such as *E. coli*. One approach to increasing the flux through fatty acid biosynthesis is to manipulate various enzymes in the pathway (FIGS. 1 and 2). The supply of acyl-ACPs from acetyl-CoA via the acetyl-CoA carboxylase (acc) complex (FIG. 3) and fatty acid biosynthetic (fab) pathway may limit the rate of fatty alcohol production. In one exemplary approach detailed in Example 2, the effect of overexpression of *Corynebacterium glutamicum* accABCD (±birA) demonstrated that such genetic modifications can lead to increased acetyl-coA and malonyl-CoA in *E. coli*. One possible reason for a low rate of flux through fatty acid biosynthesis is a limited supply of precursors, namely acetyl-CoA and, in particular, malonyl-CoA, and the main precursors for fatty acid biosynthesis. Example 3 describes the construction of fab operons that encode enzymes in the biosynthetic pathway for conversion of malonyl-CoA into acyl-ACPs and integration into the chromosome of an *E. coli* host cell. In yet another approach detailed in Example 4, mutations in the rph and ilvG genes in the *E. coli* host cell were shown to result in higher free fatty acid (FFA) production, which translated into higher production of fatty alcohol. In still another approach, transposon mutagenesis and high-throughput screening was done to find beneficial mutations that increase the titer or yield. Example 5 describes how a transposon insertion in the yijP gene can improve the fatty alcohol yield in shake flask and fed-batch fermentations.

Carboxylic Acid Reductase (CAR)

Recombinant host cells have been engineered to produce fatty alcohols by expressing a thioesterase, which catalyzes the conversion of acyl-ACPs into free fatty acids (FFAs) and a carboxylic acid reductase (CAR), which converts free fatty acids into fatty aldehydes. Native (endogenous) aldehyde reductases present in the host cell (e.g., *E. coli*) can convert fatty aldehydes into fatty alcohols. Exemplary thioesterases are described for example in US Patent Publication No. 20100154293, expressly incorporated by reference herein. CarB, is an exemplary carboxylic acid reductase, a key enzyme in the fatty alcohol production pathway. WO2010/062480 describes a BLAST search using the NRRL 5646 CAR amino acid sequence (Genpept accession AAR91681)

(SEQ ID NO: 6) as the query sequence, and use thereof in identification of approximately 20 homologous sequences.

The terms "carboxylic acid reductase," "CAR," and "fatty aldehyde biosynthetic polypeptide" are used interchangeably herein. In practicing the disclosure, a gene encoding a carboxylic acid reductase polypeptide is expressed or overexpressed in the host cell. In some embodiments, the CarB polypeptide has the amino acid sequence of SEQ ID NO: 7. In other embodiments, the CarB polypeptide is a variant or mutant of SEQ ID NO: 7. In certain embodiments, the CarB polypeptide is from a mammalian cell, plant cell, insect cell, yeast cell, fungus cell, filamentous fungi cell, a bacterial cell, or any other organism. In some embodiments, the bacterial cell is a *mycobacterium* selected from the group consisting of *Mycobacterium smegmatis*, *Mycobacterium abscessus*, *Mycobacterium avium*, *Mycobacterium bovis*, *Mycobacterium tuberculosis*, *Mycobacterium leprae*, *Mycobacterium marinum*, and *Mycobacterium ulcerans*. In other embodiments, the bacterial cell is from a *Nocardia* species, for example, *Nocardia* NRRL 5646, *Nocardia farcinica*, *Streptomyces griseus*, *Salinispora arenicola*, or *Clavibacter michiganenesis*. In other embodiments, the CarB polypeptide is a homologue of CarB having an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 7. The identity of a CarB polypeptide having at least about 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 7 is not particularly limited, and one of ordinary skill in the art can readily identify homologues of *E. coli* MG1655 derived-CarB and determine its function using the methods described herein. In other embodiments, the CarB polypeptide contains a mutation at amino acid number 3, 12, 20, 28, 46, 74, 103, 191, 288, 473, 827, 926, 927, 930 or 1128 of SEQ ID NO: 7. Exemplary mutations are detailed in Table 10. Preferred fragments or mutants of a polypeptide retain some or all of the biological function (e.g., enzymatic activity) of the corresponding wild-type polypeptide. In some embodiments, the fragment or mutant retains at least about 75%, at least about 80%, at least about 90%, at least about 95%, or at least about 98% or more of the biological function of the corresponding wild-type polypeptide. In other embodiments, the fragment or mutant retains about 100% of the biological function of the corresponding wild-type polypeptide. Guidance in determining which amino acid residues may be substituted, inserted, or deleted without affecting biological activity may be found using computer programs well known in the art, for example, LASER-GENE™ software (DNASTAR, Inc., Madison, Wis.).

In yet other embodiments, a fragment or mutant exhibits increased biological function as compared to a corresponding wild-type polypeptide. For example, a fragment or mutant may display at least about a 10%, at least about a 25%, at least about a 50%, at least about a 75%, or at least about a 90% improvement in enzymatic activity as compared to the corresponding wild-type polypeptide. In other embodiments, the fragment or mutant displays at least about 100% (e.g., at least about 200%, or at least about 500%) improvement in enzymatic activity as compared to the corresponding wild-type polypeptide. It is understood that the polypeptides described herein may have additional conservative or non-essential amino acid substitutions, which do not have a substantial effect on the polypeptide function. Whether or not a particular substitution will be tolerated (i.e., will not adversely affect desired biological function, such as DNA binding or enzyme activity) can be determined as described in Bowie et al. (*Science*, 247: 1306-1310 (1990)).

As a result of the methods and variant enzymes of the present disclosure, one or more of the titer, yield, and/or productivity of the fatty acid or derivative thereof produced by the engineered host cell having an altered level of expression of a CarB polypeptide is increased relative to that of the corresponding wild-type host cell. To allow for maximum conversion of C12 and C14 fatty acids into fatty alcohols, CarB must be expressed at sufficient activity. An improved recombinant host cell would have a CAR enzyme that is expressed from, for example, the *E. coli* chromosome. As shown in Example 6, cells expressing the CarB enzyme from the chromosome have more carboxylic acid reductase activity relative to the original CarB and are able to convert more C12 and C14 fatty acids into fatty alcohols. CarB is a large gene (3.5 kb) and increases plasmid size considerably, making it difficult to use a pCL plasmid to test new genes during strain development. Approaches to increasing the activity of CarB, include increasing its solubility, stability, expression and/or functionality. In one exemplary approach, a fusion protein that contains 6 histidines and a thrombin cleavage site at the N-terminus of CarB is produced. This enzyme differs from CarB by an additional 60 nucleotides at the N-terminus, and is named CarB60. When CarB or CarB60 are expressed from the *E. coli* chromosome under control of the pTRC promoter, cells containing CarB60 have increased total cellular carboxylic acid reductase activity and convert more C12 and C14 free fatty acids (FFAs) into fatty alcohols. One of skill in the art will appreciate that this is one example of molecular engineering in order to achieve a greater conversion of C12 and C14 free fatty acids (FFAs) into fatty alcohols as illustrated in Example 6 (supra). Similar approaches are encompassed herein (see Example 7).

Phosphopantetheine transferases (PPTases) (EC 2.7.8.7) catalyze the transfer of 4'-phosphopantetheine from CoA to a substrate. *Nocardia* Car, CarB and several homologues thereof contain a putative attachment site for 4'-phosphopantetheine (PPT) (He et al., *Appl. Environ. Microbiol.*, 70(3): 1874-1881 (2004)). In some embodiments of the disclosure, a PPTase is expressed or overexpressed in an engineered host cell. In certain embodiments, the PPTase is EntD from *E. coli* MG1655 (SEQ ID NO:8). In some embodiments, a thioesterase and a carboxylic acid reductase are expressed or overexpressed in an engineered host cell. In certain embodiments, the thioesterase is tesA and the carboxylic acid reductase is carB. In other embodiments, a thioesterase, a carboxylic acid reductase and an alcohol dehydrogenase are expressed or overexpressed in an engineered host cell. In certain embodiments, the thioesterase is tesA, the carboxylic acid reductase is carB and the alcohol dehydrogenase is alrAadp1 (GenPept accession number CAG70248.1) from *Acinetobacter baylyi* ADP1 (SEQ ID NO: 4). In still other embodiments, a thioesterase, a carboxylic acid reductase, a PPTase, and an alcohol dehydrogenase are expressed or overexpressed in the engineered host cell. In certain embodiments, the thioesterase is tesA, the carboxylic acid reductase is carB, the PPTase is entD, and the alcohol dehydrogenase is alrAadp1. In still further embodiments, a modified host cell which expresses one or more of a thioesterase, a CAR, a PPTase, and an alcohol dehydrogenase also has one or more strain improvements. Exemplary strain improvements include, but are not limited to expression or overexpression of an acetyl-CoA carboxylase polypeptide, overexpression of a FadR polypeptide, expression or overexpression of a heterologous iFAB operon, or transposon insertion in the yijP gene or another gene, or similar approaches. The disclosure also provides a fatty alcohol composition produced by any of the methods described herein. A fatty alcohol composition produced by any of the methods described herein can be used directly as a starting materials for production of other chemical compounds (e.g., polymers, surfactants, plastics, textiles, solvents, adhesives, etc.), or personal care additives. These compounds can also be used as feedstock for subsequent reactions, for example, hydrogenation, catalytic cracking (e.g., via hydrogenation, pyrolisis, or both) to make other products.

Mutants or Variants

In some embodiments, the polypeptide expressed in a recombinant host cell is a mutant or a variant of any of the polypeptides described herein. The terms "mutant" and "variant" as used herein refer to a polypeptide having an amino acid sequence that differs from a wild-type polypeptide by at least one amino acid. For example, the mutant can comprise one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the mutant polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. Preferred fragments or mutants of a polypeptide retain some or all of the biological function (e.g., enzymatic activity) of the corresponding wild-type polypeptide. In some embodiments, the fragment or mutant retains at least about 75%, at least about 80%, at least about 90%, at least about 95%, or at least about 98% or more of the biological function of the corresponding wild-type polypeptide. In other embodiments, the fragment or mutant retains about 100% of the biological function of the corresponding wild-type polypeptide. Guidance in determining which amino acid residues may be substituted, inserted, or deleted without affecting biological activity may be found using computer programs well known in the art, for example, LASERGENE™ software (DNASTAR, Inc., Madison, Wis.).

In yet other embodiments, a fragment or mutant exhibits increased biological function as compared to a corresponding wild-type polypeptide. For example, a fragment or mutant may display at least a 10%, at least a 25%, at least a 50%, at least a 75%, or at least a 90% improvement in enzymatic activity as compared to the corresponding wild-type polypeptide. In other embodiments, the fragment or mutant displays at least 100% (e.g., at least 200%, or at least 500%) improvement in enzymatic activity as compared to the corresponding wild-type polypeptide. It is understood that the polypeptides described herein may have additional conservative or non-essential amino acid substitutions, which do not have a substantial effect on the polypeptide function. Whether or not a particular substitution will be tolerated (i.e., will not adversely affect desired biological function, such as carboxylic acid reductase activity) can be determined as described in Bowie et al. (*Science*, 247: 1306-1310 (1990)). A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Variants can be naturally occurring or created in vitro. In particular, such variants can be created using genetic engineering techniques, such as site directed mutagenesis, random chemical mutagenesis, Exonuclease III deletion procedures, or standard cloning techniques. Alternatively, such variants, fragments, analogs, or derivatives can be created using chemical synthesis or modification procedures.

Methods of making variants are well known in the art. These include procedures in which nucleic acid sequences obtained from natural isolates are modified to generate nucleic acids that encode polypeptides having characteristics that enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates. For example, variants can be prepared by using random and site-directed mutagenesis. Random and site-directed mutagenesis are described in, for example, Arnold, *Curr. Opin. Biotech.*, 4: 450-455 (1993). Random mutagenesis can be achieved using error prone PCR (see, e.g., Leung et al., *Technique*, 1: 11-15 (1989); and Caldwell et al., *PCR Methods Applic.*, 2: 28-33 (1992)). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized (e.g., a polynucleotide sequence encoding a carboxylic reductase enzyme) are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector, and the activities of the polypeptides encoded by the mutagenized nucleic acids are evaluated (see Example 7). Site-directed mutagenesis can be achieved using oligonucleotide-directed mutagenesis to generate site-specific mutations in any cloned DNA of interest. Oligonucleotide mutagenesis is described in, for example, Reidhaar-Olson et al., *Science*, 241: 53-57 (1988). Briefly, in such procedures a plurality of double stranded oligonucleotides bearing one or more mutations to be introduced into the cloned DNA are synthesized and inserted into the cloned DNA to be mutagenized (e.g., a polynucleotide sequence encoding a CAR polypeptide). Clones containing the mutagenized DNA are recovered, and the activities of the polypeptides they encode are assessed. Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408. Still another method of generating variants is sexual PCR mutagenesis. In sexual PCR mutagenesis, forced homologous recombination occurs between DNA molecules of different, but highly related, DNA sequences in vitro as a result of random fragmentation of the DNA molecule based on sequence homology. This is followed by fixation of the crossover by primer extension in a PCR reaction. Sexual PCR mutagenesis is described in, for example, Stemmer, *Proc. Natl. Acad. Sci., U.S.A.,* 91: 10747-10751 (1994).

Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence (e.g., a polynucleotide sequence encoding a CAR polypeptide) in one of these strains will eventually generate random mutations within the DNA. Mutator strains suitable for use for in vivo mutagenesis are described in, for example, International Patent Application Publication No. WO1991/016427. Variants can also be generated using cassette mutagenesis. In cassette mutagenesis, a small region of a double-stranded DNA molecule is replaced with a synthetic oligonucleotide "cassette" that differs from the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., *Proc. Natl. Acad. Sci., U.S.A.,* 89: 7811-7815 (1992). In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., *Biotech. Res,* 11: 1548-1552 (1993). In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250.

Insertional mutagenesis is mutagenesis of DNA by the insertion of one or more bases. Insertional mutations can occur naturally, mediated by virus or transposon, or can be artificially created for research purposes in the lab, e.g., by transposon mutagenesis. When exogenous DNA is integrated into that of the host, the severity of any ensuing mutation depends entirely on the location within the host's genome wherein the DNA is inserted. For example, significant effects may be evident if a transposon inserts in the middle of an essential gene, in a promoter region, or into a repressor or an enhancer region. Transposon mutagenesis and high-throughput screening was done to find beneficial mutations that increase the titer or yield of fatty alcohol. The disclosure provides recombinant host cells comprising (a) a polynucleotide sequence encoding a carboxylic acid reductase comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO: 7 and (b) a polynucleotide encoding a polypeptide having carboxylic acid reductase activity, wherein the recombinant host cell is capable of producing a fatty aldehyde or a fatty alcohol.

Engineering Host Cells

In some embodiments, a polynucleotide (or gene) sequence is provided to a host cell by way of a recombinant vector, which comprises a promoter operably linked to the polynucleotide sequence. In certain embodiments, the promoter is a developmentally-regulated, an organelle-specific, a tissue-specific, an inducible, a constitutive, or a cell-specific promoter. In some embodiments, the recombinant vector includes (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences described herein. Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech, Inc., Piscataway, N.J.; Smith et al., *Gene,* 67: 31-40 (1988)), pMAL (New England Biolabs, Beverly, Mass.), and pRITS (Pharmacia Biotech, Inc., Piscataway, N.J.), which fuse glutathione S-transferase (GST), maltose E binding protein, or protein A, respectively, to the target recombinant polypeptide.

Examples of inducible, non-fusion *E. coli* expression vectors include pTrc (Amann et al., *Gene* (1988) 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter. Suitable expression systems for both prokaryotic and eukaryotic cells are well known in the art; see, e.g., Sambrook et al., "Molecular Cloning: A Laboratory Manual," second edition, Cold Spring Harbor Laboratory, (1989). Examples of inducible, non-fusion *E. coli* expression vectors include pTrc (Amann et al., *Gene*, 69: 301-315 (1988)) and PET 11d (Studier et al., Gene Expression Technology: Methods in Enzymology 185, Academic Press, San Diego, Calif., pp. 60-89 (1990)). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra). For stable transformation of bacterial cells, it is known that, depending upon the expression vector and transformation technique used, only a small fraction of cells will take-up and replicate the expression vector. In some embodiments, in order to identify and select these transformants, a gene that encodes a selectable marker (e.g., resistance to an antibiotic) is introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug.

Production of Fatty Alcohol Compositions by Recombinant Host Cells

Strategies to increase production of fatty alcohols by recombinant host cells include increased flux through the fatty acid biosynthetic pathway by overexpression of native fatty acid biosynthesis genes and expression of exogenous fatty acid biosynthesis genes from different organisms in an engineered production host. Enhanced activity of relevant enzymes in the fatty alcohol biosynthetic pathway, e.g., CAR, as well as other strategies to optimize the growth and productivity of the host cell may also be employed to maximize production. In some embodiments, the recombinant host cell comprises a polynucleotide encoding a polypeptide (an enzyme) having fatty alcohol biosynthetic activity (i.e., a fatty alcohol biosynthetic polypeptide or a fatty alcohol biosynthetic enzyme), and a fatty alcohol is produced by the recombinant host cell. A composition comprising fatty alcohols (a fatty alcohol composition) may be produced by culturing the recombinant host cell in the presence of a carbon source under conditions effective to express a fatty alcohol biosynthetic enzyme. In some embodiments, the fatty alcohol composition comprises fatty alcohols, however, a fatty alcohol composition may comprise other fatty acid derivatives. Typically, the fatty alcohol composition is recovered from the extracellular environment of the recombinant host cell, i.e., the cell culture medium. In one approach, recombinant host cells have been engineered to produce fatty alcohols by expressing a thioesterase, which catalyzes the conversion of acyl-ACPs into free fatty acids (FFAs) and a carboxylic acid reductase (CAR), which converts free fatty acids into fatty aldehydes. Native (endogenous) aldehyde reductases present in the host cell (e.g., *E. coli*) can convert the fatty aldehydes into fatty alcohols. In some embodiments, the fatty alcohol is produced by expressing or overexpressing in the recombinant host cell a polynucleotide encoding a polypeptide having fatty alcohol biosynthetic activity which converts a fatty aldehyde to a fatty alcohol. For example, an alcohol dehydrogenase (also referred to herein as an aldehyde reductase, e.g., EC 1.1.1.1), may be used in practicing the disclosure. As used herein, the term "alcohol dehydrogenase" refers to a polypeptide capable of catalyzing the conversion of a fatty aldehyde to an alcohol (e.g., a fatty alcohol). One of ordinary skill in the art will appreciate that certain alcohol dehydrogenases are capable of catalyzing other reactions as well, and these non-specific alcohol dehydrogenases also are encompassed by the term "alcohol dehydrogenase." Examples of alcohol dehydrogenase polypeptides useful in accordance with the disclosure include, but are not limited to AlrAadp1 (SEQ ID NO: 4) or AlrA homologs and endogenous *E. coli* alcohol dehydrogenases such as YjgB, (AAC77226) (SEQ ID NO: 5), DkgA (NP_417485), DkgB (NP_414743), YdjL (AAC74846), YdjJ (NP_416288), AdhP (NP_415995), YhdH (NP_417719), YahK (NP_414859), YphC (AAC75598), YqhD (446856) and YbbO [AAC73595.1]. Additional examples are described in International Patent Application Publication Nos. WO2007/136762, WO2008/119082 and WO 2010/062480, each of which is expressly incorporated by reference herein. In certain embodiments, the fatty alcohol biosynthetic polypeptide has aldehyde reductase or alcohol dehydrogenase activity (EC 1.1.1.1). In another approach, recombinant host cells have been engineered to produce fatty alcohols by expressing fatty alcohol forming acyl-CoA reductases or fatty acyl reductases (FARs) which convert fatty acyl-thioester substrates (e.g., fatty acyl-CoA or fatty acyl-ACP) to fatty alcohols. In some embodiments, the fatty alcohol is produced by expressing or overexpressing a polynucleotide encoding a polypeptide having fatty alcohol forming acyl-CoA reductase (FAR) activity in a recombinant host cell. Examples of FAR polypeptides useful in accordance with this embodiment are described in PCT Publication No. WO2010/062480, which is expressly incorporated by reference herein.

Fatty alcohol may be produced via an acyl-CoA dependent pathway utilizing fatty acyl-ACP and fatty acyl-CoA intermediates and an acyl-CoA independent pathway utilizing fatty acyl-ACP intermediates but not a fatty acyl-CoA intermediate. In particular embodiments, the enzyme encoded by the over expressed gene is selected from a fatty acid synthase, an acyl-ACP thioesterase, a fatty acyl-CoA synthase and an acetyl-CoA carboxylase. In some embodiments, the protein encoded by the over expressed gene is endogenous to the host cell. In other embodiments, the protein encoded by the overexpressed gene is heterologous to the host cell. Fatty alcohols are also made in nature by enzymes that are able to reduce various acyl-ACP or acyl-CoA molecules to the corresponding primary alcohols. See also, U.S. Patent Publication Nos. 20100105963, and 20110206630 and U.S. Pat. No. 8,097,439, expressly incorporated by reference herein. As used herein, a recombinant host cell or an engineered host cell refers to a host cell whose genetic makeup has been altered relative to the corresponding wild-type host cell, for example, by deliberate introduction of new genetic elements and/or deliberate modification of genetic elements naturally present in the host cell. The offspring of such recombinant host cells also contain these new and/or modified genetic elements. In any of the aspects of the disclosure described herein, the host cell can be selected from the group consisting of a plant cell, insect cell, fungus cell (e.g., a filamentous fungus, such as *Candida* sp., or a budding yeast, such as *Saccharomyces* sp.), an algal cell and a bacterial cell. In one preferred embodiment, recombinant host cells are recombinant microbial cells. Examples of host cells that are microbial cells, include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces*. In some embodiments, the host cell is a Gram-positive bacterial cell. In other embodiments, the host cell is a Gram-negative bacterial cell. In some embodiments, the host cell is an *E. coli* cell. In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell.

In yet other embodiments, the host cell is a *Streptomyces lividans* cell or a *Streptomyces murinus* cell. In yet other embodiments, the host cell is an *Actinomycetes* cell. In some embodiments, the host cell is a *Saccharomyces cerevisiae* cell. In some embodiments, the host cell is a *Saccharomyces cerevisiae* cell. In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Avabidopsis thaliana, Panicum virgatum, Miscanthus giganteus, Zea mays, Botryococceuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridiuthermocellum, Penicillium chrysogenum, Pichia pastoris, Saccharomyces cerevisiae, Schizosaccharomyces pombe, Pseudomonasjluorescens,* or *Zymomonas mobilis*.

Culture and Fermentation of Engineered Host Cells

As used herein, fermentation broadly refers to the conversion of organic materials into target substances by host cells, for example, the conversion of a carbon source by recombinant host cells into fatty acids or derivatives thereof by propagating a culture of the recombinant host cells in a media comprising the carbon source. As used herein, conditions permissive for the production means any conditions that allow a host cell to produce a desired product, such as a fatty acid or a fatty acid derivative. Similarly, conditions in which the polynucleotide sequence of a vector is expressed means any conditions that allow a host cell to synthesize a polypeptide. Suitable conditions include, for example, fermentation conditions. Fermentation conditions can comprise many parameters, including but not limited to temperature ranges, levels of aeration, feed rates and media composition. Each of these conditions, individually and in combination, allows the host cell to grow. Fermentation can be aerobic, anaerobic, or variations thereof (such as microaerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source. For small scale production, the engineered host cells can be grown in batches of, for example, about 100 mL, 500 mL, 1 L, 2 L, 5 L, or 10 L; fermented; and induced to express a desired polynucleotide sequence, such as a polynucleotide sequence encoding a CAR polypeptide. For large scale production, the engineered host cells can be grown in batches of about 10 L, 100 L, 1000 L, 10,000 L, 100,000 L, 1,000,000 L or larger; fermented; and induced to express a desired polynucleotide sequence. Alternatively, large scale fed-batch fermentation may be carried out.

Fatty Alcohol Compositions

The fatty alcohol compositions described herein are found in the extracellular environment of the recombinant host cell culture and can be readily isolated from the culture medium. A fatty alcohol composition may be secreted by the recombinant host cell, transported into the extracellular environment or passively transferred into the extracellular environment of the recombinant host cell culture. The fatty alcohol composition is isolated from a recombinant host cell culture using routine methods known in the art. The disclosure provides compositions produced by engineered or recombinant host cells (bioproducts) which include one or more fatty aldehydes and/or fatty alcohols. Although a fatty alcohol component with a particular chain length and degree of saturation may constitute the majority of the bioproduct produced by a cultured engineered or recombinant host cell, the composition typically includes a mixture of fatty aldehydes and/or fatty alcohols that vary with respect to chain length and/or degree of saturation. As used herein, fraction of modern carbon or $f_M$ has the same meaning as defined by National Institute of Standards and Technology (NIST) Standard Reference Materials (SRMs 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

Bioproducts (e.g., the fatty aldehydes and alcohols produced in accordance with the present disclosure) comprising biologically produced organic compounds, and in particular, the fatty aldehydes and alcohols biologically produced using the fatty acid biosynthetic pathway herein, have not been produced from renewable sources and, as such, are new compositions of matter. These new bioproducts can be distinguished from organic compounds derived from petrochemical carbon on the basis of dual carbon-isotopic fingerprinting or $^{14}$C dating. Additionally, the specific source of biosourced carbon (e.g., glucose vs. glycerol) can be determined by dual carbon-isotopic fingerprinting (see, e.g., U.S. Pat. No. 7,169,588, which is herein incorporated by reference). The ability to distinguish bioproducts from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the bioproducts herein can be followed or tracked in commerce on the basis of their unique carbon isotope profile. Bioproducts can be distinguished from petroleum based organic compounds by comparing the stable carbon isotope ratio ($^{13}$C/$^{12}$C) in each fuel. The $^{13}$C/$^{12}$C ratio in a given bioproduct is a consequence of the $^{13}$C/$^{12}$C ratio in atmospheric carbon dioxide at the time the carbon dioxide is fixed. It also reflects the precise metabolic pathway. Regional variations also occur. Petroleum, $C_3$ plants (the broadleaf), $C_4$ plants (the grasses), and marine carbonates all show significant differences in $^{13}$C/$^{12}$C and the corresponding $\delta^{13}$C values. Furthermore, lipid matter of $C_3$ and $C_4$ plants analyze differently than materials derived from the carbohydrate components of the same plants as a consequence of the metabolic pathway. Within the precision of measurement, $^{13}$C shows large variations due to isotopic fractionation effects, the most significant of which for bioproducts is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the $C_3$ (or Calvin-Benson) photosynthetic cycle and those that incorporate the $C_4$ (or Hatch-Slack) photosynthetic cycle. In $C_3$ plants, the primary $CO_2$ fixation or carboxylation reaction involves the enzyme ribulose-1,5-diphosphate carboxylase, and the first stable product is a 3-carbon compound. $C_3$ plants, such as hardwoods and conifers, are dominant in the temperate climate zones. In $C_4$ plants, an additional carboxylation reaction involving another enzyme, phosphoenol-pyruvate carboxylase, is the primary carboxylation reaction. The first stable carbon compound is a 4-carbon acid that is subsequently decarboxylated. The $CO_2$ thus released is refixed by the $C_3$ cycle. Examples of $C_4$ plants are tropical grasses, corn, and sugar cane. Both $C_4$ and $C_3$ plants exhibit a range of $^{13}$C/$^{12}$C isotopic ratios, but typical values are about −7 to about −13 per mil for $C_4$ plants and about −19 to about −27 per mil for $C_3$ plants (see, e.g., Stuiver et al., *Radiocarbon* 19:355 (1977)). Coal and petroleum fall generally in this latter range. The $^{13}$C measurement scale was originally defined by a zero set by Pee Dee Belemnite (PDB) limestone, where values are given in parts per thousand deviations from this material. The "$\delta^{13}$C" values are expressed in parts per thousand (per mil), abbreviated, ‰, and are calculated as follows:

$$\delta^{13}C(‰)=[(^{13}C/^{12}C)_{sample}-(^{13}C/^{12}C)_{standard}]/(^{13}C/^{12}C)_{standard}\times 1000$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}$C. Measurements are made on $CO_2$ by high precision stable ratio mass spectrometry (IRMS) on molecular ions of masses 44, 45, and 46. The compositions described herein include bioproducts produced by any of the methods described herein, including, for example, fatty aldehyde and alcohol products. Specifically, the bioproduct can have a $\delta^{13}$C of about −28 or greater, about −27 or greater, −20 or greater, −18 or greater, −15 or greater, −13 or greater, −10 or greater, or −8 or greater. For example, the bioproduct can have a $\delta^{13}$C of about −30 to about −15, about −27 to about −19, about −25 to about −21, about −15 to about −5, about −13 to about −7, or about −13 to about −10. In other instances, the bioproduct can have a $\delta^{13}$C of about −10, −11, −12, or −12.3. Bioproducts, including the bioproducts produced in accordance with the disclosure herein, can also be distinguished from petroleum based organic compounds by comparing the amount of $^{14}$C in each compound. Because $^{14}$C has a nuclear half-life of 5730 years, petroleum based fuels containing "older" carbon can be distinguished from bioproducts which contain "newer" carbon (see, e.g., Currie, "Source Apportionment of Atmospheric Particles", *Characterization of Environmental Particles*, J. Buffle and H. P. van Leeuwen, Eds., 1 of Vol. I of the IUPAC Environmental Analytical Chemistry Series (Lewis Publishers, Inc.) 3-74, (1992)).

The basic assumption in radiocarbon dating is that the constancy of $^{14}$C concentration in the atmosphere leads to the constancy of $^{14}$C in living organisms. However, because of atmospheric nuclear testing since 1950 and the burning of fossil fuel since 1850, $^{14}$C has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}$C/$^{12}$C) of about $1.2\times10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}$C since the onset of the nuclear age.) It is this latter biospheric $^{14}$C time characteristic that holds out the promise of annual dating of recent biospheric carbon. $^{14}$C can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C. As used herein, fraction of modern carbon ($f_M$) has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}$C/$^{12}$C isotope ratio HOxI (referenced to AD 1950). This is roughly equivalent to decay-corrected pre-Industrial Revolution wood. For the current living biosphere (plant material), $f_M$ is approximately 1.1. This is roughly equivalent to decay-corrected pre-Industrial Revolution wood. For the current living biosphere (plant material), $f_M$ is approximately 1.1.

The compositions described herein include bioproducts that can have an $f_M$ $^{14}C$ of at least about 1. For example, the bioproduct of the disclosure can have an $f_M$ $^{14}C$ of at least about 1.01, an $f_M$ $^{14}C$ of about 1 to about 1.5, an $f_M$ $^{14}C$ of about 1.04 to about 1.18, or an $f_M$ $^{14}C$ of about 1.111 to about 1.124. Another measurement of $^{14}C$ is known as the percent of modern carbon (pMC). For an archaeologist or geologist using $^{14}C$ dates, AD 1950 equals "zero years old". This also represents 100 pMC. "Bomb carbon" in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty aldehydes or alcohols as described herein can have a pMC of at least about 50, 60, 70, 75, 80, 85, 90, 95, 96, 97, 98, 99, or 100. In other instances, a bioproduct described herein can have a pMC of between about 50 and about 100; about 60 and about 100; about 70 and about 100; about 80 and about 100; about 85 and about 100; about 87 and about 98; or about 90 and about 95. In yet other instances, a bioproduct described herein can have a pMC of about 90, 91, 92, 93, 94, or 94.2.

Screening Fatty Alcohol Compositions Produced by Recombinant Host Cell

To determine if conditions are sufficient to allow expression, a recombinant host cell comprising a heterologous gene or a modified native gene is cultured, for example, for about 4, 8, 12, 24, 36, or 48 hours. During and/or after culturing, samples can be obtained and analyzed to determine if the fatty alcohol production level (titer, yield or productivity) is different than that of the corresponding wild type parental cell which has not been modified. For example, the medium in which the host cells were grown can be tested for the presence of a desired product. When testing for the presence of a product, assays, such as, but not limited to, TLC, HPLC, GC/FID, GC/MS, LC/MS, MS, can be used. Recombinant host cell strains can be cultured in small volumes (0.001 L to 1 L) of media in plates or shake flasks in order to screen for altered fatty alcohol or fatty species production level. Once candidate strains or "hits" are identified at small scale, these strains are cultured in larger volumes (1 L to 1000 L) of media in bioreactors, tanks, and pilot plants to determine the precise fatty alcohol or fatty species production level. These large volume culture conditions are used by those skilled in the art to optimize the culture conditions to obtain desired fatty alcohol or fatty species production.

Utility of Fatty Aldehyde and Fatty Alcohol Compositions

Aldehydes are used to produce many specialty chemicals. For example, aldehydes are used to produce polymers, resins (e.g., Bakelite), dyes, flavorings, plasticizers, perfumes, pharmaceuticals, and other chemicals, some of which may be used as solvents, preservatives, or disinfectants. In addition, certain natural and synthetic compounds, such as vitamins and hormones, are aldehydes, and many sugars contain aldehyde groups. Fatty aldehydes can be converted to fatty alcohols by chemical or enzymatic reduction. Fatty alcohols have many commercial uses. Worldwide annual sales of fatty alcohols and their derivatives are in excess of U.S. $1 billion. The shorter chain fatty alcohols are used in the cosmetic and food industries as emulsifiers, emollients, and thickeners. Due to their amphiphilic nature, fatty alcohols behave as nonionic surfactants, which are useful in personal care and household products, such as, for example, detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats. The disclosure also provides a surfactant composition or a detergent composition comprising a fatty alcohol produced by any of the methods described herein. One of ordinary skill in the art will appreciate that, depending upon the intended purpose of the surfactant or detergent composition, different fatty alcohols can be produced and used. For example, when the fatty alcohols described herein are used as a feedstock for surfactant or detergent production, one of ordinary skill in the art will appreciate that the characteristics of the fatty alcohol feedstock will affect the characteristics of the surfactant or detergent composition produced. Hence, the characteristics of the surfactant or detergent composition can be selected for by producing particular fatty alcohols for use as a feedstock. A fatty alcohol-based surfactant and/or detergent composition described herein can be mixed with other surfactants and/or detergents well known in the art. In some embodiments, the mixture can include at least about 10%, at least about 15%, at least about 20%, at least about 30%, at least about 40%, at least about 50%, at least about 60%, or a range bounded by any two of the foregoing values, by weight of the fatty alcohol. In other examples, a surfactant or detergent composition can be made that includes at least about 5%, at least about 10%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of a fatty alcohol that includes a carbon chain that is 8, 9, 10, 11, 12, 13, 14, 15, 16, 17, 18, 19, 20, 21, or 22 carbons in length. Such surfactant or detergent compositions also can include at least one additive, such as a microemulsion or a surfactant or detergent from nonmicrobial sources such as plant oils or petroleum, which can be present in the amount of at least about 5%, at least about 10%, at least about 15%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of the fatty alcohol. The disclosure is further illustrated by the following examples. The examples are provided for illustrative purposes only. They are not to be construed as limiting the scope or content of the disclosure in any way.

EXAMPLES

Example 1

Production Host Modifications—Attenuation of Acyl-CoA Dehydrogenase

This example describes the construction of a genetically engineered host cell wherein the expression of a fatty acid degradation enzyme is attenuated. The fadE gene of *Escherichia coli* MG1655 (an *E. coli* K strain) was deleted using the Lambda Red (also known as the Red-Driven Integration) system described by Datsenko et al., Proc. Natl. Acad. Sci. USA 97: 6640-6645 (2000), with the following modifications:

The following two primers were used to create the deletion of fadE:

```
Del-fadE-
                                          (SEQ ID NO: 9)
F5'-AAAAACAGCAACAATGTGAGCTTTGTTGTAATTATATTGTAAACAT ATTGATTCCGGGGATCCGTCGACC;
and Del-fadE-
                                         (SEQ ID NO: 10)
R5'-AAACGGAGCCTTTCGGCTCCGTTATTCATTTACGCGGCTTCAACTT

TCCTGTAGGCTGGAGCTGCTTC
```

The Del-fadE-F and Del-fadE-R primers were used to amplify the kanamycin resistance (KmR) cassette from plasmid pKD13 (described by Datsenko et al., supra) by PCR. The PCR product was then used to transform electro-competent *E. coli* MG1655 cells containing pKD46 (described in Datsenko et al., supra) that had been previously induced with arabinose for 3-4 hours. Following a 3-hour outgrowth in a super optimal broth with catabolite repression (SOC) medium at 37° C., the cells were plated on Luria agar plates containing 50 μg/mL of Kanamycin. Resistant colonies were identified and isolated after an overnight incubation at 37° C. Disruption of the fadE gene was confirmed by PCR amplification using primers fadE-L2 and fadE-R1, which were designed to flank the *E. coli* fadE gene.

The fadE deletion confirmation primers were:

```
                                         (SEQ ID NO: 11)
    fadE-L2 5'-CGGGCAGGTGCTATGACCAGGAC;
and (SEQ ID NO: 12)
    fadE-R1 5'-CGCGGCGTTGACCGGCAGCCTGG
```

Figure 5:
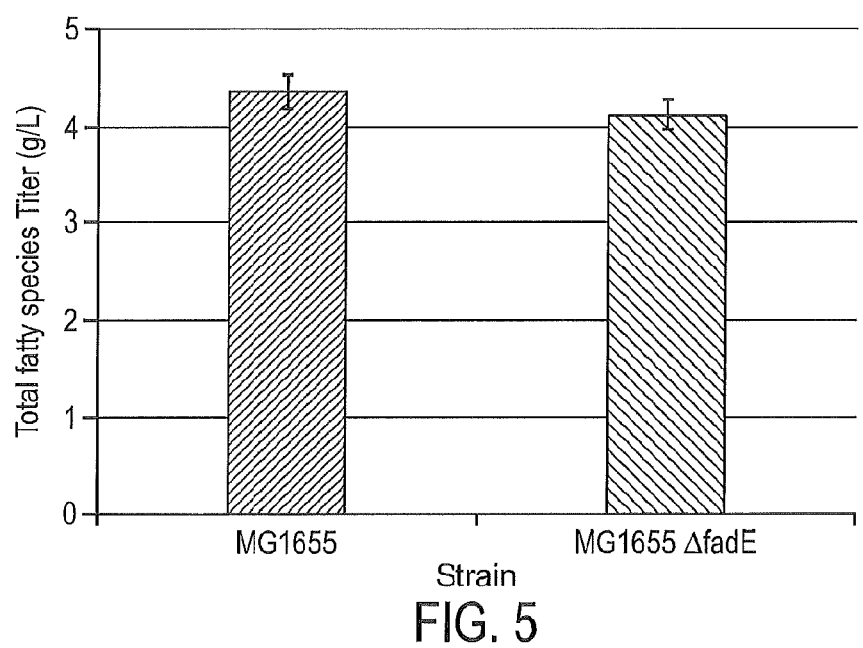
FIG. 5 illustrates fatty acid derivative (Total Fatty Species) production by the MG1655 E. coli strain with the fadE gene attenuated (i.e., deleted) compared to fatty acid derivative production by E. coli MG1655. The data presented in FIG. 5 shows that attenuation of the fadE gene did not affect fatty acid derivative production.

After the fadE deletion was confirmed, a single colony was used to remove the KmR marker using the pCP20 plasmid as described by Datsenko et al., supra. The resulting MG1655 *E. coli* strain with the fadE gene deleted and the KmR marker removed was named *E. coli* MG1655 ΔfadE, or *E. coli* MG 1655 D1. Fatty acid derivative ("Total Fatty Species") production by the MG1655 *E. coli* strain with the fadE gene deleted was compared to fatty acid derivative production by *E. coli* MG1655. Cells were transformed with production plasmid pDG109 (pCL1920_P$_{TRC}$_carBopt_12H08_alrAadp1_fabB[A329G]_ fadR) and fermented in glucose minimal media. The data presented in FIG. 5 shows that deletion of the fadE gene did not affect fatty acid derivative production.

Example 2

Figure 3:
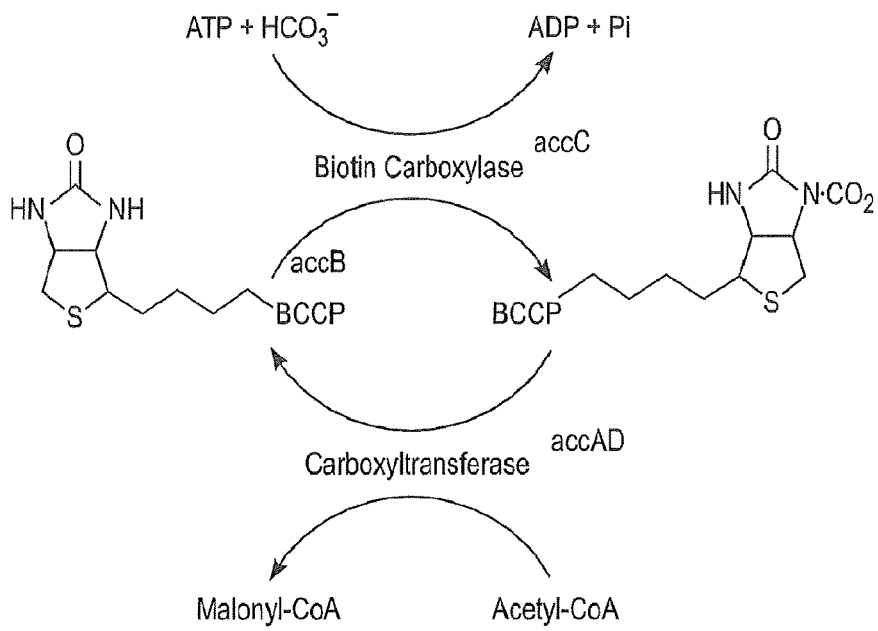
FIG. 3 illustrates the structure and function of the acetyl-CoA carboxylase (accABCD) enzyme complex. Biotin carboxylase is encoded by the accC gene, whereas biotin carboxyl carrier protein (BCCP) is encoded by the accB gene. The two subunits involved in carboxyltransferase activity are encoded by the accA and accD genes. The covalently bound biotin of BCCP carries the carboxylate moiety. The birA gene (not shown) biotinylates holo-accB.
Figure 4:
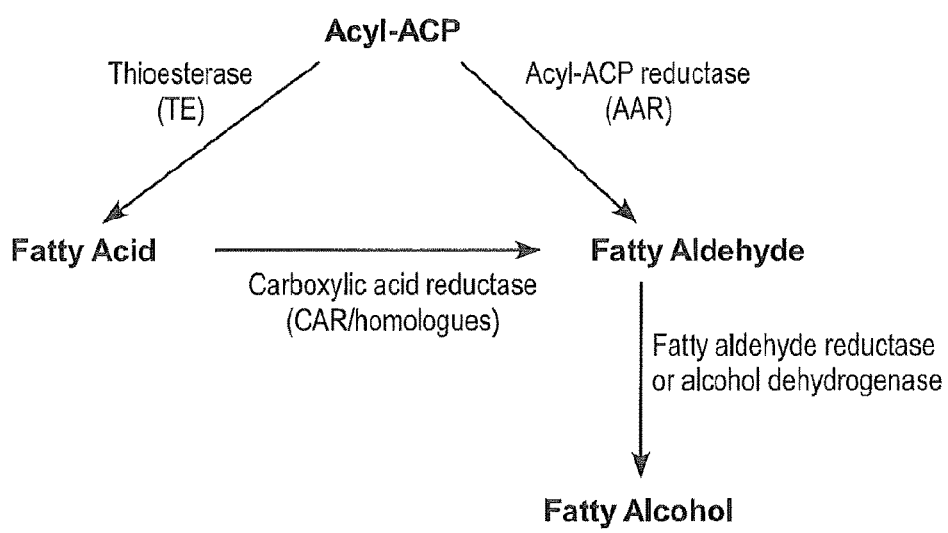
FIG. 4 presents a schematic overview of an exemplary biosynthetic pathway for production of fatty alcohol starting with acyl-ACP, where the production of fatty aldehyde is catalyzed by the enzymatic activity of acyl-ACP reductase (AAR) or thioesterase and carboxylic acid reductase (Car). The fatty aldehyde is converted to fatty alcohol by aldehyde reductase (also referred to as alcohol dehydrogenase). This pathway does not include fatty acyl CoA synthetase (fadD).

Increased Flux Through the Fatty Acid Synthesis Pathway—Acetyl CoA Carboxylase Mediated The main precursors for fatty acid biosynthesis are malonyl-CoA and acetyl-CoA (FIG. 1). It has been suggested that these precursors limit the rate of fatty acid biosynthesis (FIG. 2) in *E. coli*. In this example, synthetic acc operons [*Corynebacterium glutamicum* accABCD (±birA)] were overexpressed and the genetic modifications led to increased acetyl-coA and malonyl-CoA production in *E. coli*. In one approach, in order to increase malonyl-CoA levels, an acetyl-CoA carboxylase enzyme complex from *Corynebacterium glutamicum* (*C. glutamicum*) was overexpressed in *E. coli*. Acetyl-CoA carboxylase (acc) consists of four discrete subunits, accA, accB, accC and accD (FIG. 3). The advantage of *C. glutamicum* acc is that two subunits are expressed as fusion proteins, accCB and accDA, respectively, which facilitates its balanced expression. Additionally, *C. glutamicum* birA, which biotinylates the accB subunit (FIG. 3) was overexpressed. Example 3 describes co-expression of acc genes together with entire fab operons.

Example 3

Increased Flux Through the Fatty Acid Synthesis Pathway—iFABs

Fatty Acid Derivative Production:

Strategies to increase the flux through the fatty acid synthesis pathway in recombinant host cells include both overexpression of native *E. coli* fatty acid biosynthesis genes and expression of exogenous fatty acid biosynthesis genes from different organisms in *E. coli*. In this study, fatty acid biosynthesis genes from different organisms were combined in the genome of *E. coli* DV2. Sixteen strains containing iFABs 130-145 were evaluated. The detailed structure of iFABs 130-145 is presented in iFABs Table 1, below.

TABLE 1

Components found in iFABs 130-145.

| Abbreviation | Full Description |
| --- | --- |
| St_fabD | Salmonella typhimurium fabD gene |
| nSt_fabH | Salmonella typhimurium fabH gene with native RBS |
| sSt_fabH | Salmonella typhimurium fabH gene with synthetic RBS |
| Cac_fabF | Clostridium acetobutylicum (ATCC824) fabF gene |
| St_fabG | Salmonella typhimurium fabG gene |
| St_fabA | Salmonella typhimurium fabA gene |
| St_fabZ | Salmonella typhimurium fabZ gene |
| BS_fabI | Bacillus subtilis fabI gene |
| BS_FabL | Bacillus subtilis fabL gene |
| Vc_FabV | Vibrio cholerae fabV gene |
| Ec_FabI | Escherichia coli fabI gene |

Figure 7A:
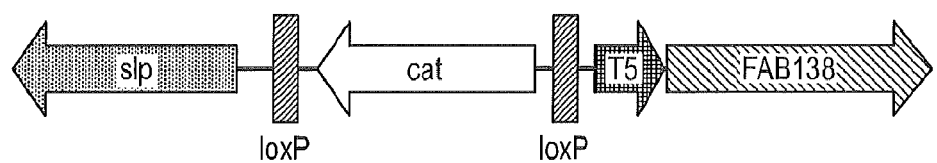
FIGS. 7A and 7B provide a diagrammatic depiction of the iFAB138 locus, including a diagram of cat-loxP-T5 promoter integrated in front of FAB138 (7A); and a diagram of iT5_138 (7B). The sequence of cat-loxP-T5 promoter integrated in front of FAB138 with 50 base pair of homology shown on each side of cat-loxP-T5 promoter region is provided as SEQ ID NO:1 and the sequence of the iT5_138 promoter region with 50 base pair homology on each side is provided as SEQ ID NO: 2.
Figure 7B:
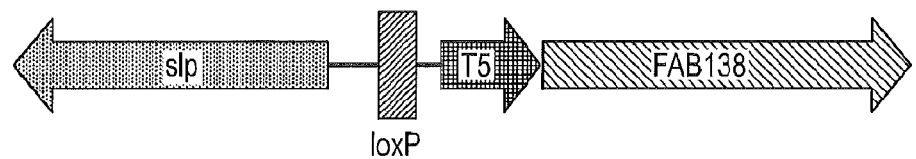

Each "iFAB" included various fab genes in the following order: 1) an enoyl-ACP reductase (BS_fabI, BS_FabL, Vc_FabV, or Ec_FabI); 2) a b-ketoacyl-ACP synthetase III (St_fabH); 3) a malonyl-CoA-ACP transacylase (St_fabD); 4) a b-ketoacyl-ACP reductase (St_fabG); 5) a 3-hydroxy-acyl-ACP dehydratase (St_fabA or St_fabZ); 6) a b-ketoa-cyl-ACP synthetase II (Cac_fabF). Note that St_fabA also has trans-2, cis-3-decenoyl-ACP isomerase activity (ref) and that Cac_fabF has b-ketoacyl-ACP synthetase II and b-ketoacyl-ACP synthetase I activities (Zhu et al., BMC Microbiology 9:119 (2009)). See Table 2, below for the specific composition of iFABs 130-145. See FIGS. 7A and B which provide diagrammatic depiction of the iFAB138 locus, including a diagram of cat-loxP-T5 promoter integrated in front of FAB138 (7A); and a diagram of iT5_138 (7B).

TABLE 2

Composition of iFABs 130-145.

| ifab | BS_fabI | BS_fabL | Vc_fabV | Ec_fabI | nSt_fabH | sSt_fabH | St_fabD | St_fabG | St_fabA | St_fabZ | Cac_fabF |
|---|---|---|---|---|---|---|---|---|---|---|---|
| ifab130 | 1 | 0 | 0 | 0 | 1 | 0 | 1 | 1 | 1 | 0 | 1 |
| ifab131 | 1 | 0 | 0 | 0 | 1 | 0 | 1 | 1 | 0 | 1 | 1 |
| ifab132 | 1 | 0 | 0 | 0 | 0 | 1 | 1 | 1 | 1 | 0 | 1 |
| ifab133 | 1 | 0 | 0 | 0 | 0 | 1 | 1 | 1 | 0 | 1 | 1 |
| ifab134 | 0 | 1 | 0 | 0 | 1 | 0 | 1 | 1 | 1 | 0 | 1 |
| ifab135 | 0 | 1 | 0 | 0 | 1 | 0 | 1 | 1 | 0 | 1 | 1 |
| ifab136 | 0 | 1 | 0 | 0 | 0 | 1 | 1 | 1 | 1 | 0 | 1 |
| ifab137 | 0 | 1 | 0 | 0 | 0 | 1 | 1 | 1 | 0 | 1 | 1 |
| ifab138 | 0 | 0 | 1 | 0 | 1 | 0 | 1 | 1 | 1 | 0 | 1 |
| ifab139 | 0 | 0 | 1 | 0 | 1 | 0 | 1 | 1 | 0 | 1 | 1 |
| ifab140 | 0 | 0 | 1 | 0 | 0 | 1 | 1 | 1 | 1 | 0 | 1 |
| ifab141 | 0 | 0 | 1 | 0 | 0 | 1 | 1 | 1 | 0 | 1 | 1 |
| ifab142 | 0 | 0 | 0 | 1 | 1 | 0 | 1 | 1 | 1 | 0 | 1 |
| ifab143 | 0 | 0 | 0 | 1 | 1 | 0 | 1 | 1 | 0 | 1 | 1 |
| ifab144 | 0 | 0 | 0 | 1 | 0 | 1 | 1 | 1 | 1 | 0 | 1 |
| ifab145 | 0 | 0 | 0 | 1 | 0 | 1 | 1 | 1 | 0 | 1 | 1 |

The plasmid pCL_P$_{trc}$_tesA was transformed into each of the strains and a fermentation was run in FA2 media with 20 hours from induction to harvest at both 32° C. and 37° C. Data for production of Total Fatty Species from duplicate plate screens is shown in FIGS. 6A and 6B. From this library screen the best construct was determined to be DV2 with iFAB138. The iFAB138 construct was transferred into strain D178 to make strain EG149. This strain was used for further engineering. The sequence of iFAB138 in the genome of EG149 is presented as SEQ ID NO:13. Table 3 presents the genetic characterization of a number of E. coli strains into which plasmids containing the expression constructs described herein were introduced as described below. These strains and plasmids were used to demonstrate the recombinant host cells, cultures, and methods of certain embodiments of the present disclosure. The genetic designations in Table 3 are standard designations known to those of ordinary skill in the art.

TABLE 3

Genetic Characterization of E. coli strains

| Strain | Genetic Characterization |
|---|---|
| DV2 | MG1655 F-, λ-, ilvG-, rfb-50, rph-1, ΔfhuA::FRT, ΔfadE::FRT |
| DV2.1 | DV2 fabB::fabB[A329V] |
| D178 | DV2.1 entD::FRT_P$_{T5}$_entD |
| EG149 | D178 ΔinsH-11::P$_{LACUV5}$-iFAB138 |
| V642 | EG149 rph+ |
| SL313 | V642 lacIZ::P$_{A1}$_'tesA/pDG109 |
| V668 | V642 ilvG+ |
| LC397 | V668 lacIZ::P$_{TRC}$_'tesA(var)_kan |
| SL571 | V668 lacIZ::P$_{TRC}$_'tesA(var)_FRT |
| LC942 | SL571 attTn7::P$_{TRC}$_'tesA(var) |
| DG16 | LC942/pLC56 |
| V940 | LC397/pV171.1 |
| D851 | SL571 yijP::Tn5-cat/pV171.1 |

Plasmids: pDG109, pLC56 and pV171.1 are pCL_P$_{trc}$_carB_tesA_alrA_fabB_fadR operon with variable expression of carB and tesA. iFAB138 is SEQ ID NO: 13.

Example 4

Figure 8:
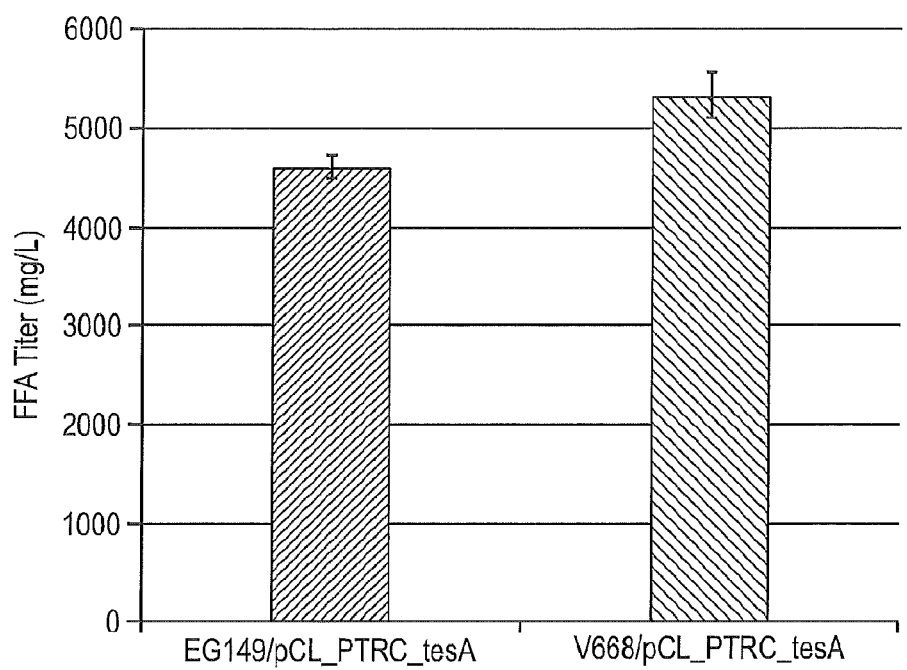
FIG. 8 shows the effect of correcting the rph and ilvG genes. EG149 (rph−ilvg−) and V668 (EG149 rph+ilvG+) were transformed with pCL-tesA (a pCL1920 plasmid containing P$_{TRC}$-'tesA) obtained from D191. The figure shows that correcting the rph and ilvG genes in the EG149 strain allows for a higher level of FFA production than in the V668 strain where the rph and ilvG genes were not corrected.

Increasing the Amount of Free Fatty Acid (FFA) Product by Repairing the Rph and ilvG Mutations The ilvG and rph mutations were corrected in this strain resulting in higher production of FFA. Strains D178, EG149 and V668 (Table 3) were transformed with pCL_P$_{trc}$_tesA. Fermentation was run at 32° C. in FA2 media for 40 hours to compare the FFA production of strains D178, EG149, and V668 with pCL_P$_{trc}$_tesA. Correcting the rph and ilvG mutations resulted in a 116% increase in the FFA production of the base strain with pCL_P$_{trc}$_tesA. As seen in FIG. 8, V668/pCL_P$_{trc}$_tesA produces more FFA than the D178/pCL_P$_{trc}$_tesA, or the EG149/pCL_P$_{trc}$_tesA control. Since FFA is a precursor to the LS9 products, higher FFA production is a good indicator that the new strain can produce higher levels of LS9 products. Fermentation and extraction was run according to a standard FALC fermentation protocol exemplified by the following.

A frozen cell bank vial of the selected E. coli strain was used to inoculate 20 mL of LB broth in a 125 mL baffled shake flask containing spectinomycin antibiotic at a concentration of 115 μg/mL. This shake flask was incubated in an orbital shaker at 32° C. for approximately six hours, then 1.25 mL of the broth was transferred into 125 mL of low P FA2 seed media (2 g/L NH$_4$Cl, 0.5 g/L NaCl, 3 g/L KH$_2$PO$_4$, 0.25 g/L MgSO$_4$-7H2O, 0.015 g/L mM CaCl$_2$-2H2O, 30 g/L glucose, 1 mL/L of a trace minerals solution (2 g/L of ZnCl$_2$.4H$_2$O, 2 g/L of CaCl$_2$.6H$_2$O, 2 g/L of Na$_2$MoO$_4$.2H$_2$O, 1.9 g/L of CuSO$_4$.5H$_2$O, 0.5 g/L of H$_3$BO$_3$, and 10 mL/L of concentrated HCl), 10 mg/L of ferric citrate, 100 mM of Bis-Tris buffer (pH 7.0), and 115 μg/mL of spectinomycin), in a 500 mL baffled Erlenmeyer shake flask, and incubated on a shaker overnight at 32° C. 100 mL of this low P FA2 seed culture was used to inoculate a 5 L Biostat Aplus bioreactor (Sartorius BBI), initially containing 1.9 L of sterilized F1 bioreactor fermentation medium. This medium is initially composed of 3.5 g/L of KH$_2$PO$_4$, 0.5 g/L of (NH$_4$)$_2$SO$_4$, 0.5 g/L of MgSO$_4$ heptahydrate, 10 g/L of sterile filtered glucose, 80 mg/L ferric citrate, 5 g/L Casamino acids, 10 mL/L of the sterile filtered trace minerals solution, 1.25 mL/L of a sterile filtered vitamin solution (0.42 g/L of riboflavin, 5.4 g/L of pantothenic acid, 6 g/L of niacin, 1.4 g/L of pyridoxine, 0.06 g/L of biotin, and 0.04 g/L of folic acid), and the spectinomycin at the same concentration as utilized in the seed media. The pH of the culture was maintained at 6.9 using 28% w/v ammonia water, the temperature at 33° C., the aeration rate at 11 lpm (0.5 v/v/m), and the dissolved oxygen tension at 30% of saturation, utilizing the agitation loop cascaded to the DO controller and oxygen supplementation. Foaming was controlled by the automated addition of a silicone emulsion based antifoam (Dow Corning 1410).

A nutrient feed composed of 3.9 g/L MgSO$_4$ heptahydrate and 600 g/L glucose was started when the glucose in the initial medium was almost depleted (approximately 4-6 hours following inoculation) under an exponential feed rate of 0.3 hr$^{-1}$ to a constant maximal glucose feed rate of 10-12 g/L/hr, based on the nominal fermentation volume of 2 L. Production of fatty alcohol in the bioreactor was induced when the culture attained an OD of 5 AU (approximately 3-4 hours following inoculation) by the addition of a 1M IPTG stock solution to a final concentration of 1 mM. The bioreactor was sampled twice per day thereafter, and harvested approximately 72 hours following inoculation. A 0.5 mL sample of the well-mixed fermentation broth was transferred into a 15 mL conical tube (VWR), and thoroughly mixed with 5 mL of butyl acetate. The tube was inverted several times to mix, then vortexed vigorously for approximately two minutes. The tube was then centrifuged for five minutes to separate the organic and aqueous layers, and a portion of the organic layer transferred into a glass vial for gas chromatographic analysis.

Example 5

Increased Production of Fatty Alcohol by Transposon Mutagenesis—yijP

To improve the titer, yield, productivity of fatty alcohol production by *E. coli*, transposon mutagenesis and high-throughput screening was carried out and beneficial mutations were sequenced. A transposon insertion in the yijP strain was shown to improve the strain's fatty alcohol yield in both shake flask and fed-batch fermentations. The SL313 strain produces fatty alcohols. The genotype of this strain is provided in Table 3. Transposon clones were then subjected to high-throughput screening to measure production of fatty alcohols. Briefly, colonies were picked into deep-well plates containing LB, grown overnight, inoculated into fresh LB and grown for 3 hours, inoculated into fresh FA2.1 media, grown for 16 hours, then extracted using butyl acetate. The crude extract was derivatized with BSTFA (N,O-bis[Trimethylsilyl]trifluoroacetamide) and analyzed using GC/FID. Spectinomycin (100 mg/L) was included in all media to maintain selection of the pDG109 plasmid. Hits were selected by choosing clones that produced a similar total fatty species as the control strain SL313, but that had a higher percent of fatty alcohol species and a lower percent of free fatty acids than the control. Strain 68F11 was identified as a hit and was validated in a shake flask fermentation using FA2.1 media. A comparison of transposon hit 68F11 to control strain SL313 indicated that 68F11 produces a higher percentage of fatty alcohol species than the control, while both strains produce similar titers of total fatty species. A single colony of hit 68F11, named LC535, was sequenced to identify the location of the transposon insertion. Briefly, genomic DNA was purified from a 10 mL overnight LB culture using the kit ZR Fungal/Bacterial DNA MiniPrep™ (Zymo Research Corporation, Irvine, Calif.) according to the manufacturer's instructions. The purified genomic DNA was sequenced outward from the transposon using primers internal to the transposon:

```
DG150
                                        (SEQ ID NO: 14)
5'-GCAGTTATTGGTGCCCTTAAACGCCTGGTTGCTACGCCTG-3'
```

```
DG131
                                        (SEQ ID NO: 15)
5'- GAGCCAATATGCGAGAACACCCGAGAA-3'
```

Strain LC535 was determined to have a transposon insertion in the yijP gene (FIG. 18). yijP encodes a conserved inner membrane protein whose function is unclear. The yijP gene is in an operon and co-transcribed with the ppc gene, encoding phosphoenolpyruvate carboxylase, and the yijO gene, encoding a predicted DNA-binding transcriptional regulator of unknown function. Promoters internal to the transposon likely have effects on the level and timing of transcription of yijP, ppc and yijO, and may also have effects on adjacent genes frwD, pflC, pfld, and argE. Promoters internal to the transposon cassette are shown in FIG. 18, and may have effects on adjacent gene expression. Strain LC535 was evaluated in a fed-batch fermentation on two different dates. Both fermentations demonstrated that LC535 produced fatty alcohols with a higher yield than control SL313, and the improvement was 1.3-1.9% absolute yield based on carbon input. The yijP transposon cassette was further evaluated in a different strain V940, which produces fatty alcohol at a higher yield than strain SL313. The yijP::Tn5-cat cassette was amplified from strain LC535 using primers:

```
LC277
                                        (SEQ ID NO: 16)
5'-CGCTGAACGTATTGCAGGCCGAGTTGCTGCACCGCTCCCGCCAGGCA
G-3'
```

```
LC278
                                        (SEQ ID NO: 17)
5'-GGAATTGCCACGGTGCGGCAGGCTCCATACGCGAGGCCAGGTTATCC
AACG-3'
```

This linear DNA was electroporated into strain SL571 and integrated into the chromosome using the lambda red recombination system. Colonies were screened using primers outside the transposon region:

```
                                        (SEQ ID NO: 18)
DG407 5'-AATCACCAGCACTAAAGTGCGCGGTTCGTTACCCG-3'

(SEQ ID NO: 19)
DG408 5'-ATCTGCCGTGGATTGCAGAGTCTATTCAGCTACG-3'
```

Figure 9:
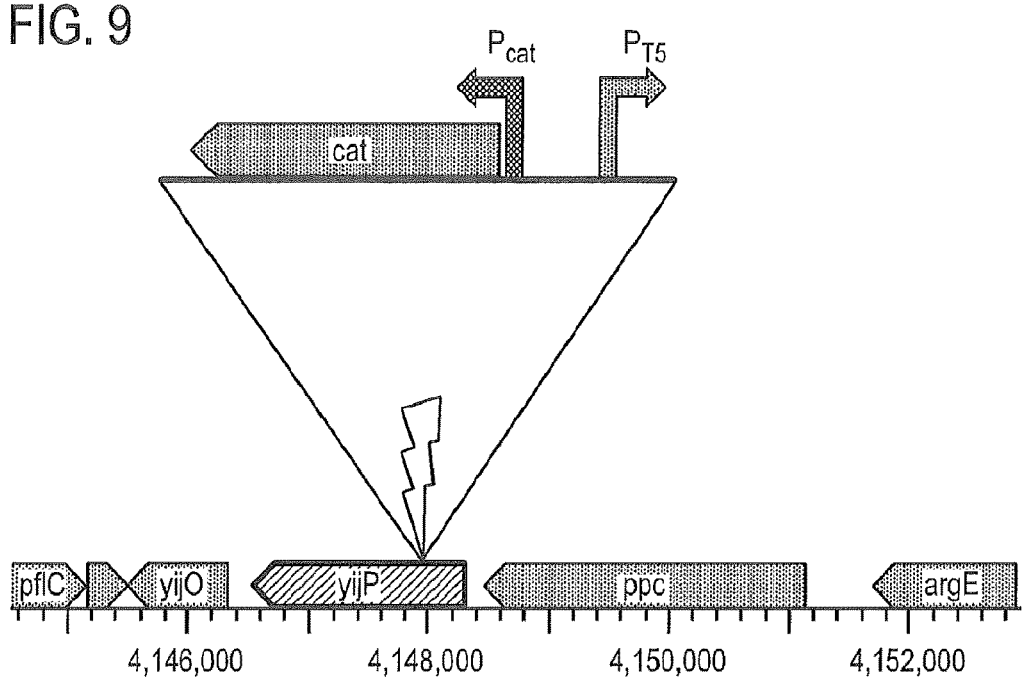
FIG. 9 is a diagrammatic depiction of a transposon cassette insertion in the yijP gene of strain LC535 (transposon hit 68F11). Promoters internal to the transposon cassette are shown, and may have effects on adjacent gene expression.

A colony with the correct yijP transposon cassette (FIG. 9) was transformed with the production plasmid pV171.1 to produce strain D851. D851 (V940 yijP::Tn5-cat) was tested in a shake-flask fermentation against isogenic strain V940 that does not contain the yijP transposon cassette. The result of this fermentation showed that the yijP transposon cassette confers production of a higher percent of fatty alcohol by the D851 strain relative to the V940 strain and produces similar titers of total fatty species as the V940 control strain. Strain D851 was evaluated in a fed-batch fermentation on two different dates. Data from these fermentations is shown in Table 4 which illustrates that in 5-liter fed-batch fermentations, strains with the yijP::Tn5-cat transposon insertion had an increased total fatty species ("FAS") yield and an increase in percent fatty alcohol ("FALC"). "Fatty Species" include FALC and FFA.

TABLE 4

Effect of yijp transposon insertion on titer and yield of FAS and FALC

| Strain | FAS Titer | FAS Yield | Percent FALC | FALC Yield |
|---|---|---|---|---|
| V940 | 68 g/L | 18.70% | 95.00% | 17.80% |
| D851 | 70 g/L | 19.40% | 96.10% | 18.60% |
| V940 | 64 g/L | 18.40% | 91.90% | 16.90% |
| D851 | 67 g/L | 19.00% | 94.00% | 17.80% |

Tank Fermentation Method:

To assess production of fatty acid esters in tank a glycerol vial of desired strain was used to inoculate 20 mL LB+spectinomycin in shake flask and incubated at 32° C. for approximately six hours. 4 mL of LB culture was used to inoculate 125 mL Low PFA Seed Media (below), which was then incubated at 32° C. shaker overnight. 50 mL of the overnight culture was used to inoculate 1 L of Tank Media. Tanks were run at pH 7.2 and 30.5° C. under pH stat conditions with a maximum feed rate of 16 g/L/hr (glucose or methanol).

TABLE 5

Low P FA Seed Media

| Component | Concentration |
|---|---|
| NH4Cl | 2 g/L |
| NaCl | 0.5 g/L |
| KH2PO4 | 1 g/L |
| MgSO4—7H2O | 0.25 g/L |
| CaCl2—2H2O | 0.015 g/L |
| Glucose | 20 g/L |
| TM2 Trace Minerals solution | 1 mL/L |
| Ferric citrate | 10 mg/L |
| Bis Tris buffer (pH 7.0) | 100 mM |
| Spectinomycin | 115 mg/L |

TABLE 6

Tank Media

| Component | Concentration |
|---|---|
| (NH4)2SO4 | 0.5 g/L |
| KH2PO4 | 3.0 g/L |
| Ferric Citrate | 0.034 g/L |
| TM2 Trace Minerals Solution | 10 mL/L |
| Casamino acids | 5 g/L |
| Post sterile additions | |
| MgSO4—7H2O | 2.2 g/L |
| Trace Vitamins Solution | 1.25 mL/L |
| Glucose | 5 g/L |
| Inoculum | 50 mL/L |

Example 6

Addition of an N-Terminal 60 bp Fusion Tag to CarB (CarB60)

There are many ways to increase the solubility, stability, expression or functionality of a protein. In one approach to increasing the solubility of CarB, a fusion tag could be cloned before the gene. In another approach increase the expression of CarB, the promoter or ribosome binding site (RBS) of the gene could be altered. In this study, carB (SEQ ID NO: 7) was modified by addition of an N-terminal 60 bp fusion tag. To generate the modified protein (referred to herein as "CarB60"), carB was first cloned into the pET15b vector using primers:

(SEQ ID NO: 20)
5'-GCAATTCCATATGACGAGCGATGTTCACGA-3';
and (SEQ ID NO: 21)
5'-CCGCTCGAGTAAATCAGACCGAACTCGCG.

The pET15b-carB construct contained 60 nucleotides directly upstream of the carB gene:

(SEQ ID NO: 22)
5'-ATGGGCAGCAGCCATCATCATCATCATCACAGCAGCGGCCTGGTGCC
GCGCGGCAGCCAT

Figure 10:
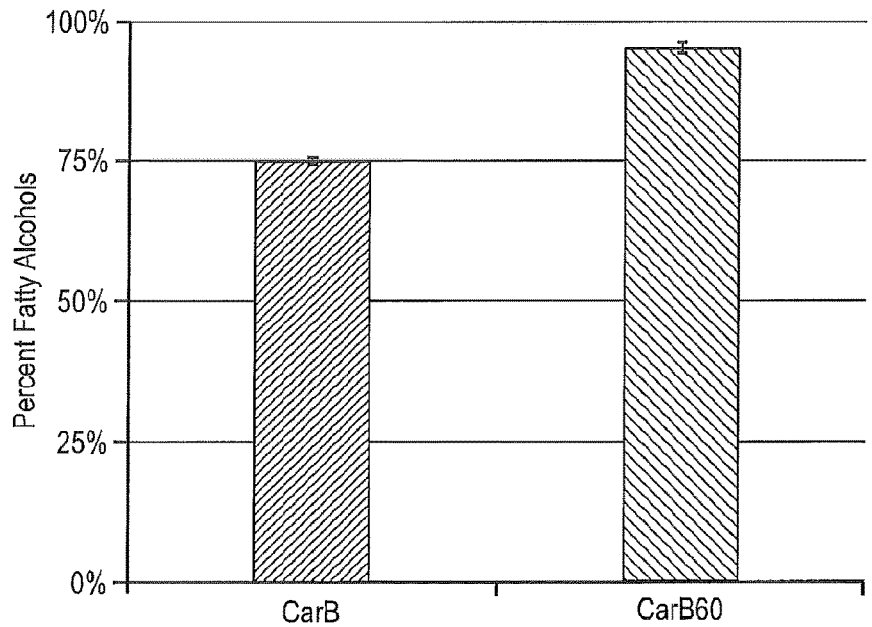
FIG. 10 shows conversion of free fatty acids to fatty alcohols by CarB60 in strain V324. The figures shows that cells expressing CarB60 from the chromosome (dark bars) convert a greater fraction of C12 and C14 free fatty acids into fatty alcohol compared to CarB (light bars).

The fusion tag version of carB was renamed carB60. The pET15b_carB60 was then digested using restriction enzymes NcoI and HindIII and subcloned into the pCL1920-derived vector OP80 which was cut with the same enzymes. This plasmid was transformed into strain V324 (MG1655 ΔfadE::FRT ΔfhuA::FRT fabB::A329V entD::T5-entD lacIZ::$P_{TRC}$-'TesA) to evaluate FALC production. Strains were fermented according to a standard procedure (summarized below) and the total fatty species titer and total fatty alcohol titer were quantified. FIG. 10 shows that CarB60 increases fatty alcohol titers and therefore the CarB60 enzyme has higher total cellular activity than CarB when expressed from a multicopy plasmid.

To assess production of fatty alcohols in production strains, transformants were grown in 2 ml of LB broth supplemented with antibiotics (100 mg/L) at 37° C. After overnight growth, 40 ul of culture was transferred into 2 ml of fresh LB supplemented with antibiotics. After 3 hours of growth, 2 ml of culture were transferred into a 125 mL flask containing 20 ml of M9 medium with 3% glucose supplemented with 20 μl trace mineral solution, 10 μg/L iron citrate, 1 μg/L thiamine, and antibiotics (FA2 media). When the $OD_{600}$ of the culture reached 1.0, 1 mM of IPTG was added to each flask. After 20 hours of growth at 37° C., 400 μL samples from each flask were removed and fatty alcohols extracted with 400 μL butyl acetate. To further understand the mechanism of the improved CarB activity, CarB60 was purified from strain D178 which does not contain 'TesA (MG1655 ΔfadE::FRT ΔfhuA::FRT fabB::A329V entD::$P_{T5}$-entD). Briefly, pCL1920_carB60 was transformed into strain D178, which has been engineered for fatty alcohol production, and fermentation was carried out at 37° C. in FA-2 medium supplemented with spectinomycin (100 μg/ml). When the culture $OD_{600}$ reached 1.6, cells were induced with 1 mM isopropyl-ß-D-thiogalactopyranoside (IPTG) and incubated for an additional 23 h at 37° C. For purification of CarB60, the cells were harvested by centrifugation for 20 min at 4° C. at 4,500 rpm. Cell paste (10 g) was suspended in 12 ml of BugBuster MasterMix (Novagen) and protease inhibitor cocktail solution. The cells were disrupted by French Press and the resulting homogenate was centrifuged at 10,000 rpm to remove cellular debris. Ni-NTA was added to the resulting mixture, and the suspension was swirled at 4° C. at 100 rpm for 1 hour on a rotary shaker. The slurry was poured into a column, and the flow-through was collected. The Ni-NTA resin was washed with 10 mM imidazole in 50 mM sodium phosphate buffer pH 8.0 containing 300 mM NaCl, and further washed with 20 mM imidazole in 50 mM sodium phosphate buffer pH 8.0 containing 300 mM NaCl. The CarB60 protein was eluted with 250 mM imidazole in 50 mM sodium phosphate buffer pH 8.0 containing 300 mM NaCl, and analyzed by SDS-PAGE. The protein was dialyzed against 20% (v/v) glycerol in 50 sodium phosphate buffer pH 7.5 yielding approximately 10 mg of CarB60 per liter of culture. The protein was flash frozen and stored at −80° C. until needed.

The CarB60 protein was abundantly expressed from a multicopy plasmid. Additional SDS-PAGE analysis showed that expression of CarB60 was higher than CarB. The higher expression level of CarB60 suggested that the carB60 gene integrated into the E. coli chromosome would produce more protein than the carB gene in the same location. To test this hypothesis, the carB60 gene was integrated into the E. coli chromosome. Briefly, the carB60 gene was first amplified from pCL_carB60 using forward primer:

```
                                     (SEQ ID NO: 23)
5'-ACGGATCCCCGGAATGCGCAACGCAATTAATGTaAGTTAGCGC-3';
and reverse primer:
                                     (SEQ ID NO: 24)
5'-TGCGTCATCGCCATTGAATTCCTAAATCAGACCGAACTCGCGCAGG-
3'.
```

A second PCR product was amplified from vector pAH56 using forward primer:

```
                                     (SEQ ID NO: 25)
        5'-ATTCCGGGGATCCGTCGACC-3';
        and reverse primer:
                                     (SEQ ID NO: 26)
        5'-AATGGCGATGACGCATCCTCACG-3'
```

This fragment contains a kanamycin resistance cassette, γattP site, and γR6k origin of replication. The two PCR products were joined using the InFusion kit (Clontech) to create plasmid pSL116-126. A fatty alcohol production strain containing an integrated form of 'TesA12H08 and a helper plasmid pINT was transformed with either pSL116-126 containing the carB60 gene or plasmid F27 containing the carB gene. These strains were fermented in FA2 media according to standard procedures for shake-flask fermentations, as described above. To characterize and quantify the fatty alcohols and fatty acid esters, gas chromatography ("GC") coupled with flame ionization ("FID") detection was used. The crude extract was derivatized with BSTFA (N,O-bis[Trimethylsilyl]trifluoroacetamide) and analyzed using a GC/FID. Quantification was carried out by injecting various concentrations of the appropriate authentic references using the GC method described above as well as assays including, but not limited to, gas chromatography (GC), mass spectroscopy (MS), thin layer chromatography (TLC), high-performance liquid chromatography (HPLC), liquid chromatography (LC), GC coupled with a flame ionization detector (GC-FID), GC-MS, and LC-MS, can be used. When testing for the expression of a polypeptide, techniques such as Western blotting and dot blotting may be used.

Figure 11:
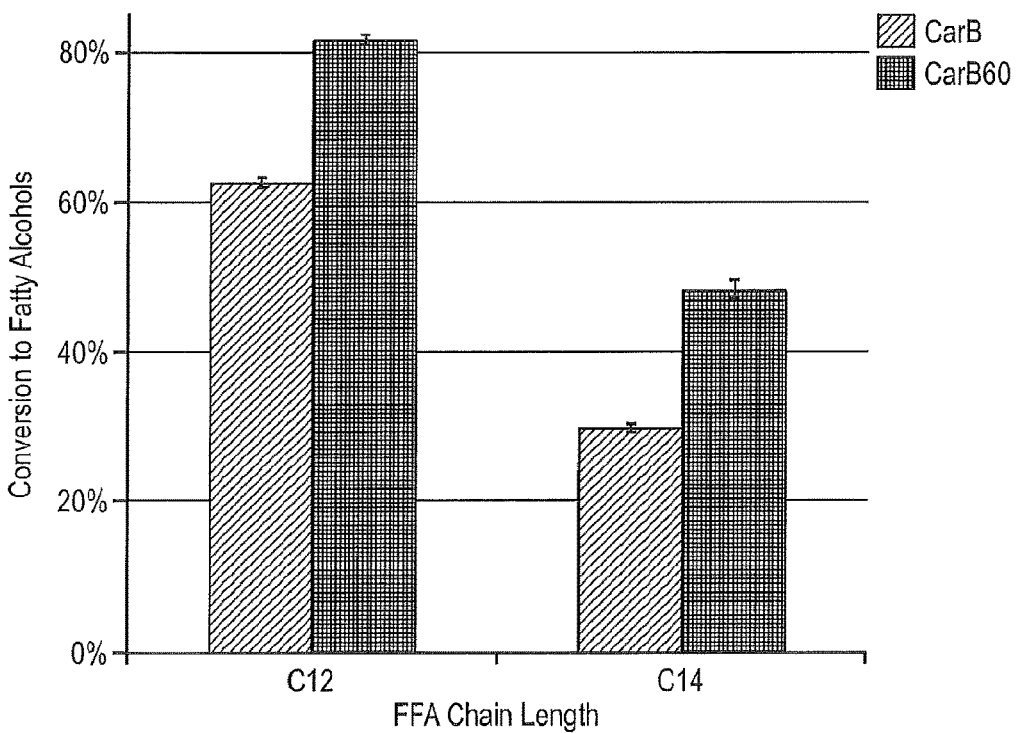
FIG. 11 shows that cells expressing CarB60 from the chromosome convert a greater fraction of C12 and C14 free fatty acids into fatty alcohol compared to CarB.

The results of the fermentation after 20 hours are shown in FIG. 11. The total fatty product titers of the two strains are similar (2.4 g/L total fatty species), however integrated CarB60 converts a greater fraction of C12 and C14 chain length free fatty acids into fatty alcohols, compared to CarB without the N-terminal tag. These data suggest that cells expressing CarB60 have a higher total cellular carboxylic acid reductase activity, and can convert more FFA into fatty alcohols. Thus, carB60 when integrated in the chromosome is an improved carB template that provides desired activity for evolving carB gene to identify improved carB variants.

Example 7

Generation of CarB Mutants

The CarB enzyme is a rate-limiting step in the production of fatty alcohols under certain process conditions. To produce fatty alcohols economically, efforts were made to increase the activity of the CarB enzyme.

Error Prone PCR Library Screen:

Random mutagenesis using error prone PCR was performed under conditions where the copying fidelity of the DNA polymerase is low. The mutagenized nucleic acids were cloned into a vector, and error-prone PCR followed by high-throughput screening was done to find beneficial mutations that increase conversion of free fatty acids to fatty alcohols (as detailed below). Important residues were further mutated to other amino acids. A number of single amino acid mutations and combinations of mutations increased the fraction of fatty species that are converted to fatty alcohols. Briefly, random mutations were generated in the carB60opt gene by error-prone PCR using the Genemorph II kit (Stratagene). Mutations were generated in only one of two domains of carB60opt separately, to facilitate cloning. Library 1 contained the first 759 residues of carB60opt and was generated by error-prone PCR using primers:

```
HZ117
                                     (SEQ ID NO: 27)
5'-ACGGAAAGGAGCTAGCACATGGGCAGCAGCCATCATCAT-3';
and DG264
                                     (SEQ ID NO: 28)
5'-GTAAAGGATGGACGGCGGTCACCCGCC-3'.
```

The vector for Library 1 was plasmid pDG115 digested with enzymes NheI and PshAI. Library 2 contained the last 435 residues of carB60opt and was generated by error-prone PCR using primers:

```
DG263
                                     (SEQ ID NO: 29)
5'-CACGGCGGGTGACCGCCGTCCATCC-3';
and HZ118
                                     (SEQ ID NO: 30)
5'-TTAATTCCGGGGATCCCTAAATCAGACCGAACTCGCGCAGGTC-3'.
```

The vector for Library 2 was plasmid pDG115 digested with enzymes PshAI and BamHI. The error-prone inserts were cloned into the vectors using InFusion Advantage (Clontech) and passaged through cloning strain NEB Turbo (New England Biolabs). The libraries were then transformed into strain EG442 (EG149 Tn7::$P_{TRC}$-ABR lacIZ::$P_{T5O}$-ABR). Error-prone carB60opt clones were then subjected to high-throughput screening to measure production of fatty alcohols. Briefly, colonies were picked into deep-well plates containing LB, grown overnight, inoculated into fresh LB and grown for 3 hours, inoculated into fresh FA-2.1 media, grown for 16 hours, then extracted using butyl acetate. The crude extract was derivatized with BSTFA (N,O-bis[Trimethylsilyl]trifluoroacetamide) and analyzed using a standard GC/FID method. Spectinomycin (100 mg/L) was included in all media to maintain selection of the pDG115 plasmid. Hits were selected by choosing clones that produced a smaller total free fatty acid titer and a larger total fatty alcohol titer compared to the control strain. To compare hits from different fermentation screens, the conversion of free fatty acids to fatty alcohols was normalized by calculating a normalized free fatty acid percentage NORM FFA=Mutant Percent FFA/Control Percent FFA where "Percent FFA" is the total free fatty acid species titer divided by the total fatty species titer. Hits were subjected to further verification using shake-flask fermentations, as described below.

Hits were sequenced to identify the beneficial mutations. Sequencing was performed by colony PCR of the entire carB60opt gene using primers SL59
(SEQ ID NO: 31)
5'-CAGCCGTTTATTGCCGACTGGATG-3';
and

EG479
(SEQ ID NO: 32)
5'-CTGTTTTATCAGACCGCTTCTGCGTTC-3', and sequenced using primers internal to the carB60opt enzyme.

The beneficial mutations that improved the CarB60opt enzyme are shown in Table 7. The normalized free fatty acid (NORM FFA) column indicates the improvement in the enzyme, with lower values indicating the best improvement. "Well #" indicates the primary screening well that this mutation was found in. All residue numbers refer to the CarB protein sequence, which does not include the 60 bp tag. Mutations indicated with the prefix "Tag:" indication mutations in the 60 bp/20 residue N-terminal tag.

TABLE 7

Beneficial Mutations in the CarB Enzyme Identified During Error-Prone Screening (TAG Mutations Removed)

| Well # | Norm FFA | Missense Mutations | Silent Mutations |
|---|---|---|---|
| 131B08 | 70.50% | L799M V810F S927R M1062L A1158V F1170I | CCG1116CCT |
| 20C07 | 71.80% | A535S | |
| 65B02 | 74.70% | M930R | ACC867ACA |
| 54B10 | 76.30% | L80Q T231M F288L A418T V530M A541V G677D P712A | |
| 67E01 | 78.20% | D750G R827C D986G G1026D P1149S | GCA1031GCT GTC1076GTT |
| 65C03 | 78.90% | V926A | ATT941ATA |
| 12C10 | 80.30% | V46I | |
| 66E08 | 80.10% | V926A | |
| 70F02 | 80.90% | D750G R827C D986G G1026D P1149S | GCA101GCT GTC1073GTT |
| 07D01 | 82.40% | E20K V191A | |
| 66G09 | 82.40% | R827C L1128S | ACG780ACA CTG923TTG |
| 25H02 | 83.50% | F288S | |
| 06C01 | 85.10% | V46I | 06C01 |
| 05D02 | 85.20% | T396S | CCG477CCT |
| 124E03 | 86.00% | R827C L1128S | ACG780ACA CTG923TTG |
| 17A04 | 86.20% | A574T | GCA237GCT ACC676ACT GCC529GCT |
| 132C08 | 87.00% | M1062T R1080H | TTG830TTA TAC834TAT |
| 72C09 | 87.30% | P809L M1062V | |
| 10F02 | 87.70% | E636K | |
| 71H03 | 88.10% | R827C L1128S | ACG780ACA CTG923TTG |
| 38G04 | 88.90% | D143E A612T | GCA181GCG |
| 42F08 | 90.20% | T90M | CTG186CTT |
| 66C04 | 90.30% | L1128S | |
| 18CC03 | 90.40% | Q473L | |
| 12E02 | 90.60% | D19N S22N R87H L416S | CCG167CCA |

TABLE 7-continued

Beneficial Mutations in the CarB Enzyme Identified During Error-Prone Screening (TAG Mutations Removed)

| Well # | Norm FFA | Missense Mutations | Silent Mutations |
|---|---|---|---|
| 28B09 | 91.10% | E28K H212N Q473L | CCG122CCA ACG178ACA CTG83TTG CTG340CTA ACC401ACT GCA681GCG |
| 103E09 | 92.20% | E936K P113R | CGT829CGG CTG1007CTA |
| 03E09 | 93.20% | M259I | |
| 74G11 | 93.80% | I870V S927I S985I I1164F | GTG1000GTC |
| 46C01 | 95.60% | D18V D292N | |

Saturation Mutagenesis (Combo 1 and 2 Library Generated):

Amino acid positions deemed beneficial for fatty alcohol production following error-prone PCR were subjected to further mutagenesis. Primers containing the degenerate nucleotides NNK or NNS were used to mutate these positions to other amino acids. The resulting "saturation mutagenesis libraries" were screened as described above for the error prone libraries, and hits were identified that further improved fatty alcohol conversion (a smaller total free fatty acid titer and a larger total fatty alcohol titer compared to the parent "control" strain). Single amino acid/codon changes in nine different positions that improve the production of fatty alcohols are shown in Table 8. Hits were subjected to further verification using shake-flask fermentations, as described herein.

TABLE 8

Beneficial Mutations in the CarB Enzyme Identified During Amino Acid Saturation Mutagenesis

| WT Amino Acid | WT Codon | Mutant Amino Acid | Mutant Codon | Norm FFA |
|---|---|---|---|---|
| E20 | GAG | F | TTC | 92.20% |
| | | L | CTG | 94.50% |
| | | L | TTG | 96.20% |
| | | R | CGC | 86.50% |
| | | S | TCG | 87.40% |
| | | V | GTG | 86.00% |
| | | V | GTC | 85.30% |
| | | Y | TAC | 88.80% |
| V191 | GTC | A | GCC | 88.70% |
| | | S | AGT | 98.00% |
| F288 | TTT | G | GGG | 70.30% |
| | | R | AGG | 77.20% |
| | | S | TCT | 85.60% |
| | | S | AGC | 79.60% |
| Q473 | CAA | A | GCG | 89.50% |
| | | F | TTC | 89.10% |
| | | H | CAC | 84.10% |
| | | I | ATC | 77.20% |
| | | K | AAG | 90.30% |
| | | L | CTA | 90.10% |
| | | M | ATG | 89.00% |
| | | R | AGG | 88.00% |
| | | V | GTG | 89.20% |
| | | W | TGG | 84.50% |
| | | Y | TAC | 86.00% |
| A535 | GCC | A | TCC | 71.80% |
| R827 | CGC | A | GCC | 93.20% |
| | | C | TGT | 87.90% |
| | | C | TGC | 83.20% |
| V926 | GTT | A | GCT | 78.10% |
| | | A | GCG | 66.30% |
| | | A | GCC | 69.50% |
| | | E | GAG | 65.80% |
| | | G | GGC | 78.60% |
| S927 | AGC | G | GGG | 77.60% |
| | | G | GGT | 79.30% |
| | | I | ATC | 90.80% |
| | | K | AAG | 70.70% |
| | | V | GTG | 87.90% |
| M930 | ATG | K | AAG | 82.30% |
| | | R | CGG | 73.80% |
| | | R | AGG | 69.80% |
| L1128 | TTG | A | GCG | 92.70% |
| | | G | GGG | 89.70% |
| | | K | AAG | 94.80% |
| | | M | ATG | 95.80% |
| | | P | CCG | 98.40% |
| | | R | AGG | 90.90% |
| | | R | CGG | 88.50% |
| | | S | TCG | 88.90% |
| | | T | ACG | 96.30% |
| | | V | GTG | 93.90% |
| | | W | TGG | 78.80% |
| | | Y | TAC | 87.90% |

Amino acid substitutions deemed beneficial to fatty alcohol production were next combined. PCR was used to amplify parts of the carBopt gene containing various desired mutations, and the parts were joined together using a PCR-based method (Horton, R. M., Hunt, H. D., Ho, S. N., Pullen, J. K. and Pease, L. R. 1989). The carBopt gene was screened without the 60 bp N-terminal tag. The mutations combined in this combination library are shown in Table 9.

TABLE 9

CarB Mutations from the First Combination Library

| Mutation | Codon |
|---|---|
| E20V | GTG |
| E20S | TCG |
| E20R | CGC |
| V191S | AGT |
| F288R | AGG |
| F288S | AGC |

TABLE 9-continued

CarB Mutations from the First Combination Library

| Mutation | Codon |
|---|---|
| F288G | GGG |
| Q473L | CTG |
| Q473W | TGG |
| Q473Y | TAC |
| Q473I | ATC |
| Q473H | CAC |
| A535S | TCC |

Figure 12:
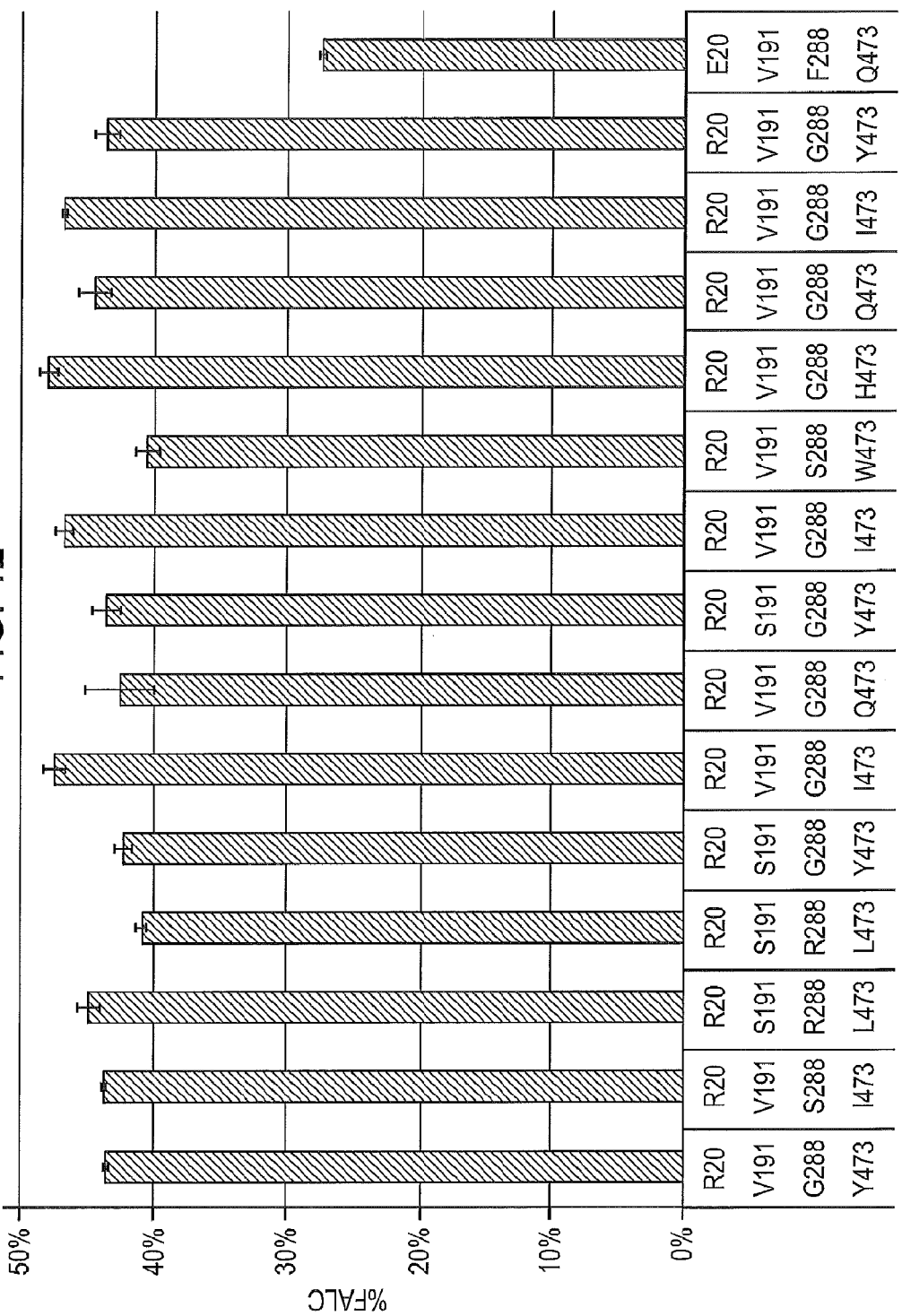
FIG. 12 shows fatty alcohol production following fermentation of combination library mutants.
Figure 16:
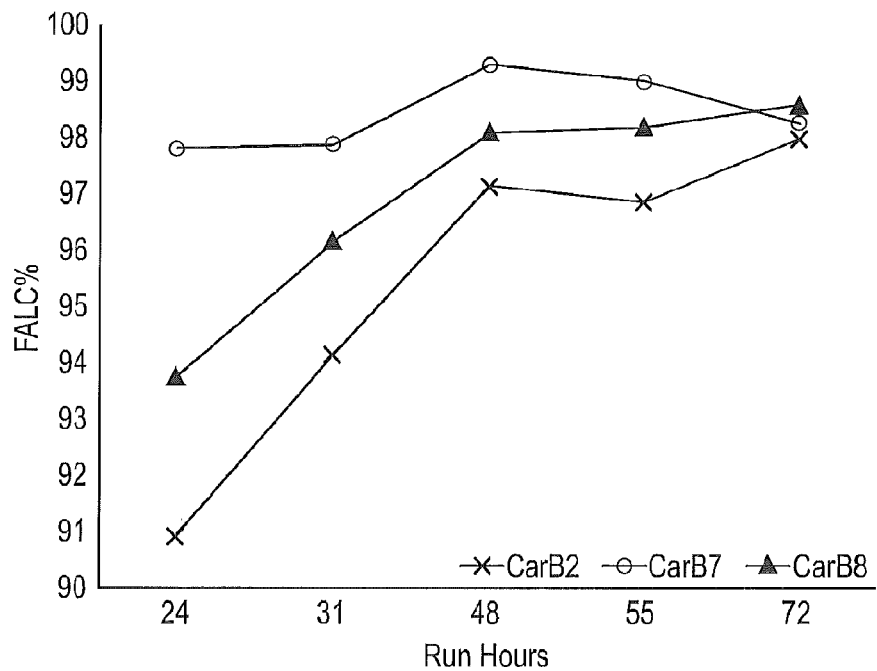
FIG. 16 shows novel CarB variants for improved production of fatty alcohols in bioreactors.

To facilitate screening, the resulting CarB combination library was then integrated into the chromosome of strain V668 at the lacZ locus. The sequence of the carBopt gene at this locus is presented as SEQ ID NO:7. The genotype of strain V668 is MG1655 (ΔfadE::FRT ΔfhuA::FRT ΔfabB::A329V ΔentD::T5-entD ΔinsH-11::$P_{lacUV5}$fab138 rph+ ilvG+) (as shown in Table 3 and FIG. 16). The strains were then transformed with plasmid pVA3, which contains TesA, a catalytically inactive CarB enzyme CarB[S693A] which destroys the phosphopantetheine attachment site, and other genes which increase the production of free fatty acids. The combination library was screened as described above for the error prone library. V668 with integrated carB opt (A535S) in the lacZ region and containing pVA3 was used as the control. Hits were selected that increased the production of fatty alcohols and were subjected to further verification using shake-flask fermentations, as described in Example 5. The improved percentage of fatty alcohol production following shake flask fermentation of recombinant host cells expressing CarB combination mutants is shown in FIG. 12.

The integrated CarB combination mutants were amplified from the integrated carB hits by PCR using the primers:

```
EG58
                             (SEQ ID NO: 33)
5'-GCACTCGACCGGAATTATCG;
and EG626
                             (SEQ ID NO: 34)
5'-GCACTACGCGTACTGTGAGCCAGAG.
```

These inserts were re-amplified using primers:

```
DG243
                                               (SEQ ID NO: 35)
5'-GAGGAATAAACCATGACGAGCGATGTTCACGACGCGACCGACGGC;
and DG210
                             (SEQ ID NO: 36)
5'-CTAAATCAGACCGAACTCGCGCAGG.
```

Using InFusion cloning, the pooled carB mutants were cloned into a production plasmid, pV869, which was PCR amplified using primers:

```
DG228
                             (SEQ ID NO: 37)
5'-CATGGTTTATTCCTCCTTATTTAATCGATAC;
and DG318
                             (SEQ ID NO: 38)
5'-TGACCTGCGCGAGTTCGGTCTGATTTAG.
```

Figure 13:
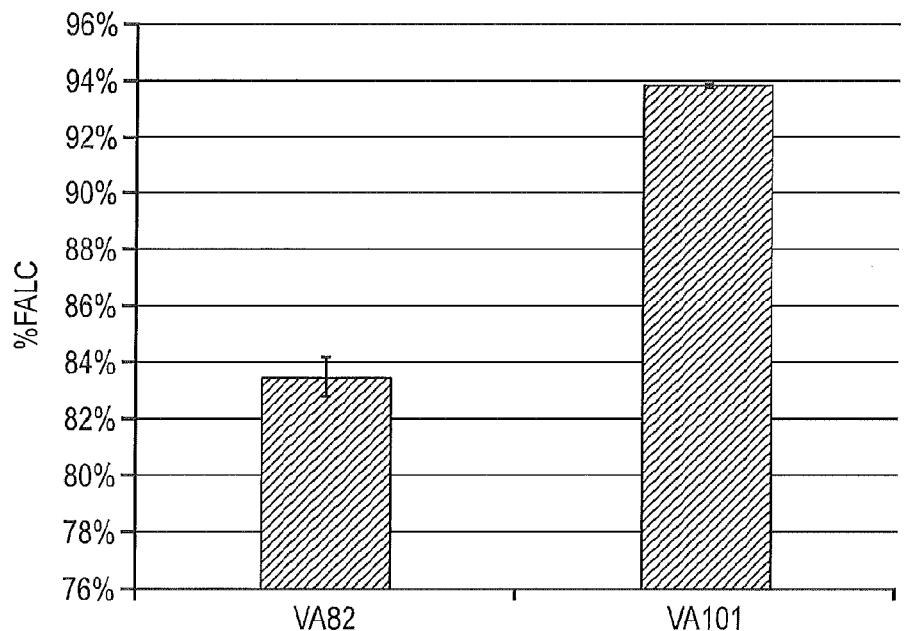
FIG. 13 shows fatty alcohol production by carB variants in production plasmid (carB1 and CarB2) following shake-flask fermentation.

The carB mutant that performed the best in the shake-flask fermentation plasmid screen (carB2; Table 11) was designated VA101 and the control strain carrying carBopt [A535S] was designated VA82. See FIG. 13.

Amino acid substitutions in the reduction domain of carB deemed beneficial to fatty alcohol production were combined with one of the best carB-L combination library hits, "carB3" (Table 11). PCR was used to amplify parts of the carBopt gene containing various desired mutations in Reduction domain, and the parts were joined together using SOE PCR. The mutations combined in this combination library are shown in Table 10.

TABLE 10

CarB Mutations from the Second Combination Library

| Mutation | Codon |
|---|---|
| R827C | TGC |
| R827A | GCA |
| V926A | GCG |
| V926E | GAG |
| S927K | AAG |
| S927G | GGG |
| M930K | AAG |
| M930R | AGG |
| L1128W | TGG |

Figure 14:
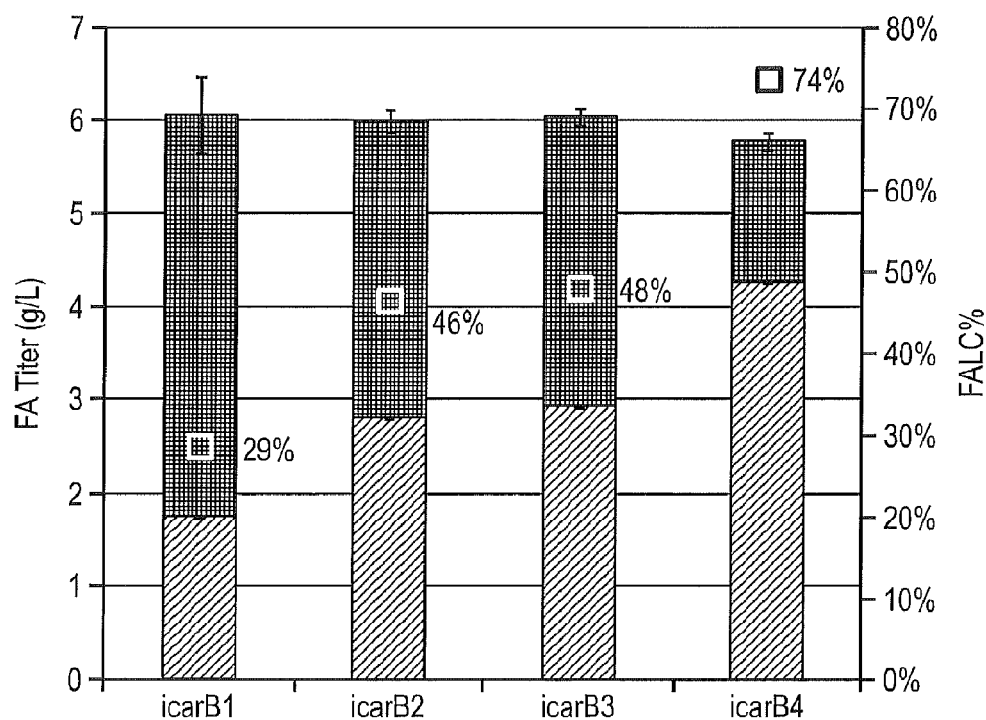
FIG. 14 shows fatty alcohol production by single-copy integrated carB variants (icarB1 icarB2, icarB3, and icarB4) following shake-flask fermentation.

The combination library was screened as described above for the error prone library. V668 with integrated carB3 in the lacZ region and containing pVA3 was used as a control. Hits were selected that exhibited increased production of fatty alcohols and were subjected to further verification using shake-flask fermentations, as described above. The results of a shake flask fermentation showing an improved percentage of fatty alcohol production using a further CarB combination mutation (carB4) is shown in Table 11. A graphic depiction of the relative conversion efficiency of low copy CarB variants is presented in FIG. 14. Results reported in Table 11 are from bioreactor runs carried out under identical conditions.

TABLE 11

CAR Variants

| Name | Mutation(s) | Strain | Tank data | Notes |
|---|---|---|---|---|
| carB | None = WT (E20 V191 F288 Q473) | | | protein is SEQ ID NO: 7 |
| carB60 | None + tag | V324 | | |
| carB1 | A535S | V940 | 83% FALC; C12/C14 = 3.4 | has one copy of 12H08 chromosomal TE |
| carB2 | E20R, F288G, Q473I, A535S | LH375 | 97% FALC; C12/C14 = 3.6 | has two copies of 12H08 chromosomal TE |
| carB2 | E20R, F288G, Q473I, A535S | LH346 | 96% FALC; C12/C14 = 3.7 | has one copy of 12H08 chromosomal TE |
| carB3 | E20R, F288G, Q473S, A535S | L combo library | No examples run in bioreactors to date | |
| carB4 | E20R, F288G, Q473H, A535S, R827A, S927G | R combo library (VA-219) | 97% FALC; C12/C14 = 3.9 | has two copies of 12H08 chromosomal TE |
| carA | None | See, US Patent Pub. No. 20100105963 | | protein is SEQ ID NO: 39 |
| FadD9 | None | See, US Patent Pub. No. 20100105963 | | protein is SEQ ID NO: 40 |

The DNA sequences of CarA, FadD9, CarB, and CarB60 are presented herein as SEQ ID NO: 41, 42, 43 and 44, respectively.

Identification of additional beneficial mutations in CarB enzyme by saturation mutagenesis:

A dual-plasmid screening system was later developed and validated to identify improved CarB variants over CarB4 for FALC production. The dual-plasmid system met the following criteria: 1) Mutant clones produce high FA titer to provide fatty acid flux in excess of CarB activity. This is accomplished by transforming a base strain (V668 with two copies of chromosomal TE) with a plasmid (pLYC4, pCL1920_P$_{TRC}$_carDead_tesA_alrAadp1_fabB[A329G]_fadR) that carries the FALC operon with a catalytically inactive CarB enzyme CarB[S693A] to enhance the production of free fatty acids; 2) The screening plasmid with carB mutant template, preferably smaller than 9-kb, is amenable to saturation mutagenesis procedures and is compatible for expression with pLYC4; 3) The dynamic range of CarB activity is tunable. This is achieved by combining a weaker promoter (P$_{TRC1}$) and alternative start codons (GTG or TTG) to tune CarB4 expression levels. 3) Good plasmid stability, a toxin/antitoxin module (ccdBA operon) was introduced to maintain plasmid stability.

Briefly, the screening plasmid pBZ1 (pACYCDuet-1_P$_{TRC1}$-carB4GTG_rrnBter_ccdAB) was constructed from four parts using In-Fusion HD cloning method (Clontech) by mixing equal molar ratios of four parts (P$_{TRC1}$, carB4 with ATG/TTG/GTG start codons, rrnB T1T2 terminators with ccdAB, and pACYCDuet-1 vector). The parts (1 to 4) were PCR amplified by the following primer pairs:

(1) P$_{TRC1}$-Forward primer
(SEQ ID NO: 45)
5'CGGTTCTGGCAAATATTCTGAAATGAGCTGTTGACAATTAATCAAATCCGGCTCGTATAATGTGTG-3'
and reverse primer
(SEQ ID NO: 46)
5'-GGTTTATTCCTCCTTATTTAATCGATACAT-3' using pVA232 (pCL1920_P$_{TRC}$_carB4_tesA_alrAadp1_fabB[A329G]_fadR) plasmid as template.

(1) carB4 with ATG/TTG/GTG start codons-Forward primer carB4 ATG
(SEQ ID NO: 47)
5'ATGTATCGATTAAATAAGGAGGAATAAACCATGGGCACGAGCGATGTTCACGACGCGAC-3';

carB4 GTG
(SEQ ID NO: 48)
5'ATGTATCGATTAAATAAGGAGGAATAAACCGTGGGCACGAGCGATGTTCACGACGCGAC-3';
and carB4 TTG
(SEQ ID NO: 49)
5'-ATGTATCGATTAAATAAGGAGGAATAAACCTTGGGCACGAGCGATGTTCACGACGCGAC-3';
and reverse primer carB4 rev
(SEQ ID NO: 50)
5'-TTCTAAATCAGACCGAACTCGCGCAG-3',
using pVA232 plasmid as template.

(3) The rrnB T1T2 terminators with ccdAB-Forward primer rrnB T1T2 term
(SEQ ID NO: 51)
5'-CTGCGCGAGTTCGGTCTGATTTAGAATTCCTCGAGGATGGTAGTGTGG-3'
and reverse primer ccdAB rev
(SEQ ID NO: 52)
5'-CAGTCGACATACGAAACGGGAATGCGG-3', using plasmid pAH008 (pV171_ccdBA operon).

(4) The pACYCDuet-1 vector backbone-Forward primer pACYC vector for
(SEQ ID NO: 53)
5' CCGCATTCCCGTTTCGTATGTCGACTGAAACCTCAGGCATTGAGAAGCACACGGTC-3'
and reverse primer pACYC vector rev
(SEQ ID NO: 54)
5'-CTCATTTCAGAATATTTGCCAGAACCGTTAATTTCCTAATGCAGGAGTCGCATAAG-3'.

Figure 15:
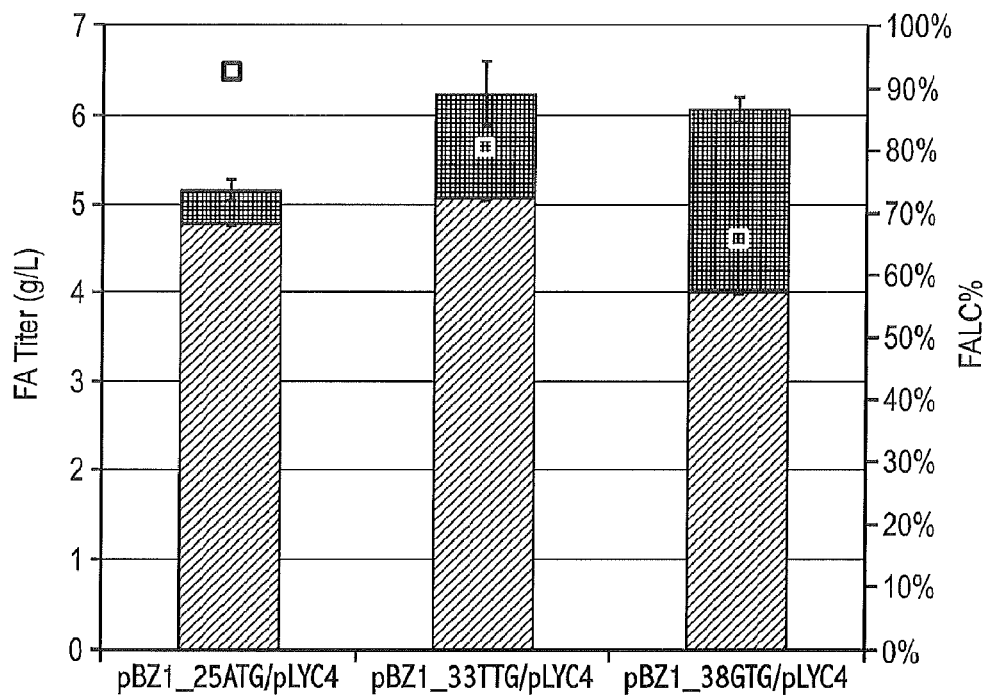
FIG. 15 shows results of dual-plasmid screening system for improved CarB variants as validiated by shake-flask fermentation.

The pBZ1 plasmid was co-expressed with pLYC4 in the strain described above and validated by shake flask and deep-well plate fermentation. The fermentation conditions were optimized such that CarB4_GTG template reproducibly have ~65% FALC conversion in both fermentation platforms as described in Example 5. Results for shake flask fermentation are shown in FIG. 15.

Additional sites (18, 19, 22, 28, 80, 87, 90, 143, 212, 231, 259, 292, 396, 416, 418, 530, 541, 574, 612, 636, 677, 712, 750, 799, 809, 810, 870, 936, 985, 986, 1026, 1062, 1080, 1134, 1149, 1158, 1161, 1170) containing mutations in the improved CarB variants (Table 7) were subjected to full saturation mutagenesis. Primers containing the degenerate nucleotides NNK or NNS were used to mutate these positions to other amino acids by a PCR-based method (Sawano and Miyawaki 2000, Nucl. Acids Res. 28: e78). Saturation library was constructed using the pBZ1 (pACYCDuet-1_P$_{TRC1}$-carB4GTG_rrnBter_ccdAB) plasmid template. Mutant clones were transformed into NEB Turbo (New England Biolab) cloning strains and plasmids were isolated and pooled. The pooled plasmids were then transformed into a V668 based strain carrying plasmid pLYC4 and the transformants were selected on LB agar plates supplemented with antibiotics (100 mg/L spectinomycin and 34 mg/L chloramphenicol).

CarB variants from the saturation library were then screened for the production of fatty alcohols. Single colonies were picked directly into 96-well plates according to a modified deep-well plate fermentation protocol as described in Example 5. Hits were selected by choosing clones that produced a smaller total free fatty acid titer and a larger total fatty alcohol titer compared to the control strain. To compare hits from different fermentation batches, the conversion of free fatty acids to fatty alcohols was normalized by calculating a normalized free fatty acid percentage. The NORM FFA (%) was also used in hits validation as described in Example 5. NORM FFA (%)=Mutant Percent FFA/Control Percent FFA; where "Percent FFA" is the total free fatty acid species titer divided by the total fatty species titer. Hits were subjected to further validation using shake-flask fermentations as described in Example 5. The normalized free fatty acid (NORM FFA) column indicates the improvement in the enzyme, with lower values indicating the best improvement. "Hit ID" indicates the primary screening plate well position where the lower NORM FFA phenotype was found. Hits mutations were identified by sequencing PCR products amplified from "Hit" containing pBZ1 plasmids using mutant carB gene-specific primers (BZ1 for 5'-GGATCTC-GACGCTCTCCCTT-3' (SEQ ID NO:55) and BZ12_ccdAB unique primer 5'-TCAAAAACGCCATTAACCTGATGT-TCTG-3' (SEQ ID NO:56). The NORM FFA values and mutations identified in validated hits are summarized in Table 12.

TABLE 12

Beneficial Mutations in CarB4 Enzyme identified During Amino Acid Saturation Mutagenesis

| WT Amino Acid | WT Codon | Hit ID(Amino Acid) | Mutant Codon | NORM FFA(%) |
|---|---|---|---|---|
| D18 | GAT | P10H5(R) | AGG | 75.5 |
|  |  | P6B4(L) | CTG | 89.6 |
|  |  | P4H11(T) | ACG | 80.8 |
|  |  | P8D11(P) | CCG | 81.8 |
| S22 | AGC | P1F9(R) | AGG | 57.7 |
|  |  | P2G9(R) | AGG | 55.7 |
|  |  | P2A7(N) | AAC | 90 |
|  |  | P8D7(G) | GGG | 82.1 |
| L80 | CTG | P8H11(R) | AGG | 87.4 |
| R87 | CGT | P7D7(G) | GGG | 85.2 |
|  |  | P5D12(E) | GAG | 89.4 |

TABLE 12-continued

Beneficial Mutations in CarB4 Enzyme identified During Amino Acid Saturation Mutagenesis

| WT Amino Acid | WT Codon | Hit ID(Amino Acid) | Mutant Codon | NORM FFA(%) |
|---|---|---|---|---|
| D750 | GAT | P8F11(A) | GCG | 87.6 |
| I870 | ATT | P3A12(L) | CTG | 76.6 |

Identification of Novel Variants of CarB Enzyme by Full Combinatorial Mutagenesis:

A full combinatorial library was constructed to include the following amino acid residues: 18D, 18R, 22S, 22R, 473H, 473I, 827R, 827C, 870I, 870L, 926V, 926A, 926E, 927S, 927K, 927G, 930M, 930K, 930R, 1128L, and 1128W. Primers containing native and mutant codons at all positions were designed for library construction by a PCR-based method (Horton, R. M., Hunt, H. D., Ho, S. N., Pullen, J. K. and Pease, L. R. 1989). Beneficial mutations conserved in CarB2, CarB3, and CarB4 (20R, 288G, and 535S) were not changed, therefore, carB2GTG cloned into pBZ1 (modified pBZ1_P$_{TRC1}$_carB2GTG_ccdAB) was used as PCR template. Library construction was completed by assembling PCR fragments into CarB ORFs containing the above combinatorial mutations. The mutant CarB ORFs were then cloned into the pBZ1 backbone by In-Fusion method (Clontech). The In-Fusion product was precipitated and electroporated directly into the screening strain carrying plasmid pLYC4. Library screening, deep-well plate and shake flask fermentation were carried out as described in Example 5. The activities (NORM FFA normalized by CarB2, 100%) of CarB mutants with specific combinatorial mutations are summarized in Table 13. CarB2, CarB4, and CarB5 (CarB4-S22R) are included as controls. The NORM FFA column indicates the improvement in CarB enzyme, with lower values indicating the best improvement. The fold improvement (X-FIOC) of control (CarB2) is also shown. All mutations listed are relative to the polypeptide sequence of CarB wt (SEQ ID NO:7). For example, CarB1 has A535S mutation, and the CarBDead (a catalytically inactive CarB enzyme) carries S693A mutation which destroys the phosphopantetheine attachment site.

Novel CarB Variants for Improved Fatty Alcohol Production in Bioreactors:

The purpose of identifying novel CarB variants listed in Table 13 is to use them for improved fatty alcohol production. The top CarB variant (P06B6-S3R, E20R, S22R, F288G, Q473H, A535S, R873S, S927G, M930R, L1128W) from Table 13 carries a spontaneous mutation (wild type AGC to AGA) at position 3. Both P06B6 CarB variants, namely CarB7 (amino acid R by AGA at position 3-S3R, E20R, S22R, F288G, Q473H, A535S, R873S, S927G, M930R, L1128W), and CarB8 (wild type amino acid S by AGC at position 3—E20R, S22R, F288G, Q473H, A535S, R873S, S927G, M930R, L1128W) were made and cloned into the low copy number fatty alcohol production plasmid backbone pCL1920 to generate the following fatty alcohol operons differing only in CarB. The translation initiation codon (GTG) for all CarB variants (CarB2, CarB7, and carB8) was reverted to ATG to maximize expression.

pCL1920_P_{TRC}_carB2_tesA_alrAadp1_fabB
[A329G]_fadR pCL1920_P_{TRC}_carB7_tesA_alrAadp1_fabB
[A329G]_fadR pCL1920_P_{TRC}_carB8_tesA_alrAadp1_fabB[
A329G]_fadR The above described plasmids were transformed into a V668 based strain with one copy of chromosomal TE, and the resulted strains were screened in bioreactors as described in EXAMPLE 4. The improvement (measured by % fatty alcohols in the bioreactor fermentation product) of CarB7 and CarB8 over CarB2 was shown in FIG. 16. The order of activity is CarB7>CarB8>CarB2. The position 3 mutation of CarB7 (AGC to an AGA R rare codon) conferred higher activity than CarB8, in addition, SDS-PAGE analysis of total soluble proteins revealed higher expression of CarB7 than CarB8 and CarB2. The expression levels of CarB2 and CarB8 were similar. This is consistent with the CarB60 data described in EXAMPLE 6, both the position 3 AGA R rare codon mutation and the CarB60 tag at its N-terminus can improve CarB expression. It is understood that the CarB7 and CarB8 will perform better than CarB2 in strains with increased free fatty acids flux by either engineering the host strains and/or engineering the other components of the fatty alcohol production operon.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure. It is to be understood that the terminology used herein is for the purpose of describing particular embodiments only, and is not intended to be limiting. Preferred embodiments of this disclosure are described herein. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

TABLE 13

Summary of CarB Variants Identified from Combinatorial Library in Dual-Plasmid system.

| Mutants | NORM FFA (%) | X-FIOC | Mutations |
|---|---|---|---|
| P06B6 | 16.5 | 6.06 | S3R, E20R, S22R, F288G, Q473H, A535S, R873S, S927G, M930R, L1128W |
| P13A3 | 23.9 | 4.18 | D18R, E20R, S22R, F288G, Q473I, A535S, S927G, M930K, L1128W |
| P02A2 | 26.5 | 3.77 | E20R, S22R, F288G, Q473I, A535S, R827C, V926E, S927K, M930R |
| P05H3 | 26.7 | 3.75 | D18R, E20R, 288G, Q473I, A535S, R827C, V926E, M930K, L1128W |
| P10F10 | 31.9 | 3.13 | E20R, S22R, F288G, Q473H, A535S, R827C, V926A, S927K, M930R |
| P01C12 | 34.2 | 2.92 | E20R, S22R, F288G, Q473H, A535S, R827C |
| P03B1 | 36.9 | 2.71 | E20R, S22R, F288G, Q473I, A535S, R827C, M930R |
| P06E4 | 36.9 | 2.71 | E20R, S22R, F288G, Q473I, A535S, I870L, S927G, M930R |
| P14C6 | 37.4 | 2.67 | E20R, S22R, F288G, Q473I, A535S, I870L, S927G |
| P05F10 | 40.4 | 2.48 | D18R, E20R, S22R, F288G, Q473I, A535S, R827C, I870L, V926A, S927G |
| P06C8 | 40.8 | 2.45 | E20R, S22R, F288G, Q473H, A535S, R827C, I870L, L1128W |
| P15E4 | 40.8 | 2.45 | D18R, E20R, S22R, F288G, Q473H, A535S, R827C, I870L, S927G, L1128W |
| P05H7 | 40.9 | 2.44 | E20R, S22R, F288G, Q473I, A535S, R827C, I870L, S927G, L1128W |
| P15A6 | 41 | 2.44 | E20R, S22R, F288G, Q473I, A535S, R827C, I870L, S927G, M930K, L1128W |
| P08F5 | 41.2 | 2.43 | E20R, S22R, F288G, Q473H, A535S, I870L, S927G, M930K |
| P14C7 | 41.3 | 2.42 | E20R, F288G, Q473I, A535S, I870L, M930K |
| P16H10 | 42.1 | 2.38 | E20R, S22R, F288G, Q473H, A535S, S927G, M930K, L1128W |
| P16A1 | 44.1 | 2.27 | D18R, E20R, S22R, F288G, Q473I, A535S, S927G, L1128W |
| P14H4 | 44.2 | 2.26 | E20R, S22R, F288G, Q473I, A535S, , R827C, I870L, S927G |
| P15C1 | 46.5 | 2.15 | D18R, E20R, S22R, F288G, Q473I, A535S, R827C, I870L, S927G, L1128W |
| P16E5 | 47.2 | 2.12 | D18R, E20R, S22R, F288G, Q473I, A535S, S927G, M930R, L1128W |
| P15A3 | 47.2 | 2.12 | E20R, S22R, F288G, Q473H, A535S, V926E, S927G, M930R |
| P05A2 | 52.4 | 1.91 | E20R, S22R, F288G, Q473H, A535S, R827C, I870L, V926A, L1128W |
| CarB2 | 100 | 1 | E20R, F288G, Q473I, A535S |
| CarB4 | 77.8 | 1.29 | E20R, F288G, Q473H, A535S, R827A, S927G |
| CarB5 | 48.9 | 2.04 | E20R, S22R, F288G, Q473H, A535S, R827A, S927G |
| CarB1 | ND | | A535S |
| CarB wt | ND | | SEQ ID NO: 7 |
| CarBDead | ND | | S693A |

TABLE 14

| SEQ ID NO | Description | Sequence |
|---|---|---|
| 1 | cat-loxP-T5 (in front of iFAB138) | TTGTCCATCTTTATATAATTTGGGGTAGGGTGTTCTTTATGTAAAAAAAC gtttTAGGATGCATATGGCGGCCGCataacttcgtataGCATACATtacgaagttaTCTAGA GTTGCATGCCTGCAGGtcgccgcttattatcacttattcaggcgtagcAaccaggcgttaaggcgcaccataactg cctaaaaaaattacgccccgccctgccactcagcgcagtagttaattcattaagcattctgccgacatggaagccatcaca aacgcatgatgaacctgaatcgccagcggcatcagcaccttgtcgccttgcgtataaatatttgcccatggtgaaaacggg cgaagaagttgtccatattggccacgtttaaatcaaaactggtgaaactcacccaggattgctgagacgaaaacatattctc aataaacccttagggaaataggccaggttttcaccgtaacacgccacatcttgcgaatatatgtgtagaaactgccggaaatcg tcgtgtattcacctcccagacgcgatgatggtttcagtcgttgaaaacgggtgaacaaggtgaacaactacatccatca ccagtcaccgtctttcattgccatacggttcctataccggtagatcttcggatgacgcgttcatcaggccgggcaagcggcgaatgtcgggacaagtcccgattaaccggccgggcaagcggcgaatgtgggcagaagctcgttgatgtcgtgttatagtgagcaactgactg aaatgcctcaaaatgttctttacgatgccaatgcctctaaaaggcgctataaatccaacggtggtatatccagtggttctccagtgatttttctccattagctccttagct cctgaaactcgataactcaaaaatacgcccgtagcgagtgtatattcttcattatggtgaaagttgaacttctacgtgccgatca acgtccatttcgccaaagttggccaaggcttccccgatactctgcaacaggacaaccaggattatttctccgaagtgatcttc cgtcacaggtattattcGACTCTAGataacttcgtataGCATACATTATACGAAGTTATGGATC CAGTTTATCGATACCGTCaaacAATACTAAAAAATTCATTATTTGCITTcaggaggagag tctgTATAATAGATTCAATTGCATGACGACGAACACGCACCTGCAGGAGGAG ACCATGATCATCAAACCTAAAATTCGTGATTTATC |
| 2 | T5 (in front of iFAB138) | TTGTCCATCTTTATATAATTTGGGGTAGGGTGTTCTTTATGTAAAAAAAC gtaTAGGATGCATATGGCGGCCGCataacttcgtataGCATACATTATACGAAGTTAT GGATCCAGCTTATCGATACCGTCaaacAATACATAAAAATTATTTTGCTTCa ggaaaattttctGTATAATAGATTCAATTGCATGACGACGAACACGCACCTGCAG GAGGAGACCAATGATCATCAAACCTAAAATTCGTGATTTATC |
| 3 | AlrA Acinetobacter sp. M-1 | MSNHQIRAYAAMQAGEQVVPYQFDAGELKAHQVEVKVEYCGLCHSDLSVINN EWQSSVYPAVAGHEIIGTIIALGSEAKGLKLIGQRVGIGWTAETCQACDPCIGGN QVLCTGEKATIIGHAGGFADKVRAGWQWVIPLPDDLDPESAGPLLCGGITVL DPLLKHKIQATHHVGVIGIGGLGHIAIKLLKAWGCEITAFSSNPDKTEELKANGA DQVVNSRDAQAIKGTRWKLIILSTANGTLNVKAYLNTLAPKGSLHFLGVTLEPI PVSVGAIMGGAKSVTS SPTGSPLALRQLIQFAARKNIAPQVELFPMSQLNEAIER LHSGQARYRIVLKADFD |
| 4 | AlrAadp1 | MATTNVIHAYAAMQAGEALVPYSFDAGELQPHQVEVKVEYCGLCHSDVSVLN NEWHSSVYPVVAGHEIVIGTITQLGSEAKGLKIGQRVGIGWTAESCQACDQCISG QQVLCTGENTATIIGHAGGFADKVRAGWQWVIPLPDELDPTSAGPLLCGGITVF DPILKHQIQAIHHVAVIGIGGLGHMAIKLLKAWGCEITAFSSNPNKTDELKAMG ADHVNSRDDAEIKSQQGKFDLLLSTVNVPLNWNAYLNTLAPNGTFHFLGVV MEPIPVPVGALLGGAKSLTASPTGSPAALRKLLEFAARKNIAPQIEMY |
| 5 | yjgB | atgTCGATGATAAAAGCTATGCCGCAAAAGAAGCGGGCGGCGAACTGGAA GTTTATGAGTACGATCCCGGATCCGCCAAGATGTTGAAGTGCAG GTGGATTACTGCGGGATCTGCCATTCGATCTGTCGATGATCGATAACGAAT GGGGATTTTCACAATATCCCTGGTTGCCGGGCATGAGGTGATTGGGCGCG TGGTGGCACTCGGGAGCCGCCGCGCAGGATAAAGGTTTGCAGGTCGGTCAGC GTGTCGGGATTGGCTGGACCGCGGCTAGCTGTGTCACTGCGACCGCTGTA |

TABLE 14-continued

Sequences

| SEQ ID NO | Description | Sequence |
|---|---|---|
| | | TTAGCGGTAATCAGATCAACTGCGAGCAAGGTGCCGTGCCGACGATTATGA<br>ATCGCGGTGGCTTTGCCGAGAAGTTGCCTGCCGACTGGCAATGGGTGATTC<br>CACTGCCAGAAAATATTGATATCGAGTCCCGCCGGCCGCTGTTGCCGGCG<br>GTATCACGGTCTTTAAACCACTGTTGATGCACCATATCACTGCTACCAGCCG<br>CGTTGGGGTAATTGTATTGCGGCCTGGGCATATCGCTATAAAACTTCTG<br>CACGCAATGGGATGCGAGTGACAGCCTTTAGTTCTAATCCGGCGAAAGAG<br>CAGGAAGTGCTGGCCATGGGTGCCGATAAAGTGTGAATAGCCGCGATCCG<br>CAGGCACTGAAAGCACTGGCGGGCCAGTTTGATCTCATTATCAACACCGTC<br>AACGTCAGGCCTGACTGGCCAGCCCTATTTTGAGGCGCTGACCTATGGCGTA<br>ATTTCCATACGGTCCGTGCCGTTCTCACGCCGCTCTGTTCCCGGCCTTTAC<br>GTTAATTGCGGGCGATCGCAGCGTCCTGCTTCTGCTACCGGCACGCCTTAT<br>GAGCTGCGTAAGCTGATGCGTTTTGCCCGCCAGCAAGGTTGCCCGACC<br>ACCGAACTGTTCCCGATGTCGAAAATTAACGACGCATCCAGCATGTGCGC<br>GACGGTAAGGCGCGTTACCCGCTGTGTTGAAAGCCGATTTTtga |
| 6 | NRRL 5646 CAR | MAVDSPDERLQRRIAQLFAEDEQVKAARPLEAVSAAVSAPGMRLAQIAATVM<br>AGYADRPAAGQRAFELNTDDATGRTSLRLLPRFETITYRELWQRVGEVAAAW<br>FIHDPENPLRAGDFVALLGFTSIDYATLDLADIHIGAVTVPLQASAAVSQLIAILT<br>ETSPRLLASTPEHLDAAVECLLAGTTPERLVVFDYHPEDDDQRAAFESARRRLA<br>DAGSLVIVETLDAVRARGRDLPAAPLFVPDTDDDPLALLIYTSGSTGTPKGAMY<br>TNRLAATMWQGNSMLQGNSQRVGINLNYMPMSHIAGRISLFGVLARGGTAYF<br>AAKSDMSTLFEDIGLVRPTEIFFVPRVCDMVFQRYQSELDRRSVAGADLDTLDR<br>EVKADLRQNYLGGRPFLVAVVGSAPLAAEMKTFMESVLDLPLHDGYGSTEAGA<br>SVLLDNQIQRPPVLDYKLVDVPELGYFRTDRPHPRGELLLKAETTIPGYYKRPE<br>VTAEIFDEDGFYKTGDIVAELEHDRLVYVDRRNNVLKLSQGEFVTVAHLEAVF<br>ASSPLIRQIPIYGSSERSYLLAVIVPTDDALRGRDTATLKSALAESIQRIAKDANL<br>QPYEIPRDFLIETEPFTIANGLLSGIAKLLRPNLKERYGAQLEQMYTDLATGQAD<br>ELLALRREAADLPVLETVSRAAKAMLGVASADMRPDAHFTDLGGDSLSALSFS<br>NLLHEIFGVEVPVGVVVSPANELRDLANYIEAERNSGAKRPTFTSVHGGGSEIR<br>AADLTLDKFIDARTLAAADSIPHAPVPAQTVLLTGANGYLGRFLCLEWLERLD<br>KTGGTLICVVRGSDAAAARKRLDSAFDSGDPGLLEHYQQLAARTLEVLAGDIG<br>DPNLGLDDATWQRLAETVDLIVHPAALVNHVLPYTQLFGPNVVGTAEIVRLAI<br>TARRKPVTYLSTVGVADQVDPAEYQEDSDVREMSAVRVVRESYANGYGNSK<br>WAGEVLLREAHDLCGLPVAVFRSDMILAHSRYAGQLNVQDVFTRLILSIVATG<br>IAPYSFYRTDADGNRQRAHYDGLPADFTAAAITALGIQATEGFRTYDVLNPYD<br>DGISLDEFVDMLVESGHPIQRITDYSDWFHRFETAIRALPEKQRQASVLPLLDAY<br>RNPCPAVRGAILPAKEFQAAVQTAKIGPEQDIPHLSAPLIDKYVSDLELLQLL* |
| 7 | carB | MTSDVHDATDGVTETALDDEQSTRRIAELYATDPEFAAAAPLPAVVDAAHKPG<br>LRLAEILQTLFTGYGDRPALGYRARELATDEGGRTVTRLLPRFDTLTYAQVWS<br>RVQAVAAALRHNFAQPIYPGDAVATIGFASPDYLTLDLVCAYLGLIVSVPLQHN<br>APVSRLAPILAEVEPRILTVSAEYLDLAVESVRDVNSVSQLVVFMHPEVDDHR<br>DALARAREQLAGKGIAVTTLDAIADEGAGLPAEPIYTADHDQRLAMILYTSGST<br>GAPKGAMYTEAMVARLWTMSFITGDPTPVINVNMFPLNHLGGRIPISTAVQNG<br>GTSYFVPESDMSTLFEDLAIVRPTELGLVPRVADMLYQHHLATVDRLVTQGAD<br>ELTAEKQAGAELRLREQVLGGRVITGFVSTAPLAAEMRAFLDITLGAHIVDGYGLT<br>ETGAVTRDGVIVRPPVIDYKLIDVPELGYFSTDKPYPRGELLLVRSQTLTPGYYKR |

TABLE 14-continued

| SEQ ID NO | Description | Sequence |
|---|---|---|
| | | PEVTASVFDRDGYYHTGDVMAETAPDHLVVVDRRNNVLKLAQGEFVAVANL<br>EAVFSGAALVRQIFVYGNSERSFLLAVVVPTPEALEQYDPAALKAALADSLQRT<br>ARDAELQSYEVPADFIVETEPFSAANGLLSGVGKLLRPNLKDRYGQRLEQMYA<br>DIAATQANQLRELRRAAATQPVIDTLTQAAATILGTGSEVASDAHFTDLGGDSL<br>SALTLSNLLSDFFGFEVPVGTIVNPATNLAQLAQHIEAQRTAGDRRPSFTTVHGA<br>DATEIRASELJTLDKFIDAETLRAAPGLPKVTTEPRTVLLSGANGWLGRFLJTLQW<br>LERLAPVGGTLIITIVRGRDDAAAARLTQAYDTDPELSRFAELADRHLRVVA<br>GDIGDPNLGLTPEIWHRLAAEVDLVVHPAALVNHVLPYRQLFGPNVVGTAEVI<br>KLALTERIKPVTYLSTVSVAMGIPDFEEDGDIRTVSPVRPLDGGYANGYGNSKW<br>AGEVLLREAHDLCGLPVATPRSDMILAHPRYRGQVNVPDMFTRLLLSLLITGVA<br>PRSFYIGDGERPRAHYPGLTVDFVAEAVTTLGAQQREGVSYDVMNPHDDGIS<br>LDVFVDWLIRAGHPIDRVDDYDDNVRRFETALJTALPEKRRAQTVLPLLHAFRA<br>PQAPLRGAPEPTEVFHAAVRTAKVGPGDIPHLDEALIDKYIRDLREFGLI* |
| 8 | PPTase is EntD from *E. coli* MG 1655 | MVDMKTTHTSLPFAGHTLHFVEFDPANFCEQDLLWLPHYAQLQHAGRKRKTE<br>HLAGRIAAVYALREYGYKCVPAIGELRQPVWPAEVYGSISHCGTTALAVVSRQ<br>PIGIDIEEIFSVQTARELITDNIITPAEHERLADCGLAFSLALTLAFSAKESAFKASEI<br>QTDAGFLDYQIISWNKQQVIIHRENEMFAVHMQIKEKIVITLCQHD* |
| 9 | Del-/ac/F-F | AAAAACAGCAACAATGTGAGCTTTGTTGTTAATTATTATTGTAAACATATTGAT<br>TCCGGGATCCGTCGACC |
| 10 | Del-fadE-R | AAACGGAGCCTTTCGGCTCCGCTTATTCATTTACGCGGCTTCAACTTTCCTGT<br>AGGCTGGAGCTGCTTC |
| 11 | fadE-L2 | CGGGCAGGTGCTATGACCAGGAC |
| 12 | fadE-R1 | CGCGGCGTTGACCGCAGCCTGG |
| 13 | iFAB138 (DNA) | TGTAGCTGGAGCTGCTTCGAAGTTCCTATACTTTCTAGAGAATAGGAACTT<br>CGGAATAGGAACTTCGAACTGCAGGTCGACGGATCCCCGGAATATTTAAAT<br>CATTTGTACTTTTTGAACAGCAGAGTGCATTATGCCACCGAAGCCAGGC<br>TGTTGGACAGAACGTAGTTGACTTTCGCATTACCGGCCCTTCGTTAGGAACGTA<br>ATCCAGGTCGCATTCCGGATCCGCCTCTTTTGACGATGGTCGGCGGAATG<br>AAACCCTCTTCAATAGCTTTGGCACAGATAATCGCTTCGACTGCACCGCCAG<br>CGCCCAGCAGGTGGCCGGTCATGCTTCGTCTTGGTGCTAGACACCGGCACTTTGTA<br>GGCGTATTCACCCAGGACCGTGCGGGCGTTGAATAGGAAATGTCCTCTGGCGGA<br>TACGCCGTCGCCGTGCCGTTCAGTTTCATTGCCACGTGCACCATAGCCAACG<br>CATTATTCTTCTTCCATTGCGTGATATGCTGCCAGGTCGCACCATAGCCAACG<br>GGCGCTGGCTCTGCTGTAGATTTGGCACCACGCTTCAGCGCGTGCTCCAACTCTTCCA<br>ATCTCGGCATAGATTTGGCACCACGCTTCAGCGCGTGCTCCAACTCTTCCA<br>AGATAACGATACCCGCTGCCCTGCCCATCACAACAAACCGCTGCGATCCTTATC<br>GAACGGGATGCTGGCGCGCTTCGGGTCCTCAGATTTGGTCACGGCCTTTATC<br>GAGGCAAAACCCGCCAGGCTCAACGGGGTGATACCTGCTTCGCTACCACCA<br>GAGATCATAACGTGCTATAACCAAACTTAATGTTACGGAGGACTCACCA<br>ATGCTGTTGTTCGGCTCCACAATGCGGTGACAATGGTCGTGCAAATACCTT<br>TAGCCCATAACGAATCGCCAGATTGCCGTTGCCATATCGCCAATGATCAT |

TABLE 14-continued

Sequences

| SEQ ID NO | Description | Sequence |
|---|---|---|
| | | CGGAATAGTCATAGGGCTCACACGACCCGACCTTTGGTAATCAGCTTTCA |
| | | TCCTGCTTCTCAATGGTGCCGATGCCGCCAATGCCGCTACCAACAATGACGC |
| | | CGAAACGATTCTTATCAATCGACTCCAGTTGCTGTCGTCCTTGATTGC |
| | | CTCATCCGCCAACGATCGCAAACTGGCTAAAACGGTCCATACGGTTCGC |
| | | CTCACGCTTGTCGATAAAGTCTCCGGGTGAAGTCCTTCACTTCGGCAGCC |
| | | AGCTTAACTTTGAAATCGGTTGCGTCAAACGCTTTGATCTTGTCAATGCCAC |
| | | ATTTACCCTCTTTGATGCTGCACCAGAAGCTATCAGCGTTGTTACCCACGG |
| | | CGTCACTGCACCAATACCCGTAATGACAACGCGGCGATTCATTttgtgcctccttTT |
| | | Agaacgcggaagtatccgtgaacaacaacgatcgtgcggtatagatcaggcgaccatccaccagaacctcacc |
| | | gtcccgccagccatgatcaggcgacggtttacgtacgtagaaatgaatacgataggtgacttttcctggctgtcgtcggcagaac |
| | | ctggccggtaaattcaacttcgcccacgccagagcgcggcctagcctcgccgcccaaccagccaggtagaatcccacc |
| | | aattgccacatagcatccagaccagacaaccgggcatccagcgatcgccgataaagtggcatccgaagaaccatagatcc |
| | | ggattgatatccagctcggcttcggacatagccgctttgtcgaaattgccggtcatcttaacgacgccggtccatcatcag |
| | | catgttcggtgcaggagttgcggccctttagcgccaaacagttcaccagaccaagaaggtcttccttttgtatagga |
| | | ttccgttatctaccatgttttatgtaaaccttaaaaTTAAACCATGTACATTCCGCCGTTGACGTGC |
| | | AGAGTCTCACCAGTGATGTAACTCGCTTCGTCAGAGGCTAAAAATGCAACC |
| | | GCACTGGCGATTTCTGAGCGCCGCGAGGCGACCCGCAGGCACCTGCGCC |
| | | AGGATACCCGCACGCTGATCGTCAGACAGCGCACGCGTCATGTCCGTTTCA |
| | | ATAAAACCCGAGCCACACATTGACACAGTAATACCACGGACGCAACTTCA |
| | | CGCGCCAGTGATTTACTGAAACCGATCAGCCCGCTTTCGCCGCAGCGTAGT |
| | | TTGCCTGACCTGCATTTCCCATGGTACCAACCACAGAACCAATAGTGATAAT |
| | | GCGACCACACAGCTTTTTCATCATAGCGCCGCCATTACCGCTTTGACAGGCGG |
| | | AAAACGGATGATAAGTTGGTTTCGATAATATCGTTCCACTCATCATCTTTCA |
| | | TTCGCATCAACAGATTATCACGAGTGATACGGCATTATTAACCAGGATATC |
| | | CACTTCACCCAAATTCTGCGCAGAATATTTTCCGAGTCAGATTCAATAGATGCA |
| | | GGATCGGTCACATTCAACATCAAACCTTTCCGTTAGCACTACTAAATAGTGC |
| | | TAATGTTCTTCGCACCATTTTCACTGGTCCGCAGTCCCGATAACTTTCGCGCC |
| | | GCGGGCAACGAGAGTCTCTGCAATTGCGCGGCCTATGCCACGGCTTGCACC |
| | | AGTCACCAGCGCAATCTTTCCTTCAAAGCTCATGGTTTTCCTCTTTTATTGCG |
| | | TAAGTGCCGAGACAGCCGCCGGCTCGTTCAGCGCCGCGACGCTGTCAGGG |
| | | TGTCCACAATACGTTTCGTCAGACCAGTGAGGACTTTACCTGGACCCACTTC |
| | | ATAAAGATGTTCAACGCCTGCGCCCGCGATAAATTCCACGCTCTTCGTCCAC |
| | | TGTACCGGATTGTACAACTGGCGAACCAGCGCATCGCGGATAGCGCGGCA |
| | | TCGGTTTCACATTTCACGTCAAACGTGTTCACTACCGCCAGCCGTTGGCGCGC |
| | | TAAAGGTAATTTTGGCGACGGTAATTCAACCGCCAGCTTTATCTCGCCGCTGTTTCAT |
| | | CAGCGGCGCAGTGCGACGGTACGCTCACCGGCAGCGGCAGCGCGCTTTCGC |
| | | GCCAGCGGCTTTACAGGCTGCGCCCGCGAGTTAAGTTAACCGGCGAAACAACCTGC |
| | | CCTTCGGCAGATTCTTCACAGGCTTTAGCAATAGAGGCATCATCCAGCCGA |
| | | TGATCGCAGACATGCCGCCAGTGCCTTCCGGAACCGCTTCCTGCATGAATTT |
| | | ACCGCGCATTTCCACCAGACGAACGGCATCAGCAAAGTTGATGACGCCAGC |
| | | GCAAACCAGCCGGAATATTCGCCCAGGCTGTGACCTGCCATTAACGCAGG |
| | | CATTTTACCGCCCTCTGCTGTCCAAACGCGCCAAAGCGCCAAAGCGGAAGCGGT |
| | | TAATAACGCCGGCTGCGTCTGCCACAGGTTTTATTCAGTTCTTCCGCTGACCT |
| | | TGCTGGGTGAGCGCCCACAGATCATATCCCAGAGCCGCAGAAGCTTCAGCA |
| | | AACGTTCTTCTACGATAGGGTAATTTGCGCCATCTCCGCCACATCCCAA |
| | | CGCTCGAGAACCCTGACCGGGACACAAATGCAAATTGCGTCATGTTTA |

TABLE 14-continued

| SEQ ID NO | Description | Sequence |
|---|---|---|
| 14 | DG150 | AATCCTTATACTAGAAACGAATCAGCGCGGAGCCCCAGGTGAATCCACCCC<br>CGAAGGCTTCAAGCAATACCAGCTGACCGGCTTTAATTCGCCCGTCACGCA<br>CGGCTTCATCCAGCGCGACGCACGGCACAGAGCCGCGGAGGTATTGCCGTGCC<br>TGTCCAGCGTGACGACGACATTGTCCATGCACATGCCAGTTTTTCGCTGT<br>CGCGCTAATGATACGCCAGGTTAGCCTGAGTCGGGACCAGCCAATCGAGTTC<br>TGAGCGGATCCAGGTTATTAGCCGCCAGCGTCTCATCGACAATATGCGCCAGT<br>TCAGTGACCGCCACTTTAAAGACTTCATTGCCCGCCATTGTCAGTAAATCG<br>GGTTATCCGGATTTACGCGATCGGCATTCGGACAGGGTCAGTAATTCACCGTA<br>ACGGCCATCGGCATGAGAGATGAGTGAGATAATACCCGGTTCTTCAGAAGC<br>GCTCAGTACCGCCGCGCCTCGCCATCGCCGAAAATAATGATCGTACCGCG<br>ATCGCCAGGATCGCAAGTGCGGGCTAATACATCGGAACCGACCACCAGCGC<br>GTGTTTAACCGCCGGATTTAACGTACTGGTCGCGATGCTTAACGCGTAG<br>GTGAAACCTGCGCACGCTGCCGGACATCAAACGCGGGCAACCTTTAATA<br>CCGAGCATACTTTGAATCTGACATGCCGCCTTGAAATCATGCGTTGCTG<br>ATGTGGTAGCCACCACAATCAAGCCAATTTGGTCTTTATCGCGACAGTTTCATTC<br>CTCAATCGCCGCGATTCGCAGCGGTAAAGCCATCGTCGCGACAGTTTCATTC<br>GGCGCGGCGATATGCGTTTACGAATACCTGTACGAGTGACAATCCACTCG<br>TCAGAGGTCTCAACCATTTTTCCAGATCGGCGTTAGTCCACTTGTTCGG<br>GCAGATAGCTGCCAGTATCAATAATCATCAAATTCGACTTCTGGATTGACGTCAGCAT<br>aaaTTACTCGATATCAATCATCAAATTCGACTTCTGGATTGACGTCAGCAT<br>CGTAATCAATGCCTTCAATGCCAAAGCCAAACAGCTTGATGAACTCTTCTTT<br>GTACATGTCGTAATGTCTCAGCTCGCTCGAATGTCATCACGCCAGTTCCCAGTCATCCA<br>CACAGATCACGGCAGTGCTGCTGAATGTCATCACGCCAGTTCCCAGTCATCCA<br>AACGCAGACGATTGTGATCATCCACTTCCGGCGCTGAACCATCT |
| 15 | DG131 | GCAGTTATTGTGCCCTTAAACGCCTGGTTGCTACGCCTG |
| 16 | LC277 | GAGCCAATATGCGAGAACACCCGAGAA |
| 17 | LC278 | CGCTGAACGTATTGCAGGCCGAGTTGCTGACCGTCCCGCCAGCAG |
| 18 | DG407 | GGAATTGCCACGGTGCGGCAGGCTCCATACGCGAGGCCAGGTTATCCAACG |
| 19 | DG408 | AATCACCAGCACTAAAGTGCGCGGTTCGTTACCCG |
| 20 | Primer1 for prep of CarB60 | ATCTGCCGTGGATTGCAGAGTCTATTCAGCTACG |
| 21 | Primer2 for prep of CarB60 | GCAATTCCATATGACGAGCCGATGTTCACGA |
|  |  | CCGCTCGAGTAAATCAGACCGAACTCGCG |

TABLE 14-continued

| SEQ ID NO | Description | Sequence |
|---|---|---|
| 22 | pET15b-carB construct (60 nt directly upstream of the carB gene) | ATGGGCAGCAGCCATCATCATCATCATCACAGCAGCGGCCTGGTGCCGCGC GGCAGCCAT |
| 23 | carB60 amplified from pCL_carB60 forward primer | ACGGATCCCCGGAATGCGCAACGCAATTAATGTaAGTTAGCGC |
| 24 | carB60 amplified from pCL_carB60 reverse primer | TGCGTCATCGCCATTGAATTCCTAAATCAGACCGAACTCGCGCAGG |
| 25 | carB60 amplified from pAH56 forward primer | ATTCCGGGGATCCGTCGACC |
| 26 | carB60 amplified from pAH56 reverse primer | AATGGCGATGACGCATCCTCACG |
| 27 | HZ117 primer | ACGGAAAGGAGCTAGCACATGGGCAGCAGCCATCATCAT |
| 28 | DG264 primer | GTAAAGGATGGACGGCGGTCACCCGCC |
| 29 | DG263 primer | CACGGCGGGTGACCGCCGTCCATCC |
| 30 | HZ118 primer | TTAATTCCGGGGATCCCTAAATCAGACCGAACTCGCGCAGGTC |
| 31 | SL59 primer | CAGCCGTTTATTGCCGACTGGATG |

TABLE 14-continued

Sequences

| SEQ ID NO | Description | Sequence |
|---|---|---|
| 32 | EG479 primer | CTGTTTTATCAGACCGCTTCTGCGTTC |
| 33 | Primer EG58 | GCACTCGACCGGAATTATCG |
| 34 | Primer EG626 | GCATACGCGTACTGTGAGCCAGAG |
| 35 | Primer DG243 | GAGGAATAAACCATGACGAGCGATGTTCACGACGCGACCGACGGC |
| 36 | Primer DG210 | CTAAATCAGACCGAACTCGCGCAGG |
| 37 | Primer DG228 | CATGGTTTATTCCTCCTTATTTAATCGATAC |
| 38 | Primer DG318 | TGACCTGCGCGAGTTCGGTCTGATTTAG |
| 39 | carA (protein) | MTIETREDRFNRRIDHLFETDPQFAAARPDEAISAAAADPELRLPAAVKQILAGY ADRPALGKRAVEFVTDEEGRTTAKLLPRFDTITYRQLAGRIQAVTNAWHNHPV NAGDRVAILGFTSVDYTTIDIALLELGAVSVPLQTSAPVAQLQPIVAETEPKVIAS SVDFLADAVALVESGPAPSRLVVFDYSHEVDDQRREAFEAAKGKLAGTGVVE TITDALDRGRSLADAPLYVPDEADPLTLLYTSGSTGTPKGAMYPESKTATMWQ AGSKARWDETLGVMPSITILNFMPMSHVMGRKGILCSTLASGGTAYFAARSDLST FLEDLALVRPTQLNFVPRIWDMLFQEYQSRLDNRRAEGSEDRAFAAVLEEVRT QLLGGRFVSALTGSAPISAEMKSWVEDLLLDMHLLEGYGSTEAGAVFIDGQIQRP PVIDYKLVDPDLGYFATDRPYPRGELLVKSEQMPGYYKRPEITAEMFDEDG YYRTGDIVAELGPDHLEYLDRRNNVLKLSQGEFVTVSKLEAVFGDSPLVRQIYV YGNSARSYLLAVVVPTEEALSRWDGDELKSRISDSLQDAARAAGLQSYEIPRDF LVETTPFTLENGLLTGIRKLARPKLKAHYGERLEQLYTDLAEGQANELRELRRN GADRPVVETVSRAAVALLGASVTDLRSDAHFTDLGGDSLSALSFSNLLHEIFDV DVPVGVIVSPATDLAGVAAYIEGELRGSKRPTYASVHGRDATEVPARDLALGK FIDAKTLSAAPGLPRSGTEIRTVLLTGATGFLGRYLALEWLERMDLVDGKVICL VRARSDDEARARLDATFDTGDATLLEHYRALAADHLEVIAGDKGEADLGLDH DTWQRLADTVDLIVDPAALVNHVLPYSQMFGPNALGTAELIRIALTTTIKPYVY VSTIGVGVQGISPEAFVEDADIREISATRRVDDSVANGYGNSKWAGEVLLREAHD WCGLPVSVFRCDMLLADTTYSGQLNLPDMFTRLMLSLVATGIAPGSFYELDAD GNRQRAHYDGLPVERIAEAISTIGSQVTDGFETHVMNPYDDGIGLDEYVDWLI EAGYPVHRVDDYATWLSRFETALRALPERQRQASLLPLLHNYQQPSPPVCGAM APTDRFRAAVQDAKIGPDKDIPHVTADVIVKYISNLQMLGLL* |
| 40 | FadD9 (protein) | MSINDQRLTRRVEDLYASDAQFAAASPNEAITQAIDQPGVALPQLIRMVMEGY ADRPALGQRALRFVTDPDSGRTMVELLPRFETIIYRELWARAGTLATALSAEPA IRPGDRVCVLGFNSVDYTTIDIALIRLGAVSVPLQTSAPVTGLRPIVTETEPTMIA |

TABLE 14-continued

Sequences

| SEQ ID NO | Description | Sequence |
|---|---|---|
| | | TSIDNLGDAVEVLAGHAPARLVVFDYHGKVDTHREAVEAARARLAGSVTIDTL |
| | | AELIERGRALPATPIADSADDALALLIYTSGSTGAPKGAMYRESQVMSFWRKSS |
| | | GWFEPSGYPSITLNFMPMSHVGGRQVLYGTLSNGTAYFVAKSDLSTLFEDLA |
| | | LVRPTELCFVPRIWDMVFAEFHSEVDRRLVDGADRAALEAQVKAELRENVLG |
| | | GRFVMALTGSAPISAEMTAWVESLLADVHLVEGYGSTEAGMVLNDGMVRRPA |
| | | VIDYKLVDVPELGYFGTDQPYPRGELLVKTQTMPFGYYQRPDVTAEVFDDPGF |
| | | YRTGDIMAKVGPDQFVYLDRRNNVLKLSQGEFIAVSKLEAVFGDSPLVRQIFIY |
| | | GNSARAYPLAVVVPSGDALSRHGIENLKPVISESLQEVARAAGLQSYEIPRDFIIE |
| | | TTPFTLENGLLTGIRKLARPQLKKFYGERLERLYTELADSQSNELRELRQSGPDA |
| | | PVLPTLCRAAAALLGSTAADVRPDAHFADLGGDSLSALSLANLLHEIFGVDVPV |
| | | GVIVSPASDLRALADHIEAARTGVRRPSFASIHGRSATEVHASDLTLDKFIDAAT |
| | | LAAAPNLPAPSAQVRTVLLTGATGFLGRYLALEWLDRMDLVNGKLICLVRARS |
| | | DEEAQARLDATFDSGDPYLVRHYRELGAGRLEVLAGDKGEADLGLDRVTWQR |
| | | LADTVDLIVDPAALVNHVLPYSQLFGPNAAGTAELLRLALTGKRKPYIYTSTIA |
| | | VGEQIPPEAFTEDADIRAISPTRRIDDSYANGYANSKWAGEVLLREAHEQCGLP |
| | | VTVFRCDMILADTSYTGQLNLPDMFTRLMLSLAATGIAPGSFYELDAHGNRQR |
| | | AHYDGLPVEFVAEAICTLGTHSPDRFVTVHVMNPYDDGIGLDEFVDWLNSPTS |
| | | GSGCTIQRIADYGEWLQRFETSLRALPDRQRHASLLPLLHNYREPAKPICGSIAP |
| | | TDQFRAAVQEAKIGPDKDIPHLTAAIIAKYISNLRLLGLL* |
| 41 | carA (DNA) | atgacgatcgaaacgcgaagaccgcttcaacccggccgcattgaccacttgttcgaaaccgaccgcagttcgccgcgcc |
| | | cgtccgacgcaggccatcagccgcgtcgccgcctgcggcgatccggagttcgcctcctgcccggcgtcaacagattctggccggc |
| | | tatgcggaccgcctgcctgggcaagcgccgtcgagttcgtcaccgacgaagaaggccgcaccaccgcgaagctct |
| | | gccccgctcgacaccatccacctaccgtcagtcgcaggccggatccgactacaccagtgctgacaatgctggcacaacatccggt |
| | | gaatgccgtgaccggctggctgccatcctgggtacaccagtcgactctcgggatcgacatcgccctgctcgaactcggc |
| | | gccgtcctgctaccgtcgagaccagcgtccggtggccgtcggccgatcgccgagaccgagccaaggtgat |
| | | cgcgtccagcgtcgactctcctcgcgacagtcctctcgtcgagtcggagtcggcgggccaagctcgaggtcaaggtcgtgttcgac |
| | | tacagccacgaggtcgacgatcagcgtgaaggcgtcactcgccgacgaccgcctacgtccgacgcaccgcgagcgaccgt |
| | | agacgatcaccgaccgtaccccccggccgccctgcccgagcccgaagccgcgatgccagtccaagacaccgcacgatgtg |
| | | gcaggccgggtccaaggccggcatcgtgtggaacgagacgatccgccaccccggtcgatcaccctgaacttcatgccatgagtca |
| | | cgtcatgggcgccggcaccctgtcagcaacctcgtgcggccaacgcagtcaacttcgtcctcgcatctcgggacaatgctgttccaggagtacc |
| | | cctttcctggaggaccttccgcctcgtgccggcaacgagtcaacgccggccccacgccaagcccagttcgccgaaggctccgcaccc |
| | | agagccgccgagaccgccgccgggccgccgaccgaggccggactccggatcggctccacgcgaagcctgggagatgaaggctggtcgagacct |
| | | aactctcggcacatgctgaaggcctaccgctgccggctaccgatcggcaccgagcctccatctcgggtgttcatcgacgggcagatccagccgcc |
| | | gctcgacatgctgactacaagctggtccccggctaccgggtctccgtccacggagatcaccgcggccttcggcgagcagaagttcta |
| | | ggtcaagctcgatcagcgattctcccgggactggtgcgcgactcgccgactcggcccgaccagccaccgcgaggagctgaactgtc |
| | | ccgaccggacacgtcgcgaggtcagaagtcccaagctggaggcggtgttcggcgaccaggagggcactgcactgggacgtgacaactcaag |
| | | gcagggcgaattcgtcacggtctccaagctgaggcggtcgtgtccccaccggaagaggcactgcacgtccacggatccgcgctgacgactctacggc |
| | | aacacgcgcggtctcatcgtcgggtcgtgtccccaccgaggccacctgcggcgtatgagatcccgcgtgacttcctcgtcg |
| | | tcgccgactcactgactgcaggaccgggcgagccgcgtgccgctcaggaccggggacttcagtcagtgaccgccgacgctcgtcg |
| | | agacaacctacacggagaaccgcctgctgacccgcgatccgcggtatccgaaagctggccggccactggcccgaactgaaggcgcactacg |
| | | gcgaaccgcctgaacagctctacaccgacctggccggccgggcaggccaacgagttgccgagttcgctccgcggatctgcggtccgatgc |
| | | gaccaccacccgatctggtcggagactgggtggagattcgtggcgcctctgagcttctgaacctgcacgagatcctgcacgatcttcgatgtcgactgccg |
| | | agacttcacccgatctggtcggagactgggtggagattcgtggcgcctctgagcttctgaacctgcacgagatcctgcacgatcttcgatgtcgactgccg |
| | | gcccggcgtcatcgtcagccccgacgacctggaccgccaggccgcaggcggcggtcgactgaggggcgaactgcgcgctccaagcg |
| | | gtcggcgtcatcgtcagccccgacgacctggaccgccaggccgcaggcggcggtcgactgaggggcgaactgcgcgctccaagcg |

TABLE 14-continued

Sequences

| SEQ ID NO | Description | Sequence |
|---|---|---|
| | | ccccatacgcgtggtgacgggcgcgacgcaccgaagtgcgcgacgtgatctcgccctggcaagttcatcgacg |
| | | ccaagaccgtccgcgcgcggtctgccggttcggcgacgagatccgcaccgtgctgaccggcggccacggg |
| | | ttcctgggcgctactgccgctgagaatggctggagcgcatgaccggtggacgccaagtgatctgcctgtgcgcgccc |
| | | gcgacgaccgaggccgcccggcgtctgaccgacgtcgacaccgggacgcgacactgtcgacactaccgcg |
| | | cgctggcagccgatcacccgtcgagtctgatcgtcgggtcggccgtcgatcggccgtcaacgactggcag |
| | | cgactggctcggcgacaccgtcgatctgatctgtcgccgaaatcatccggatccgcgtgaccaccaagccgactacgtcctgcccggtcaatccctgctacagcgacgtacgtcgacgttcgacc |
| | | caatgcgctcggcaccgcgcgaactcatccggatccgcgtcgtgaggacgccgacatccgcgagaatccgcgagatcagcgacgcgcgggccgacg |
| | | gtgggacagggcattcccccgaggcgtctgtggaagacccggaggacgccgtcgtgagggagcccaacaacgtggtgtctg |
| | | actctacgccacgcaagcaacagacgactgcgagcaacgtgatcacctgggtgtgcgacactgcgcagatccacccg |
| | | cggtctcgtgtttcgctcgaacatgatcctggccgcgacgtcaccggagcggagatcagtgctgccacccagcgcgc |
| | | cctatgtgagcctcgtgcgcgaccggatcgcgcgcgccgaggcgatctcacgacggacggtcaccgacggattcgagac |
| | | gttccaagtgtgaaccgcgacgacgagcatcgacgtagcgacggctggcgaaggcggctaaccccgct |
| | | gcaccgtcgacgactacgcccaccctggccgagcggtcgaaacgccatcggcccctccgcgaggcaacgtcag |
| | | gcctcgctgcgctgctgcgtcgacaactatcagacgcccgacaaaggacattccgacgcacgtcgacgcaccgaccggttcc |
| | | gtgcgcggtgcaggacggcaggaagactcgggccccgacaggatcggcccacgacggcctcgaaacgccatcggccccg |
| | | agcaacctgcagatgctcggattgctgtaa |
| 42 | FadD9 (DNA) | atgtcgatcaacgatcagggcgactgacacgccgtcgaggactctatacgccagccgcgaccgccagttcgccgccgcagtccc |
| | | aacaggcgatcaccaggcgatcgaccagccgggtcgcgcttccacacgtcgcgcttcatccgctatgtcatggagggctacgcc |
| | | gatggccggcactcggccgtgcgtcgccggaactgtgggccccgcggcactggccgtcaacagtcagctggtcgagtcactgcc |
| | | gcggtcgagacatcaccaccggagacccgggtttgctgctgggcttcaacaagcagtcgactcgactacacaaccatcgactcgccggtgggc |
| | | gcctgtcggttccactcgagacaacttggcgacgcgtgagcctgtcggcccgatcgcccggactcggccacgcgagatc |
| | | gccaccagatcgacaattggggcgacgggccctgaagcatcccgcgagtcgtgcccgcggtcactgcctcgattacc |
| | | acggcaaggtgacaccccaccggagcgtgaagctgcggttgagcgcatgggccgaggtcgatgaccatcgacaacactt |
| | | gccgaactgatgcaacgcggcagggcgctgcccgaagccaggcagaccagaccgccgagacagcgtgcgctgctga |
| | | tttcacccgggtagtaacgcggagcggttaccccgcgatcacgctgaactttcatgcgcgagagcagtggagtgagggtcaagtcgag |
| | | tggctgtcgagtccagcgagcggttacccctgcgatcacgctgaacttcatgcgcgatgagagccgccaggtcgcaggtgctct |
| | | acggagccgttccaaggcgtaccgcacttcgtcgccaagagcgacctcgcctgtcgaagaccctgccccggt |
| | | gcggcccacagaattgtgcttcgtcgccgcatctggacatggtgtcgcagccatggtcgacagcgagtgcacgcccgcttg |
| | | gtgacgggccgatcgacggcgctgagcggcctgaaggcgcagtgaagcgcgagctgcgggagaacgtctcgcggacggttt |
| | | tcatggcgctgcatgacccggtccgcgcccgatctccgcgatcaccgcgtgagaatgaccgctgggtcgagtgcgacgtgcatttgat |
| | | ggagggtactacgcgtgaagcggctacggtctcagaccatggtgcccggcgagtctgcggtcgtcaagaacgcaaaca |
| | | tgtccccgctataccagccgcccgatgcctcaccgaggtgtccaccgacgctcaaagctctccaggggagttcatcgcc |
| | | gtgaaaggcccgacgacactaccagccgcgcaactgcgcccgcaacaacgctcaaagctcatctacgcaacagtcccgcccgctacc |
| | | gtgtcgagtaggcgccgatgggcggttcggcgaggcggtgttctcctccgggaccgctctcctccccatgcggccgaccgctggtgtgtcgtgatcagcgagtccctg |
| | | caggaggtacgaggccgtcaccggcatccaagtgcaccgccgctgcgaccccgcagtgaagaagttctatggcaaccgctcgagcggctc |
| | | gagacgaagctcgatgcgcacccaggtagcaatcacaagcgatgcagcgctgcacgacttcgcccctacgcgcgacg |
| | | tataccgagtccggccggcgattgcgtgtgggctctaccgagggtccggagcactcgccgaccgcggtcgtcgacg |
| | | actgctcgagctcggccgtgtcgttgccgcaaacctgctggacgatcttcggcgtcggcgtgggtgtcattgtcagcccg |
| | | gcaagggaccggcggcctccaccgacggaccacatcgaagcagcgcgtcaggcgaccagcttcaggaacgtcgatac |
| | | ccgaacctgccgagcccgaccgcaccccagtcgacgcctatgctgcgaccgctgagcctcacgctgacgctgaccttcatcgctgcacctgtggtcagccgg |
| | | gcaagcgcgcaccgctgcagcagctacgtactgcacctgtaccccgcaccgcagggcaccggcttgggagctcgccgcagcctgaccttggtcacccggtgcaccctccaccggcgctgggtcacggcg |

TABLE 14-continued

Sequences

| SEQ ID NO | Description | Sequence |
|---|---|---|
| | | ctggaatggctcgaccgcatgaccgactggtcaacgcaagctgatctgcctggtccgcgaggaagcacaa |
| | | gccggtcgaccgacgcgacgttcgatagcgcgaccgtattggtcggcactaccggcactccgccctcga |
| | | ggtgctcgccggcgacaaggcgaaggcgaccctgggccctgggcacgagggctcccgccgcgcggtgga |
| | | cctgatcgtggaccccgccggcctggtcaaccacgtgccgtccgtatagcagctgttggccaaacgcggcggcaccgc |
| | | cagtgcttcggcggcgtgaccgcgcaagcgcaccatactacaccctcgacatcgccgtgggcgagcagatccc |
| | | gccgaggcgttcaccgagacggcgacgcgacatccgggcccatcagccgacgccgaagctgacgacagcaacgg |
| | | ctacgacagcaggcaagtgggcggccgacaccagctataccggtgctgctgcgaagctcaacctgccgacagtgtcacccggctgatgctgagcctg |
| | | gctcgacatgatcctggccgacaaccgcgttcgtatgagcgactgtctatgatcgcaactatgacggctgc |
| | | cggtgaattcgtcgcagaagccattgcaccctgggacaacatagccgccgaccgtttgtcacctaccacgtgatgaacccct |
| | | acgacgacggcatcgggctggacagttcgaccgactgaagacttcgctcgcgtgcctcgcagcgccctcgctgct |
| | | gcccctgctgcacaactaccgagagccctcaaacgcgatatgcgggtcaatcgcccaccgaccagttccgcgctgcgtc |
| | | caagaagcgaaatcggtccgacaagacattccgcacctcaccgcggcgatcatcgcgaagtacatcagcaacctgtga |
| | | ctgctcgggctgctgtga |
| 44 | carB60 (DNA) | atgggcagcagccatcatcatcatcatcacgagcagcggcctggtgccgcgcggcagccatATGACGAGCCGATG |
| | | TTCACGACGCGACCGACCGGCGTTACCGACGACTGCACTGGATGATGAGCAGA |
| | | GCACTCGTCGTCGTATTGCCAGAACTGTACGCAACGACCCAGAGTTCGCAGCAG |
| | | CAGCTCCTTCGCCGGCCGTTGTCGATGCGGCGCACAAACCGGCCTGCGTCT |
| | | GGCCGAAATCCTGCAGACCCTGTTCACCGGCTACGCCGGATCGTCGGCCT |
| | | GGGCTATCGTGCACCTGAGCTGCGACGGACGAAGGCGGTCGTACGGTCAC |
| | | GCGTCTGCTCGCCGCGCTTCGATACCCTGACCTATGCACAGGTGTGGAGCCGT |
| | | GTTCAAGCAGTGGCTGCAGCGTTCGCAGCCTATGCCACAATTCGCACAACCGATTTACC |
| | | CGGGCGACGCGGTTCGCGACATATCGCGGCCTGTCAGCGTTCTTTGCAGCATAA |
| | | TGGATCTGGTTGTGCGCGTATCGGGCCTGCCTGTCAGCGTTCTTTGCAGCATAA |
| | | CGCTCCGGTGTCTCCGCTGGCCCCGATTCTGGCCGAGGTGAACCGCGTATT |
| | | CTGACGGTGAGCGCAGAATACCTGGTTGTTTTCGACCATCATCCGGAAGTGACG |
| | | GTGAACTCCGTCAGCCAGCTGGTTGTTTTCGACCATCATCCGGAAGTGACG |
| | | ATCACCGTGACGCACTGCCGCGCCACGCCAGCACGCTGGCCGCCAAAGGTA |
| | | TCGCAGTTACGACCCTGATGCGATCGCAGACGAAGGCGCAGGTTTGCCGG |
| | | CTGAGCCGATTTACACGCGGATCACGATCAGCGTCTGGCCATGATTCTGTA |
| | | TACCAGCGGCTTCACGGGTCCTGTGACTATGAGCTTTATCACGGCGATGTACACCGAAGCGAT |
| | | GGTGGCTCGCCTGTGACTATGAGCTTTATCACGGCGACCCCGTT |
| | | ATCAACGTGAACTTCATGCCGCTGAACCATCTGGGCGTCTGTATCCCGATTA |
| | | GCACCGCCGTGCAGAATGGCGGTACCAGCTACTTCGTTCCGGAAAGCGACA |
| | | TGAGCACGCGTGTTTGAGGATCTGTACCAGCATCATCTGGCGACCGTGGA |
| | | GGTGCCGCGTGTTGCGGACATCGTGTACCAGCATCATCTGGCGACCGTGA |
| | | TCGCCTGGTGACCCAGGGCGCGGAGACGAACTGACTGCGGAAAAGCAGGCCG |
| | | GTGCGGAACTGCGTGAACAGGTCTTTGGGCGGTCGTGTGTTATCACCGGTTTTGT |
| | | TTCCACCGGCCCGTTGGCGCGGAGAGATGCGTGCTTTTCTGGATATCACCTTG |
| | | GGTGCACACCGTGTTGACGTTACGGTCTGACCGAAACCGGTCGGTCACC |
| | | CGTGATGGTGATGTTCTCCTCCGGTCATTGATTACAAGCTGATCGATG |
| | | TGCCGGAGCTGGGTTACTTCTCACCGACAAACCGTACCCCGTGGCGAGC |
| | | TGCTGGTTCGTAGCCAAACGTTGACTCCGGTTACTACAAGCGCCAGAAG |
| | | TCACCGTCCGTTTTCGATCGGCGCTATTACCACCGGCGACGTGAT |
| | | GGCAGAAACCGCCAGACCCTGTGTATGTGACCGCCGCAACAATGT |

TABLE 14-continued

Sequences

| SEQ ID NO | Description | Sequence |
|---|---|---|
| | | TCTGAAGCTGGCGCAAGGTGAATTTGTCGCCGTGCCTAACCTGGAGGCCGT
TTTCAGCGCGCTGCTCTGTCCGCAGATTTCGTGTATGGTAACAGCGGAG
CGCAGCTTTCTGTTGGCTGTTGTGTCCCTACCCCGGAGGCGCTGGAGCAAT
ACGACCCTGCCGCATTGAAAGCAGCCCTGGCGGATTCGCTGCAGCGTACGG
CGCGTGATGCGAGCTGCAGAGCTATGACGATGCCGCGGACTTCATTGTTG
AGACTGAGCCTTTTAGCGCTGCGAACGGTCTGCTGAGCGTGTTGGCAAGTT
GCTCCGCTCCGAATTTGAAGGATCGCTACGGTCAGCGTTTGAGCAGATGTA
CGCGGACATCGCGGCTACGCAGGCGAACCAATTGCGTGAACTGCCGCGTGC
TGCGCTACTCAACCGGTGATCGACACGCTGACGCAAGCTGCGGCGACCAT
CCTGGGTACCGGCAGCGAGGTTGCAAGCGACGCACACTTTACTGATTTGGG
CGGTGATTCTCTGAGCGCGCTGACGTTGAGCAACTTGCTGTCTGACTTCTTT
GGCTTTGAAGTCCCCGGTTGGCACGATTGTTAACCCAGCACTAATCTGGCAC
AGCTGGCGCAACATATCGAGGCGCACAGCTGGAACGTTTGGCACCGGTT
CCTTTACGACGGTCCACGGTGCGGATGCTACGGAAATCCGTGCAAGCGAAC
TGACTCTGGACAAATTCATCGACGCTGAGACTCTGCGCGCCAGCACCTGTTT
GCCGAAGGTTACGACTGAGCCGCGTCCGTTGTTGAGCGGTGCCAATGG
TTGGTTGGGCGCGTTCCTGACCCCTGCAGTGGCTGGAACGTTTGGCACCGGTT
GGCGGTACCCTGATCACCATTGTGCGCGGTCGTGACGATGCAGCGGCACGT
GCACGTTTGACTCAGGCTTGACGAATACGACCCAGAGCTGTCCCGCCGCTTCG
CTGAGTTGGCGGATCGCCACTTGCGTGTGTGGCAGGTGATATCGGCATC
CGAATCTGGGCCTGACCCCGAGATTTGCACCGTCTGCAGCAGAGGTCG
ATCTGGTCGTTCATCAGCGCCCCTGGTCAACCACGTCCTGCCGTACCGCCA
GCTGTTTGGTCCGAATGTTGTTGGCACCGCGAAGTTATCAAGTTGGCTCTG
ACCGAGCGCATCAAGCCTGTTACCTACCTGTCCACGGTTAGCGTCGCGATGG
GTATTCCTGATTTTGAAGGAGGACAGCATTCGTACCGTGACGCCCGGTTCG
TCCGCTGGATGGTGCTATCGAAATGGCTATGGCAACAGCAAGTGGGCTGG
CGAGGTGCTCGTCCGCGAGGCACATGACCTGTGTGGCCTGCCGGTTGCCGAC
GTTTCGTAGCGACATGATTCGGCCCACCCGCGTCCTGCCTGATCACGGGTGTGG
GTGCCGGACATGTTCACCCGTCGCTGCTGCAGCGTCCGCGTGCACTACCC
CACCCGTTCCTTCACATTGGTGATGGCGAGCGTCCGCGTGCACACTACCC
GGGCCTGACCCGTCGATTTTGTTGCCGAAGCGGTTACTACCCTGGGTGCTCAG
CAACGTGAGGGTTATGTCTCGTATGACGTTATGAATCCGCACGATGACGGT
ATTAGCTTGGATGTCTTTGTGGACTGGCTCGATTCGTGCGGCCACCCAATTG
ACCGTGTTGACGACTATGATGACTTGGCTCGTGTCGTTTGAAACCGCGTTGAC
CGCCTTGCCCGGAGAAACGTCTGCGCCAGACCGTTCGCCCCTGCTCATGCC
TTTCGCGCCACAGGCGCCGTTGCGTTGCGCCCCTGAACCGACCGAAGTG
TGGATGAAGCCCTGATCGACAAGTACATCCGTGACCCTGCCGAGTTCGGTC
TGATTTAG |

What is claimed is:

1. A variant carboxylic acid reductase (CAR) polypeptide comprising an amino acid sequence having at least 85% sequence identity to the wild-type CAR polypeptide of SEQ ID NO: 7, wherein said variant CAR polypeptide is genetically engineered to have at least one mutation at an amino acid position selected from the group consisting of S3R, D18R, D18L, D18T, D18P, E20V, E20S, E20R, S22R, S22N, S22G, L80R, R87G, R87E, V191 S, F288R, F288S, F288G, Q473L, Q473W, Q473Y, Q473I, Q473H, A535S, D750A, R827C, R827A, I870L, R873S, V926A, V926E, S927K, S927G, M930K, M930R and L1128W, wherein expression of said variant CAR polypeptide in a recombinant host cell results in a fatty alcohol composition, a fatty aldehyde composition or a composition that is a mixture of fatty aldehydes and fatty alcohols wherein the fatty alcohols and fatty aldehydes are produced at a higher titer than is produced by a recombinant host cell expressing the wild type CAR polypeptide of SEQ ID NO:7.

2. The variant CAR polypeptide of claim 1, wherein said variant polypeptide comprises:
   (a) mutation A535S;
   (b) mutations E20R, F288G, Q473I and A535S;
   (c) mutations E20R, F288G, Q473H, A535S, R827A and S927G;
   (d) mutations E20R, S22R, F288G, Q473H, A535S, R827A and S927G
   (e) mutations S3R, E20R, S22R, F288G, Q473H, A535S, R873S, S927G, M930R and L1128W;
   (f) mutations E20R, S22R, F288G, Q473H, A535S, R873S, S927G, M930R and LI 128W,
   (g) mutations D18R, E20R, S22R, F288G, Q473I, A535S, S927G, M930K and L1128W;
   (h) mutations E20R, S22R, F288G, Q473I, A535S, R827C, V926E, S927K and M930R;
   (i) mutations D18R, E20R, 288G, Q473I, A535S, R827C, V926E, M930K and LI 128W;
   (j) mutations E20R, S22R, F288G, Q473H, A535S, R827C, V926A, S927K and M930R;
   (k) mutations E20R, S22R, F288G, Q473H, A535S and R827C;
   (l) mutations E20R, S22R, F288G, Q473I, A535S, R827C and M930R;
   (m) mutations E20R, S22R, F288G, Q473I, A535S, I870L, S927G and M930R;
   (n) mutations E20R, S22R, F288G, Q473I, A535S, I870L and S927G;
   (o) mutations D18R, E20R, S22R, F288G, Q473I, A535S, R827C, I870L, V926A and S927G;
   (p) mutations E20R, S22R, F288G, Q473H, A535S, R827C, I870L and L1128W;
   (q) mutations D18R, E20R, S22R, F288G, Q473H, A535S, R827C, I870L, S927G and L1128W;
   (r) mutations E20R, S22R, F288G, Q473I, A535S, R827C, I870L, S927G and L1128W;
   (s) mutations E20R, S22R, F288G, Q473I, A535S, R827C, I870L, S927G, M930K and L1128W;
   (t) mutations E20R, S22R, F288G, Q473H, A535S, I870L, S927G and M930K;
   (u) mutations E20R, F288G, Q473I, A535S, I870L, M930K;
   (v) mutations E20R, S22R, F288G, Q473H, A535S, S927G, M930K and L1128W;
   (w) mutations D18R, E20R, S22R, F288G, Q473I, A535S, S927G and L1128W;
   (x) mutations E20R, S22R, F288G, Q473I, A535S, R827C, I870L and S927G;
   (y) mutations D18R, E20R, S22R, F288G, Q473I, A535S, R827C, I870L, S927G and L1128W;
   (z) mutations D18R, E20R, S22R, F288G, Q473I, A535S, S927G, M930R and L1128W;
   (xx) mutations E20R, S22R, F288G, Q473H, A535S, V926E, S927G and M930R; or
   (zz) mutations E20R, S22R, F288G, Q473H, A535S, R827C, I870L, V926A and L1128W.

3. A recombinant host cell comprising a polynucleotide sequence encoding a variant carboxylic acid reductase (CAR) polypeptide having at least 85% sequence identity to the wild-type CAR polypeptide of SEQ ID NO: 7 and having at least one mutation at an amino acid position selected from the group consisting of S3R, D18R, D18L, D18T, D18P, E20V, E20S, E20R, S22R, S22N, S22G, L80R, R87G, R87E, V191 S, F288R, F288S, F288G, Q473L, Q473W, Q473Y, Q473I, Q473H, A535S, D750A, R827C, R827A, I870L, R873S, V926A, V926E, S927K, S927G, M930K, M930R and L1128W, wherein the recombinant host cell produces a fatty alcohol composition, a fatty aldehyde composition or a composition that is a mixture of fatty aldehydes and fatty alcohols wherein the fatty alcohols and fatty aldehydes are produced at a higher titer or yield than is produced by a host cell expressing the wild type CAR polypeptide of SEQ ID NO: 7 when cultured in a medium containing a carbon source under conditions effective to express said variant CAR polypeptide.

4. The recombinant host cell of claim 3, further comprising a polynucleotide encoding a thioesterase polypeptide.

5. The recombinant host cell of claim 4, further comprising a polynucleotide encoding
   (i) a FabB polypeptide and a FadR polypeptide, or
   (ii) a fatty aldehyde reductase.

6. The recombinant host cell of claim 3, wherein the titer or yield is at least 3 times greater than the titer or the yield of a host cell expressing the corresponding wild type CAR polypeptide when cultured under the same conditions as the recombinant host cell.

7. The recombinant host cell of claim 6, wherein the titer is in a range that is between 30 g/L to 250 g/L, or between 90 g/L to 120 g/L.

8. The recombinant host cell of claim 7, wherein the yield is in a range that is between 10% to 40%.

9. A cell culture comprising the recombinant host cell of claim 3.

10. The cell culture of claim 9 wherein the cell culture has productivity that is at least 3 times greater than the productivity of a cell culture that expresses the corresponding wild type CAR polypeptide.

11. The cell culture of claim 10, wherein said productivity ranges from 0.7 mg/L/hr to 3 g/L/hr.

12. The cell culture of claim 9, wherein the fatty alcohol composition, fatty aldehyde composition or composition that is a mixture of fatty aldehydes and fatty alcohols collects in an organic phase extracellularly.

13. The cell culture of claim 12, wherein the fatty alcohol composition, fatty aldehyde composition or composition that is a mixture of fatty aldehydes and fatty alcohols comprises one or more of a C6, C8, C10, C12, C13, C14, C15, C16, C17, or C18 fatty alcohol, fatty aldehyde or combination thereof.

14. The cell culture of claim 12, wherein the fatty alcohol composition, fatty aldehyde composition or composition that is a mixture of fatty aldehydes and fatty alcohols comprises a C10:1, C12:1, C14:1, C16:1, or a C18:1 unsaturated fatty alcohol or a C10:1, C12:1, C14:1, C16:1, or a C18:1 unsaturated fatty aldehyde or a combination thereof.

15. The cell culture of claim 12, wherein the fatty alcohol composition, fatty aldehyde composition or composition that is a mixture of fatty aldehydes and fatty alcohols comprises C12 and C14 fatty alcohols and/or C12 and C14 fatty aldehydes.

16. The cell culture of claim 15, wherein the fatty alcohol composition, fatty aldehyde composition or composition that is a mixture of fatty aldehydes and fatty alcohols comprises C12 and C14 fatty alcohols and/or C12 and C14 fatty aldehydes at a ratio of about 3:1.

17. The cell culture of claim 12, wherein the fatty alcohol composition comprises unsaturated fatty alcohols, the fatty aldehyde composition comprises unsaturated fatty aldehydes and the composition that is a mixture of fatty aldehydes and fatty alcohols comprises unsaturated fatty alcohols and unsaturated fatty aldehydes.

18. The cell culture of claim 17, wherein the unsaturated fatty alcohols and unsaturated fatty aldehydes have a double bond at position 7 in the carbon chain between C7 and C8 from the reduced end of the fatty alcohol or fatty aldehyde.

19. The cell culture of claim 12, wherein the fatty alcohol composition comprises branched chain fatty alcohols, the fatty aldehyde composition comprises branched chain fatty aldehydes and the composition that is a mixture of fatty aldehydes and fatty alcohols comprises branched chain fatty alcohols and branched chain fatty aldehydes.

20. A method of making a fatty alcohol composition, a fatty aldehyde composition or a composition that is a mixture of fatty aldehydes and fatty alcohols composition at a high titer, yield or productivity, the method comprising:
  (a) culturing a recombinant host cell that comprises a polynucleotide sequence encoding a variant carboxylic acid reductase (CAR) polypeptide having at least 85% sequence identity to the wild-type CAR polypeptide of SEQ ID NO: 7 and having at least one mutation at an amino acid position selected from the group consisting of S3R, D18R, D18L, D18T, D18P, E20V, E20S, E20R, S22R, S22N, S22G, L80R, R87G, R87E, V191 S, F288R, F288S, F288G, Q473L, Q473W, Q473Y, Q473I, Q473H, A535S, D750A, R827C, R827A, I870L, R873S, V926A, V926E, S927K, S927G, M930K, M930R and L1128W, in a medium comprising a carbon source under conditions effective to express the variant CAR polypeptide; and
  optionally, isolating the fatty alcohol and/or fatty aldehyde composition from said medium.

* * * * *